United States Patent
Wunderlech et al.

(10) Patent No.: US 11,091,490 B2
(45) Date of Patent: Aug. 17, 2021

(54) 3-AMINO-1,5-DIHYDRO-PYRAZOLO[3,4-D]PYRIMIDIN-4-ONES AS CYCLIN DEPENDENT KINASE INHIBITORS

(71) Applicants: Oncotyrol Center for Personalized Cancer Medicine GMBH, Innsbruck (AT); Vichem Chemie Kutató Korlátolt Felelősségü Társaság, Budapest (HU)

(72) Inventors: Winfried Wunderlech, Bovenden (DE); Lukas A. Huber, Schwaz (AT); Johann Jakob Leban, Innsbruck-Igls (AT); János Pató, Budapest (HU); László Örfi, Budapest (HU); Wáczek Frigyes, Budapest (HU); Péter Bánhegyi, Budapest (HU); Anna Sípos, Dunakeszi (HU); Csaba Szántai-kis, Budapest (HU)

(73) Assignees: MEDIZINISCHE UNIVERSITÄT INNSBRUCK, Innsbruck (AT); Vichem Chemie Kutató Korlátolt Felelősségü Társaság, Budapest (HU)

( * ) Notice: Subject to any disclaimer, the term of this patent is extended or adjusted under 35 U.S.C. 154(b) by 0 days.

(21) Appl. No.: 16/464,860

(22) PCT Filed: Nov. 29, 2017

(86) PCT No.: PCT/EP2017/080786
§ 371 (c)(1),
(2) Date: May 29, 2019

(87) PCT Pub. No.: WO2018/099952
PCT Pub. Date: Jun. 7, 2018

(65) Prior Publication Data
US 2020/0247809 A1    Aug. 6, 2020

(30) Foreign Application Priority Data
Nov. 30, 2016  (EP) ..................... 16201321

(51) Int. Cl.
*C07D 487/04* (2006.01)
*A61P 35/04* (2006.01)
*C07D 519/00* (2006.01)
*A61K 9/00* (2006.01)

(52) U.S. Cl.
CPC ............ *C07D 487/04* (2013.01); *A61P 35/04* (2018.01); *C07D 519/00* (2013.01); *A61K 9/0019* (2013.01); *A61K 9/0053* (2013.01)

(58) Field of Classification Search
CPC ... C07D 231/38; C07D 487/04; C07D 519/00
See application file for complete search history.

(56) References Cited

U.S. PATENT DOCUMENTS 4,163,846 A    8/1979  Judson

FOREIGN PATENT DOCUMENTS

WO       2002067654 A2    9/2002
WO    WO 2002/067654    *   9/2002

OTHER PUBLICATIONS

Ibraham, D.A. et al., "Structure-based design of a new class of highly selective pyrazolo[3,4-d]pyrimidines based inhibitors of cyclin dependent kinases," Arkivoc, vol. 7, pp. 12-25 (2009).
Declercq, J.P. et al., "Phenyl-1 Dimethylamino-3 Cyano-4 Amino-5 Pyrazole," Acta Chystallographica, vol. B33, No. 2, pp. 413-416 (1977).
Database Registry Chemical Abstracts Service, Columbus, OH, US, Aug. 21, 2016, XP002766465, Data Accession No. 1976715-13-5.
Database Registry Chemical Abstracts Service, Columbus, OH, US, Aug. 18, 2016, XP002767356, Data Accession No. 1975157-45-9.
Database Registry Chemical Abstracts Service, Columbus, OH, US, Aug. 5, 2016, XP002767357, Database Accession No. 1967831-65-5.
International Search Report and Written Opinion for corresponding PCT patent application PCT/EP2017/080786 (10 pages).

* cited by examiner

*Primary Examiner* — Valerie Rodriguez-Garcia
(74) *Attorney, Agent, or Firm* — Greenberg Traurig, LLP; Jonathan D. Ball

(57) ABSTRACT

The present invention relates to 3-amino-pyrazolo[3,4-d]pyrimidin-4-ones, such as for example, N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-2-diethylamino-acetamide, particularly useful as cyclin dependent kinase (CDK) inhibitors, pharmaceutical compositions comprising the same and the use thereof in particular in the prophylaxis and/or treatment of cancer and other proliferative diseases. Furthermore, the present invention relates to processes for the synthesis of said 3-amino-pyrazolo[3,4d]pyrimidin-4-ones and intermediates to be used in the processes of the present invention.

4 Claims, 7 Drawing Sheets

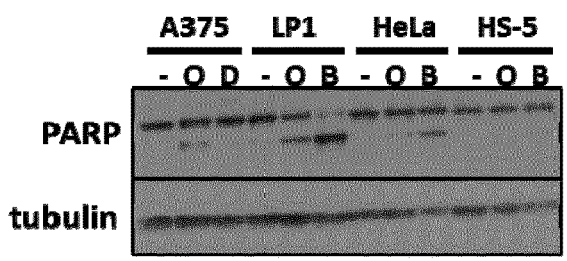

Figure 1: (A) Cell cycle analysis of three cancer cell lines (LP1 multiple myeloma cells, A375 melanoma cells, HeLa cervix carcinoma cells) and control cells (HS-5 bone marrow stroma cells) after 12 and 24 h of treatment with 0.1 µM Otviciclib. All three tumor cell lines showed cell cycle defects and a progressive enrichment of the sub G1 group, a sign of fragmented nuclei in apoptosis, in a propidium iodide FACS analysis. (B) Western blot analysis of the respective cell lines with anti PARP antibody after 24 h of treatment with 0.08 µM Otviciclip showed induction of PARP cleavage in tumor cell lines. O... Otviciclib; D... Dinaciclib (10 nM); B... Bortezomib (20 nM).

Figure 2 cont.:

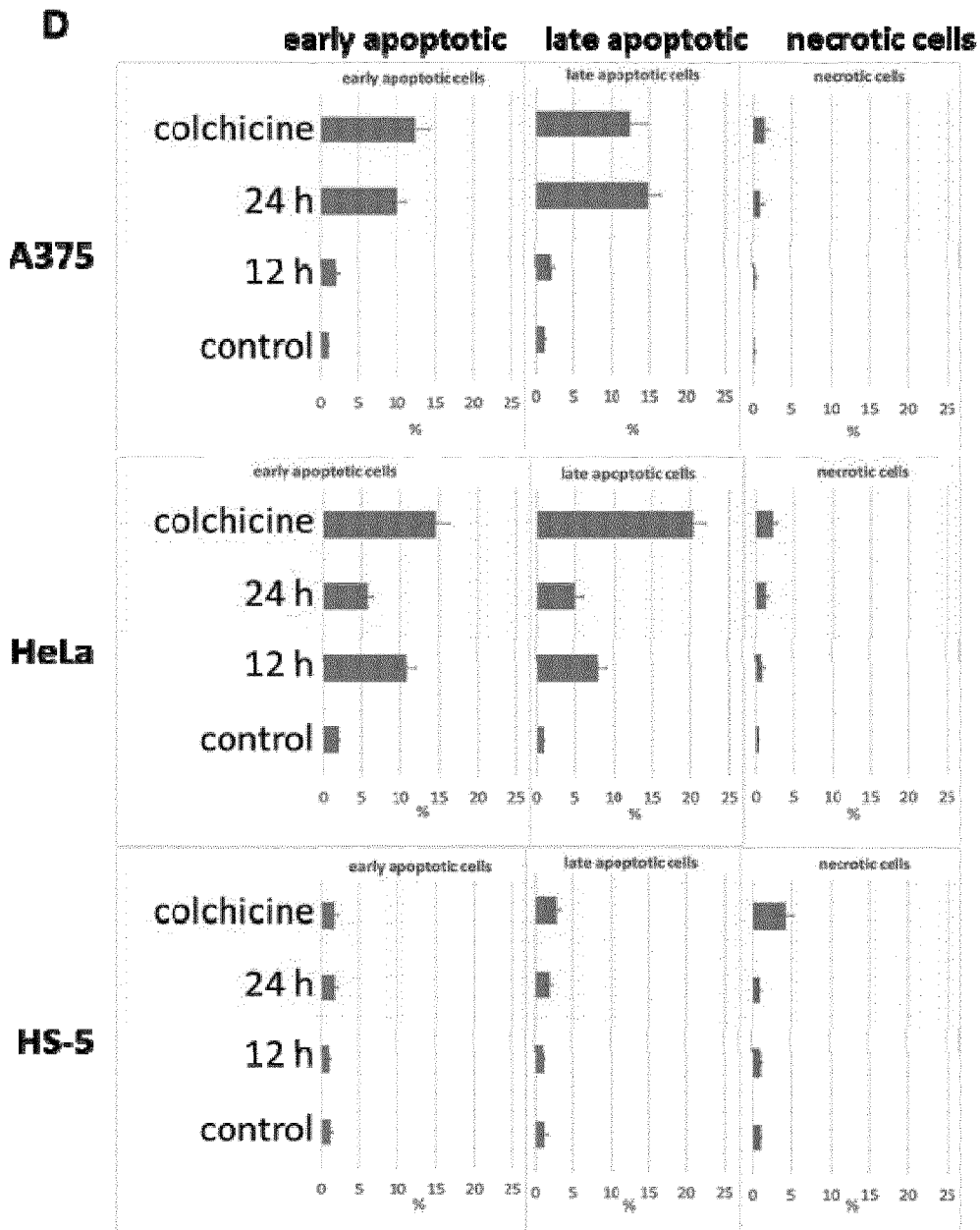

Figure 2: Images (10 x) of Annexin V/PI staining of two cell lines from solid tumors and control cells after 12 and 24 h of treatment with 0.1 µM Otviciclib. (A) A375 melanoma cell line. (B) HeLa cervix carcinoma cell line. (C) Control cell line HS-5 derived from bone marrow stroma. (D) Quantification of early apoptotic cells (Annexin V positive), late apoptotic cells (Annexin V/PI co-staining) and necrotic cells (PI positive cells) after Otviciclib treatment. Otviciclib showed a reproducible induction of apoptosis in tumor cells compared to control cells (n=3). 12 h... Treatment with 0.1 µM Otviciclib for 12 hours; 24 h... Treatment with 0.1 µM Otviciclib for 24 hours. Colchicine... treatment with 0.6 µg/ml colchicine for 24 hours.

3-AMINO-1,5-DIHYDRO-PYRAZOLO [3,4-D]PYRIMIDIN-4-ONES AS CYCLIN DEPENDENT KINASE INHIBITORS

CROSS REFERENCE TO RELATED APPLICATIONS

This application is the U.S. national phase application, pursuant to 35 U.S.C. § 371, of International Application No. PCT/EP2017/080786, filed Nov. 29, 2017, which claims the benefit of European Patent Application No. 16201321.3, filed Nov. 30, 2016, the entire contents of which are hereby incorporated by reference in their entirety.

FIELD OF THE INVENTION

The present invention relates to novel 3-amino-1,5-dihydro-pyrazolo[3,4-d]pyrimidin-4-ones carrying substituents at positions 1 and 6 and their pharmaceutically acceptable salts, solvates and prodrugs thereof, pharmaceutical compositions comprising the same and the use thereof, in particular in the prophylaxis and/or treatment of cell proliferative diseases, infectious diseases, pain, asthma, diabetes, neurodegenerative diseases, cardiovascular diseases and inflammation.

It has been found that the compounds according to the present invention are potent kinase inhibitors and are particularly selective for a subset of cyclin dependent kinases (CDKs).

Furthermore the present invention relates to processes for the synthesis of said 3-amino-1,5-dihydro-pyrazolo[3,4-d] pyrimidin-4-ones their pharmaceutically acceptable salts and solvates thereof and intermediates to be used in the processes of the present invention.

BACKGROUND OF THE INVENTION

Protein kinases play important roles in regulating most cellular functions—proliferation/cell cycle, cell metabolism, survival/apoptosis, DNA damage repair, cell motility, response to the microenvironment and inflammatory response. Misregulation of protein kinase function has been found to be associated with oncogenes. Kinases such as c-Src, c-Abl, mitogen activated protein (MAP) kinase, phosphotidylinositol-3-kinase (PI3K) AKT, and the epidermal growth factor (EGF) receptor are commonly activated in cancer cells, and are known to contribute to tumourigenesis. Many of these occur in the same signalling pathway—for example, HER-kinase family members (HER1 [EGFR], HER3, and HER4) transmit signals through MAP kinase and PI3 kinase to promote cell proliferation.

Kinases have thus emerged as one of the most intensively pursued targets in current pharmacological research, especially for cancer, due to their critical roles in cellular signalling. To date, the US FDA has approved 28 small-molecule kinase inhibitors, half of which have been approved in the past 3 years.

Human cancers are characterised by altered cell cycle regulation.

Most clinically used anti-cancer drugs kill rapidly growing cells non-specifically, with the result that they not only kill pathologically transformed cancer cells but also non-pathological rapidly dividing cells such as haematopoietic bone marrow progenitor cells, hair follicle cells and gastrointestinal mucosal epithelial cells.

The uncontrolled proliferation characteristic of cells of several human/mammalian cancers is associated with the dysregulation of cyclin dependent kinases (CDKs)/cyclins. Cyclin dependent kinases (CDKs) are critical regulators of cell cycle progression and play also central roles in a wide variety of important physiological processes, including transcription and neuronal function.

CDKs are heterodimeric serine/threonine kinases composed of a catalytic subunit and a regulatory cyclin subunit. Deregulated CDK activities as a result of gene amplification, translocation or point mutations of CDKs or cyclins have been reported in the majority of human (and other mammalian) cancers.

CDKs are ubiquitously expressed throughout the cell cycle, however, the periodic expression and subsequent degradation of the cyclins at distinct phases of the cell cycle ensures the tight regulation of CDK activities in an orderly manner for proper cell cycle progression (Santo et al., Seminars in Oncology, Vol. 42, No 6, December 2015, pp. 788-800).

The human genome encodes 21 CDKs, although only seven (CDK1-4, 6, 10, 11) have been shown to have a direct role in cell cycle progression. Other CDKs play an indirect role via activation of other CDKs (CDK3), regulation of transcription (CDK7-9) or neuronal function (CDK5) (Sanchez-Martinez et al., Bioorganic & Medicinal Chemistry Letters 25 (2015), pp. 3420-3435).

Upregulation of CDK activity may be either due to loss of function mutations affecting genes encoding natural CDK inhibitors or the overexpression of CDK-activating cyclins.

CDK inhibitors known so far comprise natural substances, ATP-competitive and non-competitive synthetic compounds with a variety of chemical structures as well as peptides and peptidomimetics. They can be classified according to their specificity as pan-selective or selective for one single CDK and further by their mechanism of action (Peyressatre et al., Cancers 2015, 7, pp. 179-237).

Multiple myeloma (MM) represents a malignant proliferation of plasma cells derived from a single clone. The terms multiple myeloma and myeloma are commonly used interchangeably to refer to the same condition. The myeloma tumour, its products, and the host response to it result in a number of organ dysfunctions and symptoms of bone pain or fracture, bone lesions, hyperproteinaemia, renal failure, renal dysfunction, susceptibility to infection, immunodeficiency, anemia, hypocalcaemia, and occasionally clotting abnormalities, neurologic symptoms and vascular manifestations of hyperviscosity.

MM is considered to be incurable but is to a certain extent treatable. Remissions may be induced with steroids, chemotherapy, proteasome inhibitors, immunomodulatory drugs such as thalidomide or lenalidomide, and stem cell transplants. Radiation therapy is sometimes used to reduce pain from bone lesions (Raab M S, Podar K, Breitkreutz I, Richardson P G, Anderson K C (July 2009), "Multiple myeloma", Lancet 374 (9686): 324-39.) To date no effective long term treatment currently exists for MM.

The synthesis and biological activity of certain 3,4 disubstituted pyrazolo[3,4-d]pyrimidine-4-one nucleosides is disclosed in Journal of Medicinal Chemistry, 1984, vol. 27, 9, pp. 1119-1127. Unlike the compounds of the present invention, these compounds are unsubstituted at position 6. It is disclosed that some of the 3-substituted allopurinol nucleosides exhibited significant in vitro activity against Para 3 virus and were found to be potent inhibitors of growth of L1210 and P388 leukaemia cells in vitro. A broad spectrum of antiviral and antitumor activity and activity against *Leishmania tropica* in human macrophages in vitro has been attributed to these compounds.

The synthesis of pyrazolo[1,5-a]pyrimidine derivatives has been published without any reference to biological activity in the Journal of the Chinese Chemical Society (Taipei, Taiwan), 2009, vol. 56, 5, 1064-1071. These compounds are unsubstituted at the pyrazolo nitrogen at position 1.

U.S. Pat. No. 5,294,612 discloses 6-heterocyclyl pyrazolo [3,4-d]pyrimidin-4-one derivatives bearing an alkylamino-group at the 3-position inhibiting the enzymatic activity of phosphodisesterase (PDE) for the use of the treatment of cardiovascular disease. In these compounds, the heterocyclic ring is directly attached to position 6 without an alkylene bridge present in the compounds of the present invention.

6-substituted 1,5-dihydro-pyrazolo[3,4-d]pyrimidin-4-one derivative compounds exhibiting CDK inhibitory activity and their use for the treatment of disorders associated with excessive cell proliferation are, inter alia, described in WO 00/21926 A2, WO 02/067654 A2, WO 03/033499 A2, WO 03/063764 A2, WO 2004/092139 A2 and WO 2005/063765 A1.

WO 00/21926 A2 and WO 02/067654 A2 disclose a Markush-type formula wherein the 3-position at the pyrazolo ring may, inter alia, be an amino or a substituted amino group, however, they are focused on 6-substituted 1,5-dihydro-pyrazolo[3,4-d]pyrimidin-4-one derivatives bearing an alkyl substituent at the 3-position at the pyrazolo ring. The later filed applications WO 03/033499 A2, WO 03/063764 A2, WO 2004/092139 A2 and WO 2005/063765 A1 are specifically directed to 6-substituted 1,5-dihydro-pyrazolo[3,4-d]pyrimidin-4-one derivatives bearing an isopropyl group at the 3-position of the pyrazolo ring.

The novel 6-substituted 3-amino-1,5-dihydro-pyrazolo[3,4-d]pyrimidin-4-one derivatives of the present invention exhibit an unexpectedly increased potency over the 6-substituted 1,5-dihydro-pyrazolo[3,4-d]pyrimidin-4-one derivative compounds of the state of the art bearing an alkyl chain at the corresponding 3-position of the pyrazolo ring.

The modification of this alkyl chain to a substituted amino function has resulted in compounds exhibiting unexpected advantages over the prior compounds.

While CDK inhibitors have been in the focus of cancer therapy for quite some time and exhibited promising preclinical results and a number of compounds entered into clinical trials, so far only palbociclib, a CDK 4 and 6 inhibitor, has been approved for the treatment of advanced oestrogen receptor (ER)-positive/receptor 2 (HER2)-negative breast cancer in postmenopausal women.

Most clinical studies have been discontinued so far due to unfavourable pharmacological properties and low specificity for a certain cell cycle phase profile resulting, in generalised cytotoxicity with concomitant adverse effects such as QTc prolongation, fatigue, mucositis, cytopenia, severe diarrhoea, transaminase elevation, leukopenia, thrombocytopenia resulting in low therapeutic indices.

Thus, the challenge remains to develop compounds which inhibit CDK/cyclin hyperactivity with high efficiency, specificity and selectivity, whilst eliciting minimal toxic side effects and emergence of resistance over time.

SUMMARY OF THE INVENTION

Figure 1:
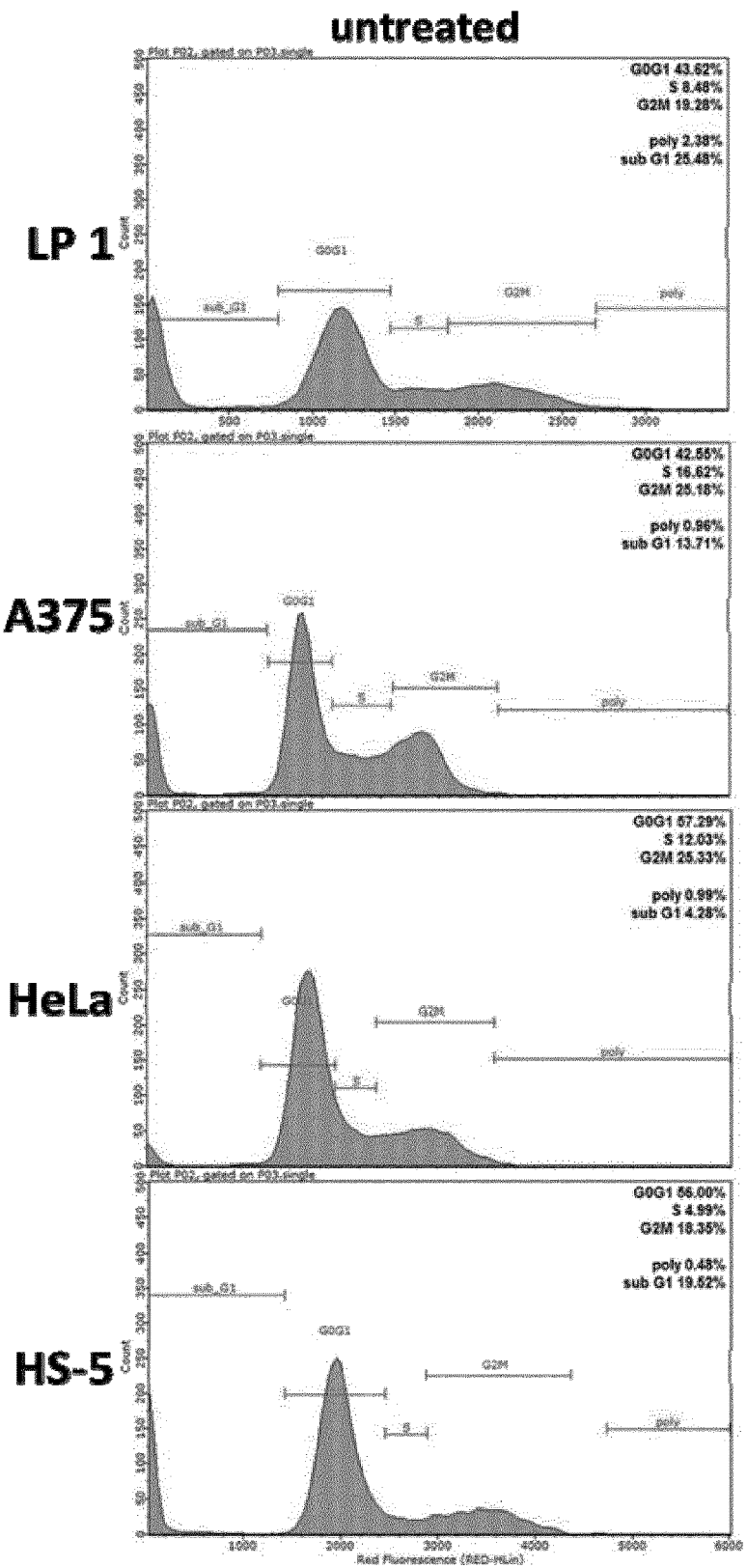
FIG. 1A depicts cell cycle analysis of three cancer cell lines (LP1: multiple myeloma cells; A375: melanoma cells; HeLa: cervix carcinoma cells) and control cells (HS-5: bone marrow stroma cells) after 12 and 24 h of treatment with 0.1 µM Otviciclib. All three tumor cell lines sho cell cycle defects and a progressive enrichment of the sub G1 group, a sign of fragmented nuclei in apoptosis, in a propidium iodide FACS analysis.
FIG. 1B provides a Western blot analysis of the respective cell lines with anti-PARP antibody after 24 h of treatment with 0.08 µM Otviciclib, which shows induction of PARP cleavage in tumor cell lines. O . . . Otviciclib; D . . . Dinaciclib (10 nM); B . . . Bortezomib (20 nM).
Figure 1:
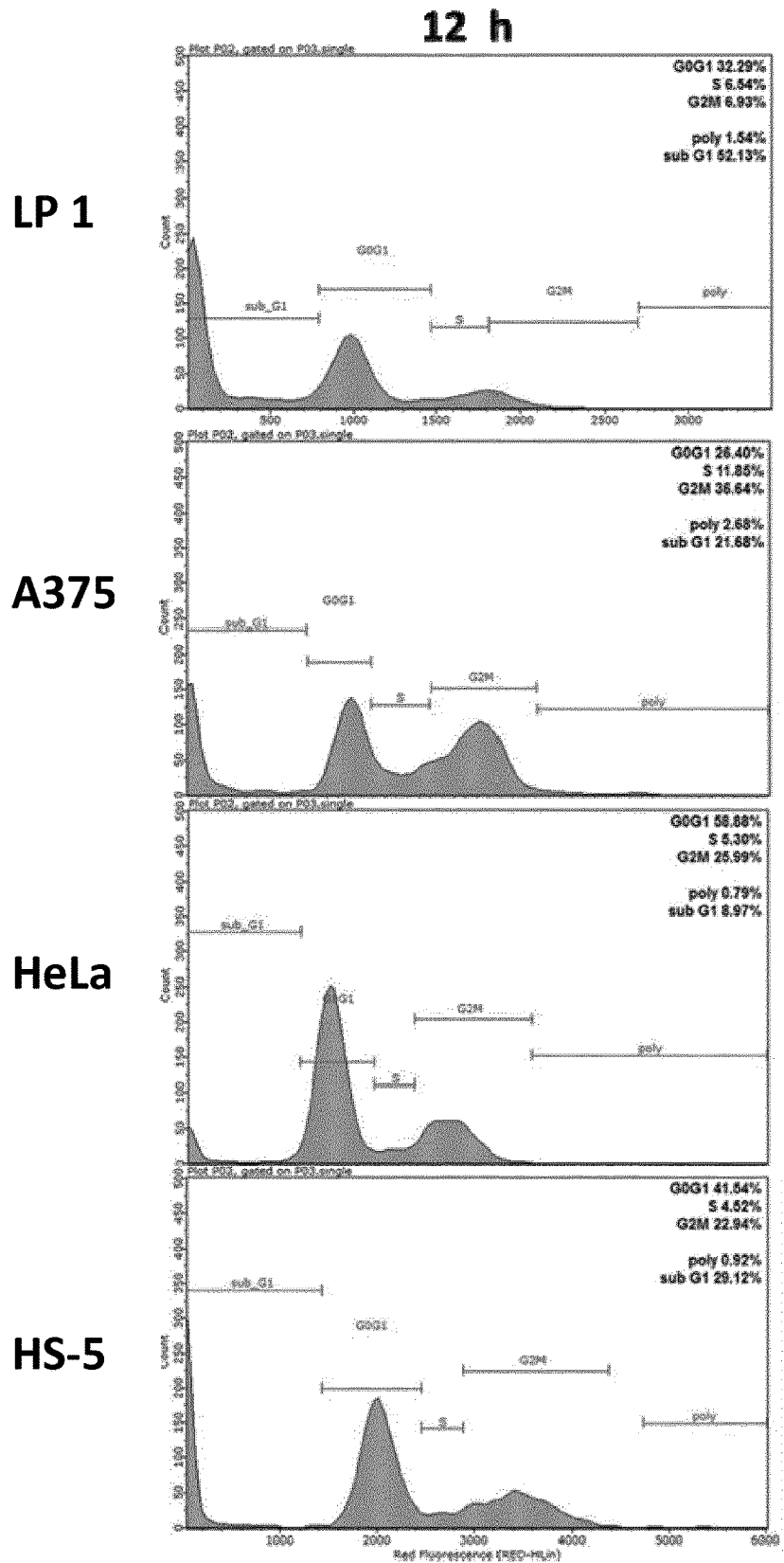
Figure 1:
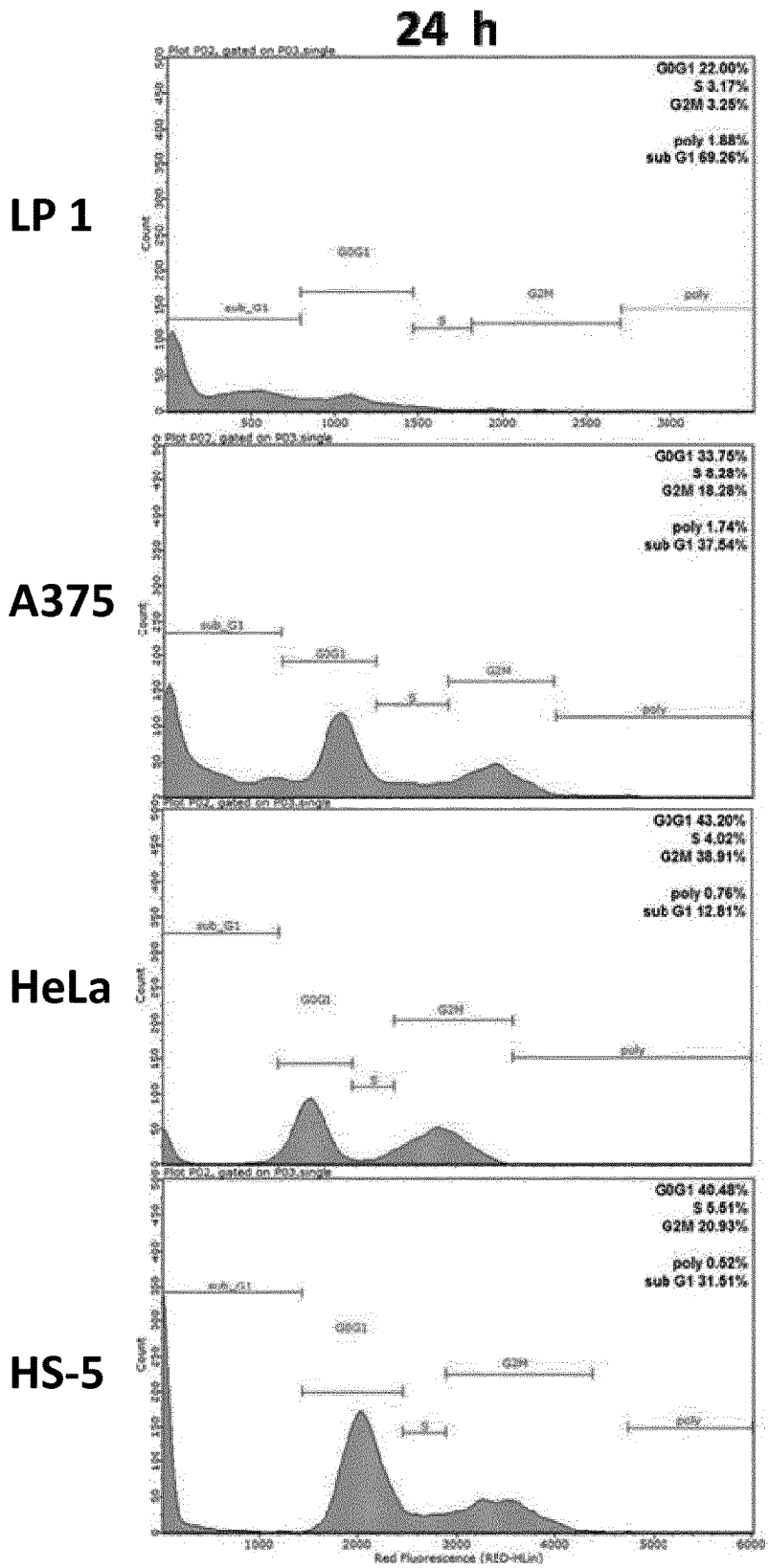

The present invention provides novel 6-substituted 3-amino-1,5-dihydro-pyrazolo[3,4-d]pyrimidin-4-ones having an optionally substituted amino substituent at the 3-position of the pyrazole ring or pharmaceutical acceptable salts, solvates or prodrugs thereof which are potent kinase inhibitors. While the inventors do not wish to be bound by any particular theory, the compounds of the present invention are believed to be particularly potent and selective cyclin dependent kinase (CDK) inhibitors.

The compounds of the present invention have the general formula (I) or are alternatively represented by the tautomer of formula (II):

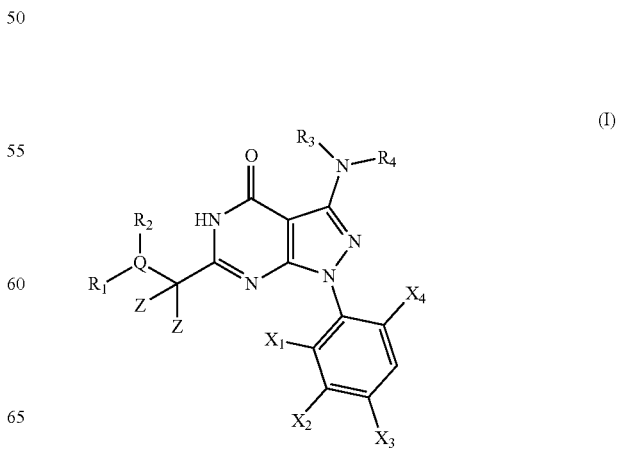

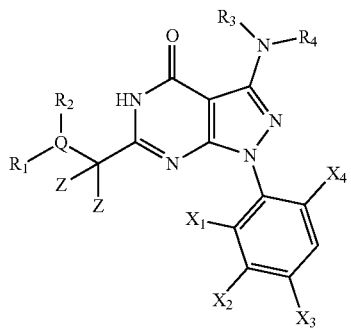

(I)

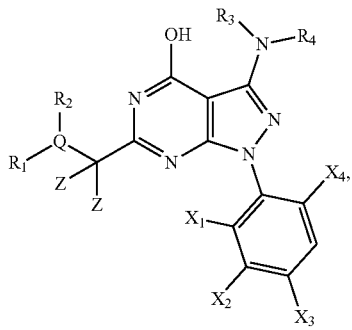

(II)

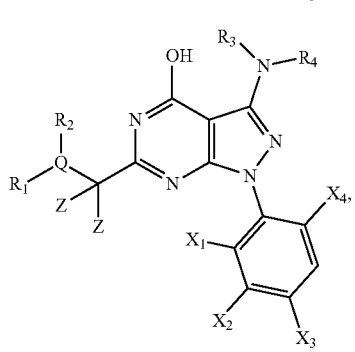

(II)

wherein $X_1$, $X_2$, $X_3$ and $X_4$, Z, Q, $R_1$, $R_2$, R3 and $R_4$ are defined as below or stereoisomers, pharmaceutically acceptable salts, solvates or prodrugs thereof.

Furthermore, the present invention provides pharmaceutical compositions comprising said 3-amino-pyrazolo[3,4-d]pyrimidin-4-ones and their use in the in the prophylaxis and/or treatment of cell proliferative diseases such as cancer; infectious diseases such as retroviral infectious diseases including HIV; pain such as inflammatory and neuropathic pain; asthma; diabetes; neurodegenerative diseases; cardiovascular diseases such as cardiac hypertrophy and inflammation.

In particular, the compounds and compositions according to the present invention may be used in the prophylaxis and/or treatment of cancer including solid tumours and haematological malignancies such as multiple myeloma and other proliferative diseases.

The compounds according to the present invention may be used alone or in combination with a further pharmaceutically active ingredient or therapy, such as radiotherapy.

In a further embodiment, the present invention provides processes for the synthesis of said novel 3-amino-pyrazolo[3,4-d]pyrimidin-4-ones and novel intermediates to be used in the processes of the present invention.

The problem underlying the present invention is to provide potent and selective kinase inhibitors which may be effectively and safely used for the prophylaxis and/or treatment of diseases which can be influenced by the inhibition of kinase activity, in particular of cyclin dependent kinases (CDKs), such as cancer and other proliferative diseases, in particular multiple myeloma.

As described herein, it has now been surprisingly found that the novel 6-substituted 3-amino-pyrazolo[3,4-d]pyrimidin-4-one derivatives of the present invention are potent inhibitors of the (cyclin dependent) kinase enzymes and/or variants thereof and as such may be useful in the prophylaxis and/or therapy of diseases which can be influenced by the inhibition of the kinase activity of cyclin dependent kinase (CDK) such as cancer and other proliferative diseases, in particular multiple myeloma.

DETAILED DESCRIPTION OF THE INVENTION

In a first embodiment the present invention provides novel compounds of the general formula (I) or its tautomer of formula (II):

wherein
$X_1$ is hydrogen, halogen or $C_1$-$C_6$-alkoxy (in particular $C_1$-$C_3$-alkoxy);
$X_2$ is hydrogen, or halogen;
$X_3$ is hydrogen, $SO_2NH_2$, $CONH_2$ or COOH;
$X_4$ is hydrogen, halogen or $C_1$-$C_6$-alkoxy (in particular $C_1$-$C_3$ alkoxy);
each z is independently selected from hydrogen and halogen;
Q is selected from a 5- or 6-membered aromatic ring which may contain one or more hetero atoms selected from N, O and S;
$R_1$ and $R_2$ are independently selected from hydrogen, halogen, $C_1$-$C_6$-alkyl (in particular $C_1$-$C_3$-alkyl), $C_1$-$C_6$-alkoxy (in particular $C_1$-$C_4$-alkoxy), OH, $NR_5R_6$ (in particular $NH_2$), AcONH, $MeSO_2NH$, $NO_2$, pyridine-3-yl, pyridine-4-yl, 1,2,4-triazole-1-methyl, pyrazole-1-methyl, 4-hydroxy-phenyl, 4-methoxy-phenyl, 3-ethylthio-phenyl, 4-chloro-phenyl, 2,4-difluoro-phenyl, 3-hydroxy-phenyl, 2-methoxy-pyridine-3-yl, 2-chloro-pyridine-4-yl,

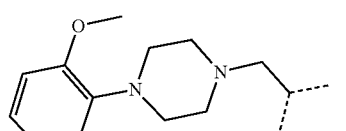

,

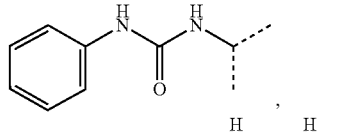

,

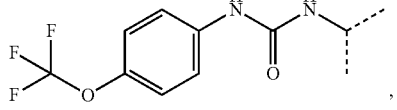

,

-continued

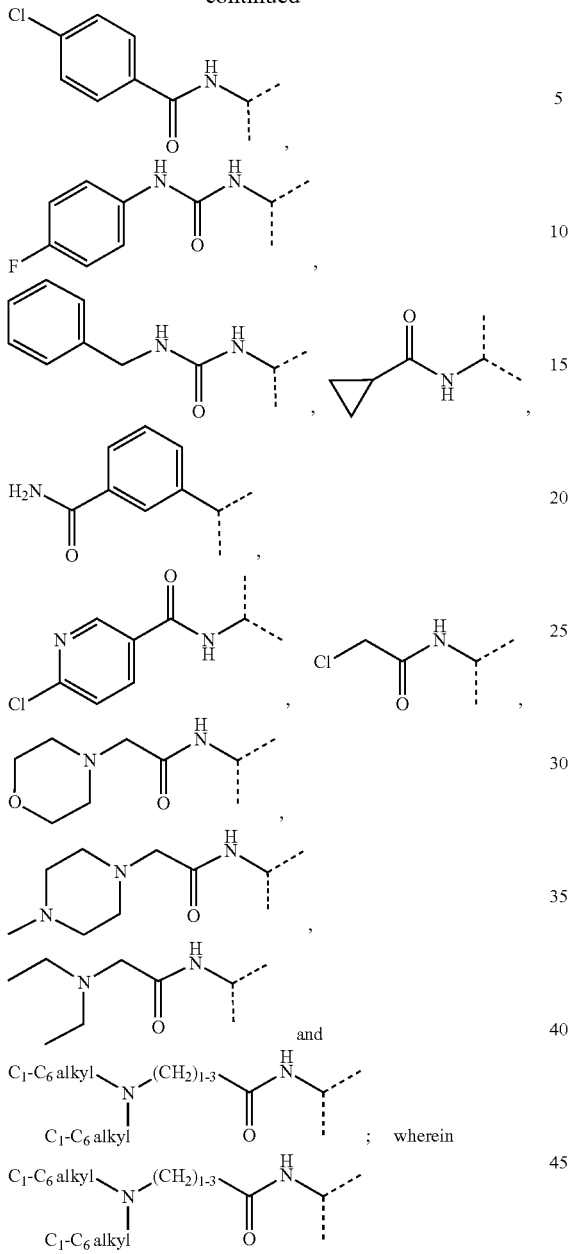

preferably means

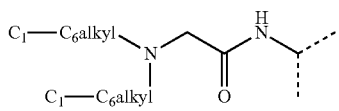

and even more preferably

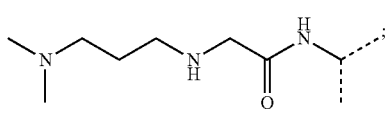

or $R_1$ and $R_2$ together may form ring condensed to the Q ring selected from:

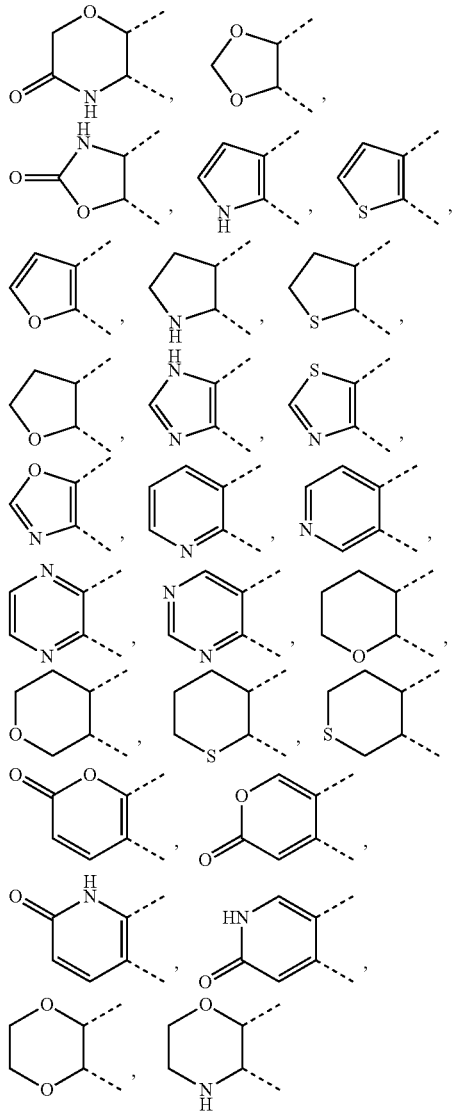

and $R_3$ and $R_4$ are independently selected from hydrogen and $C_1$-$C_6$ alkyl (in particular $C_1$-$C_3$ alkyl) optionally substituted by one or more halogen groups; wherein $C_1$-$C_6$, in particular $C_1$-$C_3$ alkyl is preferred; and $R_5$ and $R_6$ may be the same or different and are independently selected from hydrogen and $C_1$-$C_6$ alkyl;

or a stereoisomer thereof or a pharmaceutically acceptable salt, solvate or prodrug thereof.

In a preferred embodiment, the present invention provides novel compounds of formula (I) or (II), wherein $X_1$ is F, Cl, or MeO;
$X_2$ is hydrogen, or F;
$X_3$ is hydrogen, $SO_2NH_2$, or $CONH_2$;
$X_4$ is F, Cl, or MeO;
each z is independently selected from hydrogen and F;
Q is selected from phenyl, pyridine, thiophene, isoxazole and thiazole;
$R_1$ and $R_2$ are independently selected from hydrogen, F, Cl, Br, Me, MeO, BuO, OH, $NH_2$, AcONH, MeSO$_2$NH, NO$_2$, pyridine-3-yl, pyridine-4-yl, 1,2,4-triazole-1-methyl, pyrazole-1-methyl, 4-hydroxy-phenyl, 4-methoxy-phenyl, 3-ethylthio-phenyl, 4-chloro-phenyl, 2,4-difluoro-phenyl, 3-hydroxy-phenyl, 2-methoxy-pyridine-3-yl, 2-chloro-pyridine-4-yl,

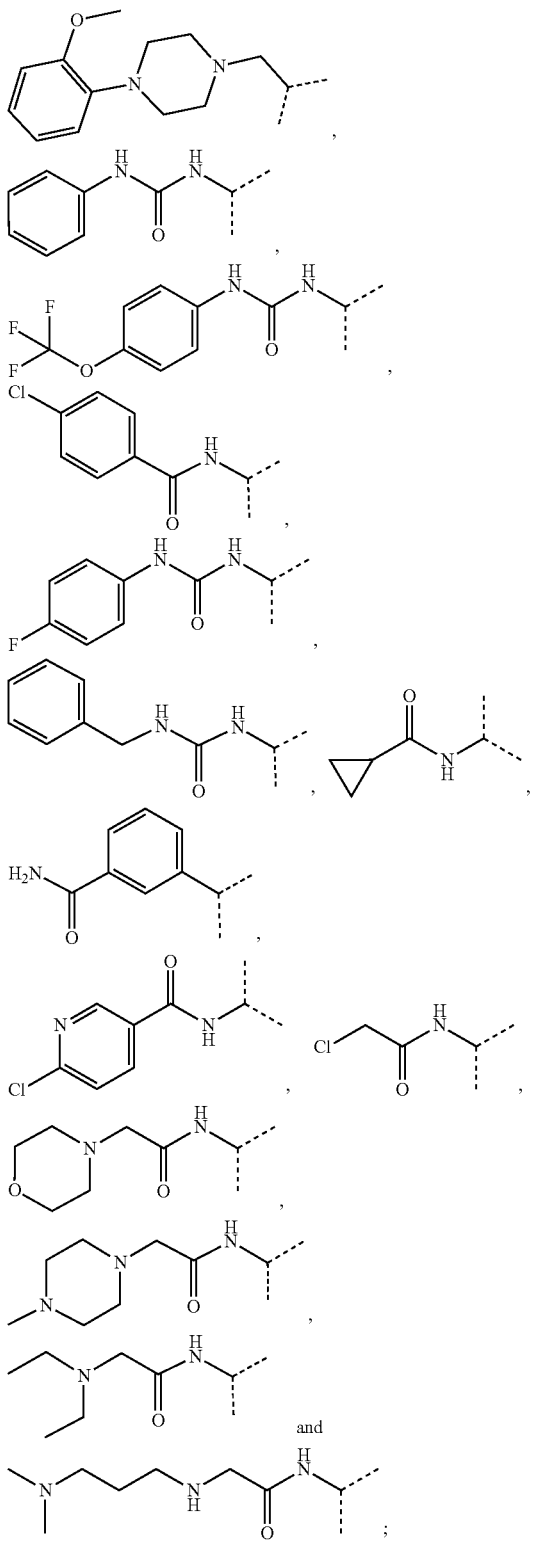

or R$_1$ and R$_2$ together may form ring condensed to the Q ring selected from:

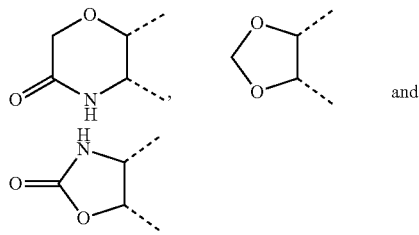

and

R$_3$ and R$_4$ are independently selected from C$_1$-C$_3$-alkyl (in particular both are CH$_3$);

or a stereoisomer thereof or a pharmaceutically acceptable salt, solvate or prodrug thereof.

In a more preferred embodiment, the present invention provides novel compounds of formula (I) or (II) as defined above, wherein X$_1$ is Cl, X$_2$ is hydrogen, X$_3$ is SO$_2$NH$_2$, X$_4$ is Cl each z is hydrogen, R$_3$ and R$_4$ are both CH$_3$, Q is selected from phenyl, thiazole and pyridine, and R$_1$ and R$_2$ are independently selected from hydrogen, F, Cl, Br, Me, MeO, BuO, OH, NH$_2$, AcONH, NO$_2$, pyridine-3-yl, 2-methoxy-pyridine-3-yl, pyridine-4-yl, 2-chloro-pyridine-4-yl, 4-hydroxy-phenyl, 4-methoxy-phenyl, 3-ethylthio-phenyl,

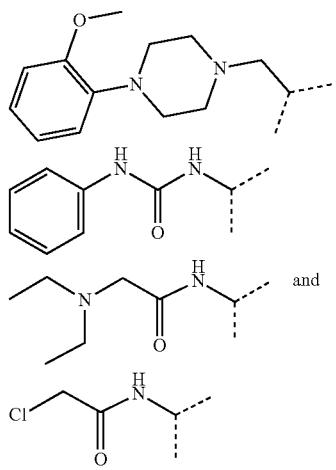

or R$_1$ and R$_2$ together may form ring condensed to the Q ring selected from:

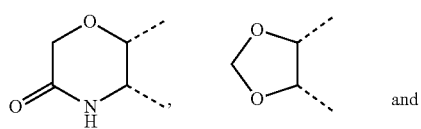

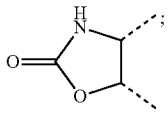

or a stereoisomer thereof or a pharmaceutically acceptable salt, solvate or prodrug thereof.

In a further preferred embodiment, the compound according to formula (I) or (II) is selected from:

4-[6-(4-amino-benzyl)-3-dimethylamino-4-oxo-4,5-dihydro-pyrazolo[3,4-d]pyrimidin-1-yl]-3,5-dichloro-benzenesulfonamide,
3,5-dichloro-4-[3-dimethylamino-6-(3-hydroxy-benzyl)-4-oxo-4,5-dihydro-pyrazolo[3,4-d]pyrimidin-1-yl]-benzamide,
1-(2,6-dichloro-phenyl)-3-dimethylamino-6-(3-hydroxy-benzyl)-1,5-dihydro-pyrazolo[3,4-d]pyrimidin-4-one,
6-[1-(2,6-dichloro-phenyl)-3-dimethylamino-4-oxo-4,5-dihydro-1H-pyrazolo[3,4-d]pyrimidin-6-ylmethyl]-4H-benzo[1,4]oxazin-3-one,
1-(2,6-dichloro-phenyl)-3-dimethylamino-6-(3-fluoro-benzyl)-1,5-dihydro-pyrazolo[3,4-d]pyrimidin-4-one,
6-(4-butoxy-benzyl)-1-(2,6-dichloro-phenyl)-3-dimethylamino-1,5-dihydro-pyrazolo[3,4-d]pyrimidin-4-one,
6-benzo[1,3]dioxol-5-ylmethyl-1-(2,6-dichloro-phenyl)-3-dimethylamino-1,5-dihydro-pyrazolo[3,4-d]pyrimidin-4-one,
6-(4-amino-benzyl)-1-(2,6-dichloro-phenyl)-3-dimethylamino-1,5-dihydro-pyrazolo[3,4-d]pyrimidin-4-one,
1-(2,6-dichloro-phenyl)-3-dimethylamino-6-(3-methoxy-benzyl)-1,5-dihydro-pyrazolo[3,4-d]pyrimidin-4-one,
6-(3,4-dichloro-benzyl)-1-(2,6-dichloro-phenyl)-3-dimethylamino-1,5-dihydro-pyrazolo[3,4-d]pyrimidin-4-one,
6-(3-bromo-4-hydroxy-benzyl)-1-(2,6-dichloro-phenyl)-3-dimethylamino-1,5-dihydro-pyrazolo[3,4-d]pyrimidin-4-one,
1-(2,6-dichloro-phenyl)-3-dimethylamino-6-(3-methyl-benzyl)-1,5-dihydro-pyrazolo[3,4-d]pyrimidin-4-one,
3,5-dichloro-4-[3-dimethylamino-6-(3-hydroxy-benzyl)-4-oxo-4,5-dihydro-pyrazolo[3,4-d]pyrimidin-1-yl]-benzenesulfonamide,
3,5-dichloro-4-[3-dimethylamino-4-oxo-6-(4-[1,2,4]triazol-1-ylmethyl-benzyl)-4,5-dihydro-pyrazolo[3,4-d]pyrimidin-1-yl]-benzenesulfonamide,
N-{3-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-acetamide,
3,5-dichloro-4-[3-dimethylamino-4-oxo-6-(3-oxo-3,4-dihydro-2H-benzo[1,4]oxazin-6-ylmethyl)-4,5-dihydro-pyrazolo[3,4-d]pyrimidin-1-yl]-benzenesulfonamide,
3,5-dichloro-4-[3-dimethylamino-4-oxo-6-(4-pyrazol-1-ylmethyl-benzyl)-4,5-dihydro-pyrazolo[3,4-d]pyrimidin-1-yl]-benzenesulfonamide,
3,5-dichloro-4-(3-dimethylamino-6-{4-[4-(2-methoxy-phenyl)-piperazin-1-ylmethyl]-benzyl}-4-oxo-4,5-dihydro-pyrazolo[3,4-d]pyrimidin-1-yl)-benzenesulfonamide,
3,5-dichloro-4-[3-dimethylamino-6-(3-fluoro-benzyl)-4-oxo-4,5-dihydro-pyrazolo[3,4-d]pyrimidin-1-yl]-benzenesulfonamide,
1-(2,6-dichloro-phenyl)-3-dimethylamino-6-pyridin-3-ylmethyl-1,5-dihydro-pyrazolo[3,4-d]pyrimidin-4-one,
6-(5-bromo-pyridin-3-ylmethyl)-1-(2,6-dichloro-phenyl)-3-dimethylamino-1,5-dihydro-pyrazolo[3,4-d]pyrimidin-4-one,
4-[6-(4-butoxy-benzyl)-3-dimethylamino-4-oxo-4,5-dihydro-pyrazolo[3,4-d]pyrimidin-1-yl]-3,5-dichloro-benzenesulfonamide,
4-(6-benzo[1,3]dioxol-5-ylmethyl-3-dimethylamino-4-oxo-4,5-dihydro-pyrazolo[3,4-d]pyrimidin-1-yl)-3,5-dichloro-benzenesulfonamide,
3,5-dichloro-4-[6-(3,4-dichloro-benzyl)-3-dimethylamino-4-oxo-4,5-dihydro-pyrazolo[3,4-d]pyrimidin-1-yl]-benzenesulfonamide,
6-benzo[1,3]dioxol-5-ylmethyl-1-(2,3-difluoro-6-methoxy-phenyl)-3-dimethylamino-1,5-dihydro-pyrazolo[3,4-d]pyrimidin-4-one,
4-[6-(5-bromo-pyridin-3-ylmethyl)-3-dimethylamino-4-oxo-4,5-dihydro-pyrazolo[3,4-d]pyrimidin-1-yl]-3,5-dichloro-benzenesulfonamide,
3,5-dichloro-4-[3-dimethylamino-6-(4-methoxy-benzyl)-4-oxo-4,5-dihydro-pyrazolo[3,4-d]pyrimidin-1-yl]-benzenesulfonamide,
3,5-dichloro-4-(3-dimethylamino-4-oxo-6-thiophen-2-ylmethyl-4,5-dihydro-pyrazolo[3,4-d]pyrimidin-1-yl)-benzenesulfonamide,
3,5-dichloro-4-[3-dimethylamino-4-oxo-6-(2-oxo-2,3-dihydro-benzooxazol-5-ylmethyl)-4,5-dihydro-pyrazolo[3,4-d]pyrimidin-1-yl]-benzenesulfonamide,
1-(2,3-difluoro-6-methoxy-phenyl)-3-dimethylamino-6-thiophen-2-ylmethyl-1,5-dihydro-pyrazolo[3,4-d]pyrimidin-4-one,
4-[6-(3-bromo-4-hydroxy-benzyl)-3-dimethylamino-4-oxo-4,5-dihydro-pyrazolo[3,4-d]pyrimidin-1-yl]-3,5-dichloro-benzenesulfonamide,
4-[6-(4-bromo-benzyl)-3-dimethylamino-4-oxo-4,5-dihydro-pyrazolo[3,4-d]pyrimidin-1-yl]-3,5-dichloro-benzenesulfonamide,
3,5-dichloro-4-[3-dimethylamino-6-(4-methoxy-3-nitrobenzyl)-4-oxo-4,5-dihydro-pyrazolo[3,4-d]pyrimidin-1-yl]-benzenesulfonamide,
3,5-dichloro-4-[3-dimethylamino-6-(3,4-dimethyl-benzyl)-4-oxo-4,5-dihydro-pyrazolo[3,4-d]pyrimidin-1-yl]-benzenesulfonamide,
1-(2,6-dichloro-phenyl)-3-dimethylamino-6-thiophen-2-ylmethyl-1,5-dihydro-pyrazolo[3,4-d]pyrimidin-4-one,
1-(2,6-dichloro-phenyl)-3-dimethylamino-6-(3-methyl-isoxazol-5-ylmethyl)-1,5-dihydro-pyrazolo[3,4-d]pyrimidin-4-one,
3,5-dichloro-4-[3-dimethylamino-6-(4-fluoro-benzyl)-4-oxo-4,5-dihydro-pyrazolo[3,4-d]pyrimidin-1-yl]-benzenesulfonamide,
3,5-dichloro-4-[3-dimethylamino-6-(2-methoxy-pyridin-4-ylmethyl)-4-oxo-4,5-dihydro-pyrazolo[3,4-d]pyrimidin-1-yl]-benzenesulfonamide,
3,5-dichloro-4-[3-dimethylamino-6-(5-methoxy-pyridin-3-ylmethyl)-4-oxo-4,5-dihydro-pyrazolo[3,4-d]pyrimidin-1-yl]-benzenesulfonamide,
4-[6-(3-amino-4-fluoro-benzyl)-3-dimethylamino-4-oxo-4,5-dihydro-pyrazolo[3,4-d]pyrimidin-1-yl]-3,5-dichloro-benzenesulfonamide,
4-[6-(2-amino-thiazol-4-ylmethyl)-3-dimethylamino-4-oxo-4,5-dihydro-pyrazolo[3,4-d]pyrimidin-1-yl]-3,5-dichloro-benzenesulfonamide,
3,5-dichloro-4-[3-dimethylamino-6-(3-methyl-benzyl)-4-oxo-4,5-dihydro-pyrazolo[3,4-d]pyrimidin-1-yl]-benzenesulfonamide,
4-[6-(3-amino-4-methoxy-benzyl)-3-dimethylamino-4-oxo-4,5-dihydro-pyrazolo[3,4-d]pyrimidin-1-yl]-3,5-dichloro-benzenesulfonamide, 1-(2,3-difluoro-6-methoxy-phenyl)-3-dimethylamino-6-(3-methyl-benzyl)-1,5-dihydro-pyrazolo[3,4-d]pyrimidin-4-one, 3,5-dichloro-4-[3-dimethylamino-6-(4-methyl-thiazol-2-ylmethyl)-4-oxo-4,5-dihydro-pyrazolo[3,4-d]pyrimidin-1-yl]-benzenesulfonamide, 1-(2,6-dichloro-phenyl)-3-dimethylamino-6-(4-methyl-thiazol-2-ylmethyl)-1,5-dihydro-pyrazolo[3,4-d]pyrimidin-4-one, 3,5-dichloro-4-{6-[difluoro-(4-methoxy-phenyl)-methyl]-3-dimethylamino-4-oxo-4,5-dihydro-pyrazolo[3,4-d]pyrimidin-1-yl}-benzenesulfonamide, 3,5-dichloro-4-{6-[difluoro-(3-fluoro-phenyl)-methyl]-3-dimethylamino-4-oxo-4,5-dihydro-pyrazolo[3,4-d]pyrimidin-1-yl}-benzenesulfonamide, 1-(2,3-difluoro-6-methoxy-phenyl)-3-dimethylamino-6-(4-methyl-thiazol-2-ylmethyl)-1,5-dihydro-pyrazolo[3,4-d]pyrimidin-4-one, 1-(2,6-dichloro-phenyl)-3-dimethylamino-6-(5-methoxy-pyridin-3-ylmethyl)-1,5-dihydro-pyrazolo[3,4-d]pyrimidin-4-one, 3,5-dichloro-4-[6-(3,4-dimethoxy-benzyl)-3-dimethylamino-4-oxo-4,5-dihydro-pyrazolo[3,4-d]pyrimidin-1-yl]-benzenesulfonamide, 3,5-dichloro-4-{3-dimethylamino-4-oxo-6-[4-(3-phenyl-ureido)-benzyl]-4,5-dihydro-pyrazolo[3,4-d]pyrimidin-1-yl}-benzenesulfonamide, 3,5-dichloro-4-[3-dimethylamino-6-(4-methanesulfonylamino-benzyl)-4-oxo-4,5-dihydro-pyrazolo[3,4-d]pyrimidin-1-yl]-benzenesulfonamide, N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-acetamide, 3,5-dichloro-4-[3-dimethylamino-6-(3-methanesulfonylamino-benzyl)-4-oxo-4,5-dihydro-pyrazolo[3,4-d]pyrimidin-1-yl]-benzenesulfonamide, 4-{6-[3-(3-benzyl-ureido)-benzyl]-3-dimethylamino-4-oxo-4,5-dihydro-pyrazolo[3,4-d]pyrimidin-1-yl}-3,5-dichloro-benzenesulfonamide, 4-{6-[4-(3-Benzyl-ureido)-benzyl]-3-dimethylamino-4-oxo-4,5-dihydro-pyrazolo[3,4-d]pyrimidin-1-yl}-3,5-dichloro-benzenesulfonamide, 1-(2,3-difluoro-6-methoxy-phenyl)-3-dimethylamino-6-(4-pyridin-3-yl-benzyl)-1,5-dihydro-pyrazolo[3,4-d]pyrimidin-4-one, 3,5-dichloro-4-[3-dimethylamino-4-oxo-6-(4-pyridin-3-yl-benzyl)-4,5-dihydro-pyrazolo[3,4-d]pyrimidin-1-yl]-benzenesulfonamide, 3,5-dichloro-4-[3-dimethylamino-6-(2-hydroxy-pyridin-4-ylmethyl)-4-oxo-4,5-dihydro-pyrazolo[3,4-d]pyrimidin-1-yl]-benzenesulfonamide, 3,5-dichloro-4-[3-dimethylamino-6-(5-hydroxy-pyridin-3-ylmethyl)-4-oxo-4,5-dihydro-pyrazolo[3,4-d]pyrimidin-1-yl]-benzenesulfonamide, N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-fluoro-phenyl}-acetamide, N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-thiazol-2-yl}-acetamide, 3,5-dichloro-4-{3-dimethylamino-6-[4-(2-methoxy-pyridin-3-yl)-benzyl]-4-oxo-4,5-dihydro-pyrazolo[3,4-d]pyrimidin-1-yl}-benzenesulfonamide, 3,5-dichloro-4-{6-[4-(2-chloro-pyridin-4-yl)-benzyl]-3-dimethylamino-4-oxo-4,5-dihydro-pyrazolo[3,4-d]pyrimidin-1-yl}-benzenesulfonamide, 4-chloro-N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-thiazol-2-yl}-benzamide, 4-{6-[3-(3-benzyl-ureido)-4-methoxy-benzyl]-3-dimethylamino-4-oxo-4,5-dihydro-pyrazolo[3,4-d]pyrimidin-1-yl}-3,5-dichloro-benzenesulfonamide, 3,5-dichloro-4-(3-dimethylamino-6-{3-[3-(4-fluoro-phenyl)-ureido]-4-methoxy-benzyl}-4-oxo-4,5-dihydro-pyrazolo[3,4-d]pyrimidin-1-yl)-benzenesulfonamide, N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-acetamide, 3,5-dichloro-4-[3-dimethylamino-4-oxo-6-(4-pyridin-4-yl-benzyl)-4,5-dihydro-pyrazolo[3,4-d]pyrimidin-1-yl]-benzenesulfonamide, 3,5-dichloro-4-[3-dimethylamino-6-(4'-methoxy-biphenyl-4-ylmethyl)-4-oxo-4,5-dihydro-pyrazolo[3,4-d]pyrimidin-1-yl]-benzenesulfonamide, 2-chloro-N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-acetamide, N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-2-morpholin-4-yl-acetamide, 3,5-dichloro-4-[3-dimethylamino-6-(3'-ethylsulfanyl-biphenyl-4-ylmethyl)-4-oxo-4,5-dihydro-pyrazolo[3,4-d]pyrimidin-1-yl]-benzenesulfonamide, 3,5-dichloro-4-[3-dimethylamino-6-(4'-hydroxy-biphenyl-4-ylmethyl)-4-oxo-4,5-dihydro-pyrazolo[3,4-d]pyrimidin-1-yl]-benzenesulfonamide, 3,5-dichloro-4-(3-dimethylamino-6-{4-methoxy-3-[3-(4-trifluoromethoxy-phenyl)-ureido]-benzyl}-4-oxo-4,5-dihydro-pyrazolo[3,4-d]pyrimidin-1-yl)-benzenesulfonamide, N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-2-morpholin-4-yl-acetamide, N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-2-diethylamino-acetamide, N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-2-(4-methyl-piperazin-1-yl)-acetamide, cyclopropanecarboxylic acid {5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-amide, 4'-[1-(2,6-dichloro-4-sulfamoyl-phenyl)-3-dimethylamino-4-oxo-4,5-dihydro-1H-pyrazolo[3,4-d]pyrimidin-6-ylmethyl]-biphenyl-3-carboxylic acid amide, 3,5-dichloro-4-[6-(4'-chloro-biphenyl-4-ylmethyl)-3-dimethylamino-4-oxo-4,5-dihydro-pyrazolo[3,4-d]pyrimidin-1-yl]-benzenesulfonamide 3,5-dichloro-4-[6-(2',4'-difluoro-biphenyl-4-ylmethyl)-3-dimethylamino-4-oxo-4,5-dihydro-pyrazolo[3,4-d]pyrimidin-1-yl]-benzenesulfonamide, 3,5-dichloro-4-[3-dimethylamino-6-(3'-hydroxy-biphenyl-4-ylmethyl)-4-oxo-4,5-dihydro-pyrazolo[3,4-d]pyrimidin-1-yl]-benzenesulfonamide, 6-chloro-N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-nicotinamide, N-{4-[1-(2,6-dichloro-4-sulfamoyl-phenyl)-3-dimethyl-amino-4-oxo-4,5-dihydro-1H-pyrazolo[3,4-d]pyrimidin-6-ylmethyl]-phenyl}-2-(3-dimethylamino-propylamino)-acetamide, 3-benzyloxy-cyclobutanecarboxylic acid {4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-amide, N-{4-[1-(2,6-dichloro-4-sulfamoyl-phenyl)-3-dimethyl-amino-4-oxo-4,5-dihydro-1H-pyrazolo[3,4-d]pyrimidin-6-ylmethyl]-phenyl}-2-dimethylamino-acetamide, 2-diethylamino-N-{4-[1-(2,6-difluoro-4-sulfamoyl-phenyl)-3-dimethylamino-4-oxo-4,5-dihydro-1H-pyrazolo[3,4-d]pyrimidin-6-ylmethyl]-phenyl}-acetamide, 4-{6-[3-amino-4-(1,4-dioxa-8-aza-spiro[4.5]dec-8-yl)-benzyl]-3-dimethylamino-4-oxo-4,5-dihydro-pyrazolo[3,4-d]pyrimidin-1-yl}-3,5-dichloro-benzenesulfonamide and 4-[6-(4-butoxy-benzyl)-3-dimethylamino-4-oxo-4,5-dihydro-pyrazolo[3,4-d]pyrimidin-1-yl]-3,5-dichloro-benzoic acid, or pharmaceutically acceptable salts, solvates or prodrugs thereof.

In a(n even) more preferred embodiment, the novel compound of the invention is selected from:

3-Benzyloxy-cyclobutanecarboxylic acid {4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-amide, 3,5-dichloro-4-{3-dimethylamino-4-oxo-6-[4-(3-phenyl-ureido)-benzyl]-4,5-dihydro-pyrazolo[3,4-d]pyrimidin-1-yl}-benzenesulfonamide, N-{4-[1-(2,6-dichloro-4-sulfamoyl-phenyl)-3-dimethyl-amino-4-oxo-4,5-dihydro-1H-pyrazolo[3,4-d]pyrimidin-6-ylmethyl]-phenyl}-acetamide, 4-[6-(4-amino-benzyl)-3-dimethylamino-4-oxo-4,5-dihydro-pyrazolo[3,4-d]pyrimidin-1-yl]-3,5-dichloro-benzenesulfonamide, 4-{6-[4-(3-benzyl-ureido)-benzyl]-3-dimethylamino-4-oxo-4,5-dihydro-pyrazolo[3,4-d]pyrimidin-1-yl}-3,5-dichloro-benzenesulfonamide, 3,5-dichloro-4-[3-dimethylamino-4-oxo-6-(3-oxo-3,4-dihydro-2H-benzo[1,4]oxazin-6-ylmethyl)-4,5-dihydro-pyrazolo[3,4-d]pyrimidin-1-yl]-benzenesulfonamide, 3,5-dichloro-4-(3-dimethylamino-6-{4-[4-(2-methoxy-phenyl)-piperazin-1-ylmethyl]-benzyl}-4-oxo-4,5-dihydro-pyrazolo[3,4-d]pyrimidin-1-yl)-benzenesulfonamide, 3,5-dichloro-4-[3-dimethylamino-6-(3-fluoro-benzyl)-4-oxo-4,5-dihydro-pyrazolo[3,4-d]pyrimidin-1-yl]-benzenesulfonamide, 4-[6-(4-butoxy-benzyl)-3-dimethylamino-4-oxo-4,5-dihydro-pyrazolo[3,4-d]pyrimidin-1-yl]-3,5-dichloro-benzenesulfonamide, 4-(6-benzo[1,3]dioxol-5-ylmethyl-3-dimethylamino-4-oxo-4,5-dihydro-pyrazolo[3,4-d]pyrimidin-1-yl)-3,5-dichloro-benzenesulfonamide, 3,5-dichloro-4-[6-(3,4-dichloro-benzyl)-3-dimethylamino-4-oxo-4,5-dihydro-pyrazolo[3,4-d]pyrimidin-1-yl]-benzenesulfonamide, 3,5-dichloro-4-[3-dimethylamino-6-(4-methoxy-benzyl)-4-oxo-4,5-dihydro-pyrazolo[3,4-d]pyrimidin-1-yl]-benzenesulfonamide, 4-[6-(3-bromo-4-hydroxy-benzyl)-3-dimethylamino-4-oxo-4,5-dihydro-pyrazolo[3,4-d]pyrimidin-1-yl]-3,5-dichloro-benzenesulfonamide, 4-[6-(4-bromo-benzyl)-3-dimethylamino-4-oxo-4,5-dihydro-pyrazolo[3,4-d]pyrimidin-1-yl]-3,5-dichloro-benzenesulfonamide, 3,5-dichloro-4-[3-dimethylamino-4-oxo-6-(4-pyridin-3-yl-benzyl)-4,5-dihydro-pyrazolo[3,4-d]pyrimidin-1-yl]-benzenesulfonamide, 3,5-dichloro-4-[3-dimethylamino-6-(4-methoxy-3-nitro-benzyl)-4-oxo-4,5-dihydro-pyrazolo[3,4-d]pyrimidin-1-yl]-benzenesulfonamide, 3,5-dichloro-4-[3-dimethylamino-6-(3,4-dimethyl-benzyl)-4-oxo-4,5-dihydro-pyrazolo[3,4-d]pyrimidin-1-yl]-benzenesulfonamide, 3,5-dichloro-4-[3-dimethylamino-6-(4-fluoro-benzyl)-4-oxo-4,5-dihydro-pyrazolo[3,4-d]pyrimidin-1-yl]-benzenesulfonamide, 3,5-dichloro-4-[3-dimethylamino-6-(2-methoxy-pyridin-4-ylmethyl)-4-oxo-4,5-dihydro-pyrazolo[3,4-d]pyrimidin-1-yl]-benzenesulfonamide, 3,5-dichloro-4-[3-dimethylamino-6-(5-methoxy-pyridin-3-ylmethyl)-4-oxo-4,5-dihydro-pyrazolo[3,4-d]pyrimidin-1-yl]-benzenesulfonamide, 4-[6-(3-amino-4-fluoro-benzyl)-3-dimethylamino-4-oxo-4,5-dihydro-pyrazolo[3,4-d]pyrimidin-1-yl]-3,5-dichloro-benzenesulfonamide, 3,5-dichloro-4-[3-dimethylamino-6-(3-methyl-benzyl)-4-oxo-4,5-dihydro-pyrazolo[3,4-d]pyrimidin-1-yl]-benzenesulfonamide, 3,5-dichloro-4-{3-dimethylamino-6-[4-(2-methoxy-pyridin-3-yl)-benzyl]-4-oxo-4,5-dihydro-pyrazolo[3,4-d]pyrimidin-1-yl}-benzenesulfonamide, 3,5-dichloro-4-{6-[4-(2-chloro-pyridin-4-yl)-benzyl]-3-dimethylamino-4-oxo-4,5-dihydro-pyrazolo[3,4-d]pyrimidin-1-yl}-benzenesulfonamide, 4-[6-(3-amino-4-methoxy-benzyl)-3-dimethylamino-4-oxo-4,5-dihydro-pyrazolo[3,4-d]pyrimidin-1-yl]-3,5-dichloro-benzenesulfonamide, 3,5-dichloro-4-[3-dimethylamino-4-oxo-6-(4-pyridin-4-yl-benzyl)-4,5-dihydro-pyrazolo[3,4-d]pyrimidin-1-yl]-benzenesulfonamide, 3,5-dichloro-4-[3-dimethylamino-6-(4'-methoxy-biphenyl-4-ylmethyl)-4-oxo-4,5-dihydro-pyrazolo[3,4-d]pyrimidin-1-yl]-benzenesulfonamide, 2-chloro-N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-acetamide, 3,5-dichloro-4-[3-dimethylamino-6-(3'-ethylsulfanyl-biphenyl-4-ylmethyl)-4-oxo-4,5-dihydro-pyrazolo[3,4-d]pyrimidin-1-yl]-benzenesulfonamide, 3,5-dichloro-4-[3-dimethylamino-6-(4'-hydroxy-biphenyl-4-ylmethyl)-4-oxo-4,5-dihydro-pyrazolo[3,4-d]pyrimidin-1-yl]-benzenesulfonamide, and N-{4-[1-(2,6-dichloro-4-sulfamoyl-phenyl)-3-dimethyl-amino-4-oxo-4,5-dihydro-1H-pyrazolo[3,4-d]pyrimidin-6-ylmethyl]-phenyl}-2-diethylamino-acetamide or pharmaceutically acceptable salts, solvates or prodrugs thereof.

N-{4-[1-(2,6-Dichloro-4-sulfamoyl-phenyl)-3-dimethyl-amino-4-oxo-4,5-dihydro-1H-pyrazolo[3,4-d]pyrimidin-6-ylmethyl]-phenyl}-2-diethylamino-acetamide is particularly preferred.

In another embodiment, the present invention provides a novel pharmaceutical composition comprising (a therapeutically effective amount of) a compound of formula (I) or (II) or a pharmaceutically acceptable salt, solvate or prodrug thereof optionally in admixture with at least one pharmaceutically acceptable excipient.

A pharmaceutical composition comprising N-{4-[1-(2,6-Dichloro-4-sulfamoyl-phenyl)-3-dimethylamino-4-oxo-4,5- dihydro-1H-pyrazolo[3,4-d]pyrimidin-6-ylmethyl]-phenyl}-2-diethylamino-acetamide (compound 86), Otviciclib, is particularly preferred.

In yet another embodiment, the pharmaceutical composition according to the present invention may be administered in combination with at least one compound selected from the group of proteasome inhibitors, cereblon-modulators, DNA damage inducers, MAPK pathway inhibitors, PI3K/Akt pathway inhibitors, TNF pathway agonists, BH3 mimetic drugs, BET domain inhibitors, inhibitors of poly (ADP-ribose) polymerase (PARP) and/or radiotherapy.

The present invention also pertains to the compounds or the pharmaceutical compositions provided herein, wherein the corresponding compound or pharmaceutical composition is to be administered by any one of: an oral route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; or ophthalmic route, including by intravitreal, or intracameral route. Particularly preferred routes of administration are parenteral administrations like, e.g., intravenous and intraperitoneal (during hyperthermic chemoperfusion) and oral administration, whereby the oral administration is particularly preferred.

In another embodiment, the present invention provides a pharmaceutical composition comprising at least one of compound of the present invention or a compound according to the present invention for use in the prevention or treatment of a proliferative disease.

In a preferred embodiment of the invention, the proliferative disease is cancer.

According to the present invention, said cancer may be selected from solid tumours, haematological malignancies, tumours of mesenchymal origin, tumours of the central and peripheral nervous system, melanoma, seminoma, teratocarcinoma, osteosarcoma, xeroderma pigmentosum, keratoacanthoma, thyroid follicular cancer, neuroendocrine tumours and Kaposi's sarcoma.

In one embodiment, the solid tumour may be selected from liver cancer, stomach cancer, colon cancer, breast cancer, pancreatic cancer, prostate cancer, skin cancer, renal cancer, bone cancer, thyroid cancer, skin cancer (including squamous cell carcinoma), oesophageal cancer, kidney cancer, bladder cancer, gall cancer, cervical cancer, ovarian cancer, lung cancer (including bronchial, small and non-small-cell lung cancer), gastric cancer, and head and neck cancer.

In a preferred embodiment, the solid tumour is selected from colon cancer, pancreatic cancer and lung cancer (including bronchial, small and non-small-cell lung cancer).

In a further embodiment, the haematological malignancy is selected from leukaemia including acute myelogenous leukaemia (AML), acute lymphoblastic leukaemia (ALL), acute lymphocytic leukaemia, acute leukaemia, acute promyelocytic leukaemia, chronic granulocytic leukaemia (CGL), chronic leukaemia, chronic lymphocytic leukaemia (CLL), chronic myelogenous leukaemia (CML), chronic myelomonocytic leukaemia, common-type acute lymphoblastic leukaemia, eosinophilic leukaemia, erythroleukaemia, extranodal lymphoma, follicular lymphoma, hairy cell leukaemia, monocytic leukaemia and prolymphocytic leukaemia;

lymphoma, including B cell lymphomas, Burkitt lymphoma, cutaneous T cell lymphoma, high-grade lymphoma, Hodgkin's lymphoma, Non-Hodgkin's lymphoma, low-grade lymphoma, lymphoblastic lymphoma, mantle cell lymphoma, marginal zone lymphoma, mucosa-associated lymphoid tissue (MALT) lymphomas, T cell lymphomas, peripheral T cell lymphoma and hairy cell lymphoma; multiple myeloma; extramedullary myeloma; essential thrombocythaemia; granulocytic sarcoma and tumours of myeloid lineage, including acute and chronic myelogenous leukaemia, myelodysplastic syndrome, and promyelocytic leukaemia.

In yet further embodiments, the tumour of mesenchymal origin may be selected from fibrosarcoma and rhabdomyosarcoma and the tumour of the central and peripheral nervous system be selected from astrocytoma, neuroblastoma, myc-driven neuroblastoma, glioma, and schwannomas.

In accordance with the present invention, the treatment of haematological malignancies, in particular multiple myeloma is preferred.

Moreover, the compounds or composition for use according to the present invention may be particularly useful for use in the treatment of solid tumours, haematological malignancies, tumours of mesenchymal origin, tumours of the central and peripheral nervous system, melanoma, seminoma, teratocarcinoma, osteosarcoma, xeroderma pigmentosum, keratoacanthoma, thyroid follicular cancer, neuroendocrine tumours and Kaposi's sarcoma that are resistant or refractory to treatment with other anti-cancer or antiproliferative agents.

In yet another embodiment, the present invention provides compounds and compositions according to the present invention as described above for use in inhibiting tumour angiogenesis and/or metastasis.

The potent inhibitory effect of the compounds of the invention may be determined by in vitro enzyme assays as described in the Example Section in more detail.

In another embodiment, the present invention provides a novel synthesis method for obtaining the novel compounds of formula (I) or (II)

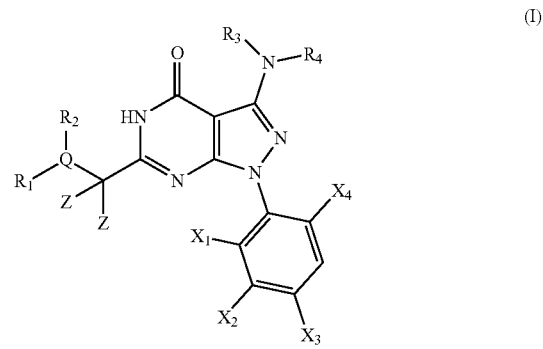

-continued

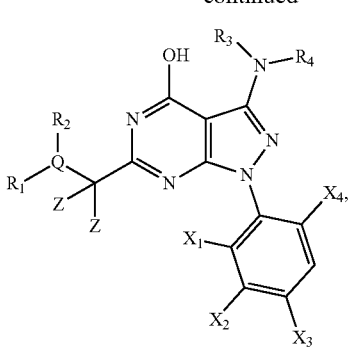
(II)

wherein $X_1$, $X_2$, $X_3$ and $X_4$, z, Q and $R_1$, $R_2$, $R_3$ and $R_4$ are defined as above, comprising the step of condensation a hydrazine of formula (III)

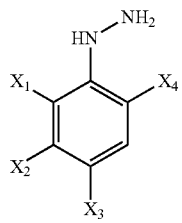
(III)

and a dinitril derivative of formula (IV)

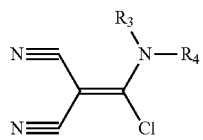
(IV)

to obtain a aminopyrazole nitrile compound of formula (V)

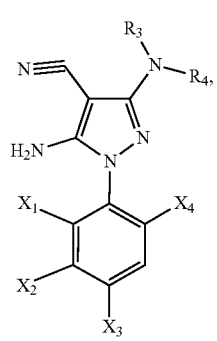
(V)

wherein $R_3$, $R_4$ and $X_1$, $X_2$, $X_3$ and $X_4$ are as defined above.

In a further embodiment, the synthesis according to the present invention additionally comprises one or more of the following steps of synthesis of an arylhydrazine of formula (III);

C-acylation of malonitrile with dimethylcarbamoyl chloride to obtain a dinitril derivative of formula (IV);

hydrolysis of the dinitril derivatives of formula (V) to carboxamides of formula (VI);

synthesis of methylacetate derivatives of formula (VII) and condensation of carboxamides (VI) with methylacetate derivatives (VII) to obtain pyrimidones of formula (I) or (II).

Moreover, the synthesis as described above, optionally additionally comprises the step(s) as disclosed in any of General Procedure (GP)-D, -E, -F, and -G as shown in the synthesis scheme such as Suzuki-coupling of Q-Bromo derivatives 6a-h of formula (I) or (II) yielding Q-alkyl compounds 7a-h of formula (I) or (II) (i.e. GP-D);

reaction of Q-NH$_2$ derivatives 6a-h of formula (I) or (II) with isocyanates yielding carbamides 8a-h of formula (I) or (II) (i.e. GP-E);

acylation of Q-NH$_2$ derivatives 6a-h of formula (I) or (II) with chloroacetyl-chloride to obtain the carbamides 9a-h of formula (I) or (II) (i.e. GP-F) followed the reaction with amines to obtain amide derivatives 10a-h of formula (I) or (II) (i.e. GP-G).

In yet another embodiment, the present invention provides a novel aminopyrazole nitrile intermediate compound of the general formula (V):

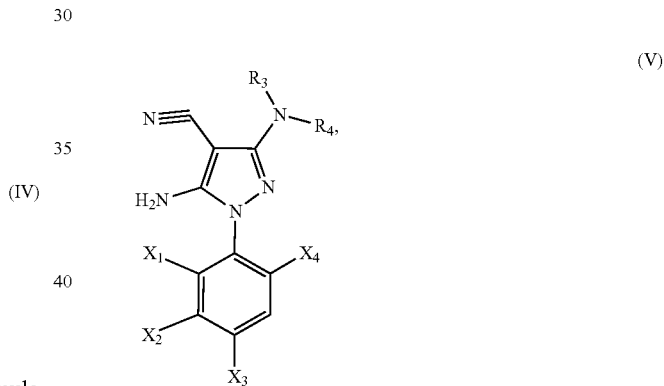
(V)

wherein $R_3$, $R_4$ and $X_1$, $X_2$, $X_3$ and $X_4$ are defined as above.

In particular, the present invention provides an aminopyrazole nitrile intermediate compound of formula (V), wherein $R_3$ is $CH_3$, $R_4$ is $CH_3$, $X_1$ is Cl, $X_4$ is Cl and $X_2$ is H.

In a further embodiment, the present invention also provides the in vitro use of a compound of formula (I) or (II)) according to the invention or a composition comprising the compounds according to the invention as a CDK inhibitor.

Definitions

The following definitions apply throughout the present specification, unless specifically indicated otherwise.

As used herein, a kinase "inhibitor" refers to a compound capable of downregulating, suppressing or otherwise regulating the amount and/or activity of a kinase. Inhibition of these kinases can be achieved by a variety of mechanisms known in the art, including, but not limited to binding directly to the kinase polypeptide, denaturating/downregulating or otherwise inactivating the kinase, or inhibiting the expression of the gene (e.g., transcription to mRNA, translation to a nascent polypeptide and/or final peptide).

As used herein, the term "inhibiting" or "inhibition" refers to the ability of a compound to downregulate, decrease, reduce, suppress, inactivate or inhibit at least partially the activity of an enzyme or the expression of an enzyme or protein.

In accordance with the above, the compounds according to the general formula (I) or (II)) as well as their pharmaceutically acceptable salts, solvates and prodrugs thereof are used as an inhibitor for a protein kinase, preferably as an inhibitor for a cellular protein kinase.

In a preferred embodiment, said cellular protein kinase is a cyclin dependent kinase (CDK). The cyclin dependent protein kinase can be selected from the group comprising CDK1/CDC2/CDC28A/CDKN1/P34CDC2, CDK2/CDKN2, CDK3/CDKN3, CDK4, CDK5/CDKN5, CDK6/CDKN6, CDK7/CAK/CAK1/CDKN7/MO15/STK1, CDK8, CDK9/CDC2L4/TAK, CDK10, CDK11A/CDC2L2/CDC2L3/PITSLREB, CDK11B/CDC2L1/CDK11/PITSLREA/PK58, CDK12/CRK7/CRKRS/KIAA0904, CDK13/CDC2L/CDC2L5/CHED/KIAA1791, CDK14/KIAA0834/PFTK1, CDK15/ALS2CR7/PFTK2, CDK16/PCTAIRE1/PCTK1, CDK17/PCTAIRE2/PCTK2, CDK18/PCTAIRE3/PCTK3, CDK19/CDC2L6/CDK11/KIAA1028, CDK20/CCRK/CDCH, CDKL1, CDKL2, CDKL3/NKIAMRE, CDKL4, and CDKL5/STK9.

Furthermore, in another particularly preferred embodiment, the compounds according to the present invention show a high potency (as demonstrated by a low $IC_{50}$ value) for inhibiting CDK7 and/or 9 activity.

Particularly preferred are compounds which show a more potent CDK7 and/or 9 than CDK 4, 6 and/or 8 inhibition.

Thus, the compounds of the present invention preferably selectively inhibit CDK1, 2, 3, 5, 7, 9, 13 and/or 16.

As can be determined, inter alia, by the assay disclosed in Moshinsky D. J. et al, J Biomol. Screen 2003, pp. 443-452, referred to in more detail in the example section.

The compounds of formula (I) or (II) may exist in the form of different isomers, in particular stereoisomers (including, e.g., geometric isomers (or cis/trans isomers), enantiomers and diastereomers) or tautomers. All such isomers of the compounds of formula (I) or (II)) are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by conventional methods, such as, e.g., fractional crystallisation, separation or crystallisation of diastereomeric derivatives, or separation by chiral column chromatography. The individual optical isomers can also be obtained from the racemates via salt formation with an optically active acid followed by crystallisation.

The present invention also includes all suitable isotopic variations of the compounds of formula (I) or (II)), or pharmaceutically acceptable salts and solvates thereof. An isotopic variation of the compounds of formula (I) or (II)) of the present invention or a pharmaceutically acceptable salt or solvate thereof is defined as one in which at least one atom is replaced by an atom having the same atomic number but an atomic mass different from the atomic mass usually found in nature. Examples of isotopes that can be incorporated into the compounds of formula (I) or (II)), and pharmaceutically acceptable salts or solvates thereof include isotopes of hydrogen, carbon, nitrogen, oxygen, phosphorus, sulphur, fluorine and chlorine such as $^{2}H$, $^{3}H$, $^{13}C$, $^{14}$, $^{15}N$, $^{17}O$, $^{18}O$, $^{31}P$, $^{32}P$, $^{35}S$, $^{18}F$ and $^{36}Cl$, respectively. Certain isotopic variations of the compounds of formula (I) or (II)), and pharmaceutically acceptable salts or solvates thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of formula (I) or (II) of the present invention and pharmaceutically acceptable salts or solvates thereof can generally be prepared by conventional procedures using appropriate isotopic variations of suitable reagents.

As used herein, the terms "halogen" or "halo" refer to fluoro (—F), chloro (—Cl), bromo (—Br), or iodo (—I).

As used herein, the term "alkyl" alone or used in conjunction as, e.g., in "alkoxy" refers to a monovalent saturated acyclic (i.e. non-cyclic) hydrocarbon group which may be linear or branched. Accordingly, an "alkyl" group does not comprise any carbon-to-carbon double bond or any carbon-to-carbon triple bond. A "$C_{1-6}$ alkyl" denotes an alkyl group having 1 to 6 carbon atoms. Exemplary alkyl groups are methyl, ethyl, propyl (e.g., n-propyl or isopropyl), butyl (e.g., n-butyl, isobutyl, sec-butyl, or tert-butyl), pentyl (n-pentyl, tert-pentyl, neopentyl, isopentyl, sec-pentyl and 3-pentyl) and hexyl (n-hexane, isohexane, neohexane, diisopropyl, 3-methylpentyl); preferred examples being methyl, ethyl, propyl (e.g., n-propyl or isopropyl), butyl (e.g., n-butyl, isobutyl, sec-butyl, or tert-butyl), whereby $C_1$ to $C_3$-alkyl (i.e. methyl), ethyl and propyl (e.g., n-propyl or isopropyl) are more preferred.

As used herein, the term "5- or 6 membered aromatic ring which may contain one or more hetero atoms selected from N, O and S" refers to an aromatic ring group selected from phenyl, pyridinyl (e.g., 2-pyridyl, 3-pyridyl, or 4-pyridyl), indolyl imidazolyl, thiazolyl, 1H-tetrazolyl, 2H-tetrazolyl, thienyl (i.e., thiophenyl), pyrimidinyl, furanyl (i.e. furyl), pyrrolyl (i.e. azolyl) (e.g. 2H-pyrrolyl), pyrazolyl, imidazolyl, oxazolyl, isoxazolyl, thiazolyl, isothiazolyl, triazolyl, pentazolyl, thiadiazolyl, pyridazinyl, pyrazinyl, triazinyl (1,3,5-triazinyl, 1,2,4-triazinyl, 1,2,3-triazinyl-) and tetrazinyl. Preferred exemplary groups are phenyl, pyridine, thiophene, isoxazole and thiazole.

As used herein, the terms "optional", "optionally" and "may" denote that the indicated feature may be present but can also be absent. Whenever the term "optional", "optionally" or "may" is used, the present invention specifically relates to both possibilities, i.e. that the corresponding feature is present or, alternatively, that the corresponding feature is absent.

Groups may be referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, unless explicitly indicated otherwise or contradicted by context, the terms "a", "an" and "the" are used interchangeably with "one or more" and "at least one". Thus, for example, a composition comprising "a" compound of formula (I) or (II) can be interpreted as referring to a composition comprising "one or more" compounds of formula (I) or (II).

Pharmaceutically acceptable salts of the compounds of the invention of formula (I) or (II)) can be formed with numerous organic and inorganic acids and bases. Exemplary acid addition salts including acetate, adipate, alginate, ascorbate, aspartate, benzoate, benzenesulfonate, bisulphate, borate, butyrate, citrate, camphorate, camphersulfonate, cyclopentanepropionate, digluconate, dodecyl sulphate, ethane sulfonate, fumarate, glucoheptanoate, glycerophosphate, hemisulphate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulphate, 3-phenyl sulfonate, 3-phenylpropionate, phosphate, picrate, pivalate, propionate, salicylate, succinate, sulphate, sulfonate, tartrate, thiocyanate, toluene sulfonate such as tosylate, undecanoate, or the like.

Basic nitrogen-containing moieties can be quarternised with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminium salts and the like, as well as non-toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

If the compound of formula (I) or (II) is in the form of a pharmaceutically acceptable salt, it is preferably in the form of a hydrochloride salt. The hydrochloride salts of the compounds of the invention may inter alia be prepared as described in General Procedure I.

Pharmaceutically acceptable salts of the compounds of the present invention may be synthesised from the parent compounds which contain a basic or acidic moiety by conventional chemical methods. Generally, such salts can be prepared by reacting the free acid or base form of these compounds with a stoichiometric amount of the appropriate base or acid in water, an organic solvent or a mixture thereof.

Moreover, the scope of the invention embraces the compounds of formula (I) or (II)) in any solvated form, including, e.g., solvates with water (i.e. as a hydrate) or solvates with organic solvents such as, e.g., methanol, ethanol or acetonitrile (i.e. as a methanolate, ethanolate or acetonitrilate), or in any crystalline form (i.e. as any polymorph), or in amorphous form. It is to be understood that such solvates of the compounds of the formula (I) or (II)) also include solvates of pharmaceutically acceptable salts of the compounds of the formula (I) or (II).

The term "pharmaceutically acceptable" is used herein to refer to those compounds, materials, compositions, and/or dosage forms which are within the scope of the sound medical judgment suitable for use in contact with the tissues of human and animals without excessive toxicity, irritation, allergic response, or other problem or complication commensurate with a reasonable risk/benefit ratio.

The term "prodrug(s)", as used herein, is intended to include any covalently bonded carriers which release the active parent drug of the present invention in vivo when such a prodrug is administered to a mammalian subject. Since prodrugs are known to enhance numerous desirable qualities of pharmaceuticals such as solubility, bioavailability and stability, the compounds of the present invention may be delivered in prodrug form. Prodrugs of the present invention can be prepared by modifying functional groups present in the compounds in such a way that the modifications are cleaved in vivo by metabolic processes within the body to convert the inactive form to the usable active parent compound.

Prodrugs include compounds of the present invention, wherein a hydroxyl, amino, or sulfhydryl group is bonded to any group that, when administered to a mammalian subject, is cleaved to form a free hydroxyl, free amino or free sulfhydryl group, respectively. Examples of prodrugs include, but are not limited to acetate, formate and benzoate derivatives of alcohols and amine functional groups in the compounds of the present invention.

The term "therapeutically effective amount" of a compound of the present invention refers to an amount sufficient to effect desired clinical results (i.e. achieve therapeutic efficacy).

The term "treatment" of a disorder or disease as used herein (e.g., "treatment" of cancer) is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "treatment" as used in accordance with the present invention is meant to encompass also prevention/prophylaxis, unless indicated otherwise.

The terms "prevention" and "prophylaxis" of a disorder or disease as used herein (e.g., "prevention/prophylaxis" of cancer) are also well known in the art. They are used interchangeably throughout the specification. For example, a patient/subject suspected of being prone to suffer from a disorder or disease may particularly benefit from a prevention/prophylaxis of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the terms "prevention" and "prophylaxis" comprise the use of a compound of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I) or (II).

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

Dosage and Formulation

A person of skill in the art such as a physician will be able to determine the actual dosage, which will be most suitable for an individual subject. The specific dose and frequency of dosing for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

For the purpose of the present invention, a therapeutically effective dosage will generally be from about 14 to about 50 mg/m$^2$/day, which may be administered in one or multiple doses.

It will be appreciated, however, that specific dose levels of the compounds of the invention for any particular patient will depend on a variety of factors such as age, sex, body weight, general health condition, diet, individual response of the patient to be treated at the time of administration, severity of the disease to be treated, the activity of particular compound applied, dosage form, mode of application and concomitant medication. The therapeutically effective amount for a given situation will readily be determined by routine experimentation and is within the skills and judgement of the ordinary clinician or physician.

The unit dose may be administered, e.g., daily, weekly or once every two weeks. It will be appreciated that it may be necessary to make routine variations to the dosage depending on the age and weight of the patient/subject as well as the severity of the condition to be treated. The precise dose and also the route of administration will ultimately be at the discretion of the attendant physician.

The compounds of the present invention may be administered by oral route; parenteral route using injection techniques or infusion techniques, including by subcutaneous, intradermal, transdermal, transmucosal, subdural, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; local or topical e.g. via iontophoresis, sublingual, by pulmonary route, including by inhalation or insufflation therapy; gastrointestinal route; intrauterine route; intraocular route; subcutaneous route; or ophthalmic route, including by intravitreal, or intracameral route or by rectal route. Particularly preferred routes of administration are parenteral administrations like, e.g., intravenous and intraperitoneal (during hyperthermic chemoperfusion) and oral administration, whereby the oral administration is particularly preferred.

The compounds provided by the present invention may be administered as compounds per se or may be formulated as pharmaceutical compositions. The pharmaceutical compositions may optionally comprise one or more pharmaceutically acceptable excipients, such as carriers, diluents, fillers, disintegrants, lubricating agents, binders, colourants, pigments, stabilisers, preservatives, antioxidants, and/or solubility enhancers, as described in more detail below.

The compounds of formula (I) or (II) and pharmaceutical compositions comprising a compound of formula (I) or (II)) may thus be administered to a subject by any convenient route of administration, whether systemically/peripherally or at the site of desired action, including but not limited to one or more of: oral (e.g., as a tablet, capsule, or as an ingestible solution), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal (in particular in form of hyperthermic chemoperfusion), intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, or ophthalmic (including intravitreal or intracameral) administration.

The pharmaceutical compositions can be formulated as dosage forms for oral, parenteral, such as intramuscular, intravenous, subcutaneous, intradermal, intraarterial, or intraperitoneal (especially in form of hyperthermic chemoperfusion) administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders, and granules for reconstitution.

Oral and parenteral, in particular intravenous administration is preferred, whereby oral administration is particularly preferred.

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or oleaginous solutions or emulsions for infusion, aqueous or oleaginous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

Dosage forms for oral administration selected from tablets, capsules are preferred.

The amount of the compound of the present invention that may be combined with the excipients to formulate a single dosage form will vary upon the patient treated and the particular mode of administration.

The compounds according to the present invention of formula (I) or (II) may be formulated into pharmaceutical compositions using one or more conventional pharmaceutically acceptable excipient(s) commonly used in formulation technology, e.g., such as inter alia referred to in Fiedler's "Lexikon der Hilfstoffe" $5^{th}$ Edition, Editio Cantor Verlag Aulendorf 2002, "The Handbook of Pharmaceutical Excipients", $4^{th}$ Edition, American Pharmaceuticals Association, 2003, and may be selected from carriers, diluents or fillers, binding agents, disintegrants, lubricants, glidants, stabilising agents, surfactants, film-formers, softeners, wetting agents, sweeteners, pigments/colouring agents, antioxidants, preservatives and the like. Suitable carriers, binding agents, disintegrants, lubricants and glidants can, e.g., be the ones described in more detail here above as pharmaceutically acceptable auxiliary agents.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilisers, thickening agents, stabilisers, disintegrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, $15^{th}$ Ed., Mack Publishing Co., New Jersey (1991).

The pharmaceutical compositions can be formulated by techniques known to the person skilled in the art, such as the techniques published in "Remington: The Science and Practice of Pharmacy", Pharmaceutical Press, $22^{nd}$ edition, "Pharmazeutische Technologie", $11^{th}$ Edition Deutscher Apotheker Verlag 2010, or "Pharmazeutische Technologie", $9^{th}$ Edition Wissenschaftliche Verlagsgesellschaft Stuttgart, 2012.

For parenteral administration, the compounds are best used in the form of a sterile aqueous solution, which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerol, and combinations thereof.

Lists of further suitable excipients may also be found in textbooks such as Remington's Pharmaceutical Sciences, $18^{th}$ Ed. (Alfonso R. Gennaro, ed.; Mack Publishing Company, Easton, Pa., 1990); Remington: the Science and Practice of Pharmacy $19^{th}$ Ed. (Lippincott, Williams & Wilkins, 1995); Handbook of Pharmaceutical Excipients, $3^{rd}$ Ed. (Arthur H. Kibbe, ed.; Amer. Pharmaceutical Assoc, 1999); the Pharmaceutical Codex: Principles and Practice of Pharmaceutics $12^{th}$ Ed. (Walter Lund ed.; Pharmaceutical Press, London, 1994); The United States Pharmacopeia: The National Formulary (United States Pharmacopeial Convention); and Goodman and Gilman's: the Pharmacological Basis of Therapeutics (Louis S. Goodman and Lee E. Limbird, eds.; McGraw Hill, 1992), the disclosures of which are hereby incorporated by reference.

Said compounds or pharmaceutical compositions may also be administered by sustained-release systems. Suitable examples of sustained-release compositions include semipermeable polymer matrices in the form of shaped articles, e.g., films, or microcapsules. Sustained-release matrices include, e.g., polylactides (see, e.g., U.S. Pat. No. 3,773, 919), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(–)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE 32 18 121; Epstein et al., Proc. Natl. Acad. Sci. (USA) 82:3688-3692

(1985); Hwang et al., Proc. Natl. Acad. Sci. (USA) 77:4030-4034 (1980); EP 0 052 322; EP 0 036 676; EP 0 880 46; EP 0 143 949; EP 0 142 641; JP 83-118008; U.S. Pat. Nos. 4,485,045; 4,544,545; and EP 0 102 324.

Said compounds or pharmaceutical compositions may also be administered by the pulmonary route or the ocular route. For ophthalmic use, they can be formulated as micronised suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

The compound of formula (I) or (II) or a pharmaceutical composition comprising the compound of formula (I) or (II) can be administered in monotherapy (e.g., without concomitant administration of any further therapeutic agents or, in particular, without concomitant administration of any further antiproliferative agents or anticancer drugs). However, the compound of formula (I) or (II) or a pharmaceutical composition comprising the compound of formula (I) or (II) can also be administered in combination with at least one further therapeutic agent (i.e. one or more further therapeutic agents) and/or radiotherapy.

If the compound of formula (I) or (II) is used in combination with at least a second therapeutic agent active against the same disease or condition (e.g., a further anticancer drug), the dose of each compound may differ from that when the corresponding compound is used alone, in particular, a lower dose of each compound may be used. The combination of the compound of formula (I) or (II) with one or more further therapeutic agents may comprise the simultaneous/concomitant administration of the compound of formula (I) or (II) and the further therapeutic agent(s) (either in a single pharmaceutical formulation or in separate pharmaceutical formulations), or the sequential/separate administration of the compound of formula (I) or (II) and the further therapeutic agent(s). If administration is sequential, either the compound of formula (I) or (II)) according to the invention or the one or more further therapeutic agents may be administered first. If administration is simultaneous, the one or more further therapeutic agents may be included in the same pharmaceutical formulation as the compound of formula (I) or (II)), or they may be administered in one or more different (separate) pharmaceutical formulations.

Preferably, the one or more further therapeutic agents to be administered in combination with a compound of the present invention are antiproliferative agents or anticancer drugs. The antiproliferative agent(s) or anticancer drug(s) to be administered in combination with a compound of formula (I) or (II)) according to the invention may, e.g., be selected from: an angiogenesis inhibitor (e.g., a protease inhibitor, a fibroblast growth factor receptor kinase inhibitor, or a vascular endothelial growth factor receptor kinase inhibitor); a cytostatic drug (e.g., an antimetabolite, such as purine and pyrimidine analogue antimetabolites); an antimitotic agent (e.g., a microtubule-stabilising drug or an antimitotic alkaloid); a platinum coordination complex; an anti-tumour antibiotic; an alkylating agent (e.g., a nitrogen mustard or a nitrosourea); an endocrine agent (e.g., an adrenocorticosteroid, an androgen, an anti-androgen, an oestrogen, an anti-oestrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumour cell (e.g., ATP and GTP phosphodiesterase inhibitors, histone deacetylase inhibitors, protein kinase inhibitors (such as serine, threonine and tyrosine kinase inhibitors, e.g., Abelson protein tyrosine kinase inhibitors) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors, PI3K inhibitors and platelet-derived growth factor receptor kinase inhibitors)); methionine, aminopeptidase inhibitors, proteasome inhibitors, cyclooxygenase inhibitors (e.g., cyclooxygenase-1 or cyclooxygenase-2 inhibitors), topoisomerase inhibitors (e.g., topoisomerase I inhibitors or topoisomerase II inhibitors), poly ADP ribose polymerase inhibitors (PARP inhibitors), and epidermal growth factor receptor (EGFR) inhibitors/antagonists. In addition, this also includes combination with an immunooncology therapeutic agent, e.g., targeting CTLA-4, PD-1/PD-L1, but also other immune-stimulatory strategies.

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazine (such as temozolomide).

A platinum coordination complex, which can be used as an anticancer drug in combination with a compound of the present invention may be, for example, cisplatin, carboplatin, nedaplatin, oxaliplatin, satraplatin, or triplatin tetranitrate.

A cytotoxic drug, which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent, which can be used as an anticancer drug in combination with a compound of the present invention may be, for example, a taxane (such as docetaxel, larotaxel, ortataxel, paclitaxel/taxol, tesetaxel, or nab-paclitaxel (e.g., Abraxane®)), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumour antibiotic, which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumour antibiotic isolated from *Streptomyces* (such as actinomycin (including actinomycin D), bleomycin, mitomycin (including mitomycin C), or plicamycin.

A tyrosine kinase inhibitor, which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, axitinib, nintedanib, ponatinib, or vandetanib.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (i.e. the compound of formula (I) or a pharmaceutically acceptable salt or solvate thereof) or the further therapeutic agent(s) may be administered first. When administration is simultaneous, the combination may be administered either in the same pharmaceutical composition or in different pharmaceutical compositions. When combined in the same formulation, it will be appreciated that the two or more compounds must be stable and compatible with each other and the other components of the formulation. When formulated separately, they may be provided in any convenient formulation.

The compounds of formula (I) or (II)) can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The subject or patient to be treated in accordance with the present invention may be an animal (e.g., a non-human animal), or a human. Preferably, the subject/patient is a mammal. More preferably, the subject/patient is a human.

Particularly preferred are compositions, wherein the additional therapeutic agent is selected from the group of proteasome inhibitors such as bortezomib, carfilzomib, ixazomib, marizomib (Salinosporamide A), oprozomib; immune modulatory drugs (i.e. cereblon-modulators) such as thalidomide-like drugs (e.g. lenalidomide, thalidomide, pomalidomide); DNA damage inducers/inducing therapies such as alkylating drugs including monofunctional methylating agents (e.g., temozolomide [TMZ], -methyl- -nitro- -nitrosoguanidine [MNNG], and dacarbazine), bifunctional alkylating agents such as nitrogen mustards (e.g., melphalan chlorambucil and cyclophosphamide and ifosfamide), or chloroethylating agents (e.g., nimustine [ACNU], carmustine [BCNU], lomustine [CCNU], and fotemustine) as well as anthracyclines such as doxorubicin; MAPK pathway inhibitors such as Raf inhibitors (e.g. vemurafenib, dabrafenib), MEK inhibitors (e.g. trametinib, selumetinib, binimetinib, refametinib, pimasertib, cobimetinib, PD-325901, CI-1040, and TAK-733) and ERK inhibitors (e.g. Ulixertinib)); PI3K/Akt pathway inhibitors such as PI3K inhibitors (e.g. idelalisib, copanlisib, gedatolisib, buparlisib), Akt inhibitors (e.g. uprosertib, MK2206, AZD5363, afuresertib, ipatasertib), mTOR inhibitors (e.g. sirolimus, temsirolimus); pro-apoptotic receptor agonists (e.g. dulanermin, mapatumumab, lexatumumab, drozitumab, conatumumab, tigatuzumab), selective BCL-2 family inhibitors/BH3 mimetic drugs (e.g. navitoclax, venetoclax, maritoclax, obatoclax, sabutoclax, WEHI-539, A-1155463 and A-1331852); BET inhibitors (e.g. MK-8628, TEN-010, GSK525762, GSK2820151, CPI-0610, ABBV-075, BAY1238097, INCB054329, FT-1101, GS-5829, BMS 986158, JQ-1), TNF pathway agonists such as dulanermin and inhibitors of poly(ADP-ribose) polymerase (PARP) such as veliparib, iniparib, talazoparib, niraparib, olaparib, rucaparib, and/or combined with radiotherapy.

These combinations/regimes are particularly preferred for the treatment and/or prophylaxis of MM.

Synthesis of Compounds

The synthesis of the compounds of the present invention is preferably carried out according to the general synthetic scheme shown in Scheme 1, below, together with synthetic methods known in the art of synthetic chemistry, or variations thereof as appreciated by those skilled in the art. Preferred methods include, but are not limited to those methods described below.

$X_1$, $X_2$, $X_3$, $X_4$, Z, Q and $R_1$, $R_2$, $R_3$ and $R_4$ in general formulae (I) to (VI) are as defined above.

In particular, Examples a to h depicted in the synthetic scheme the variables have the meaning as shown in Scheme 1.

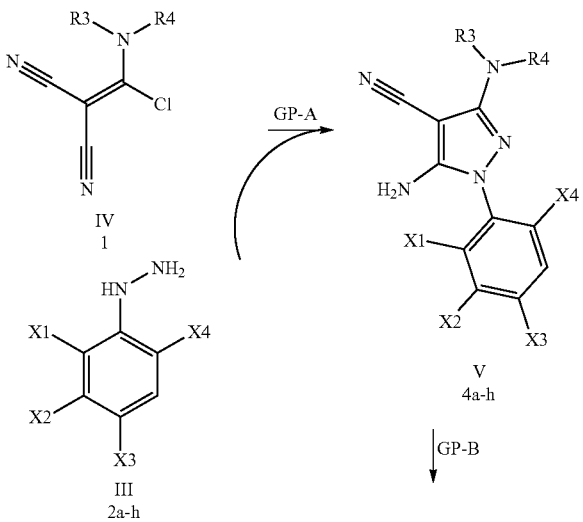

-continued

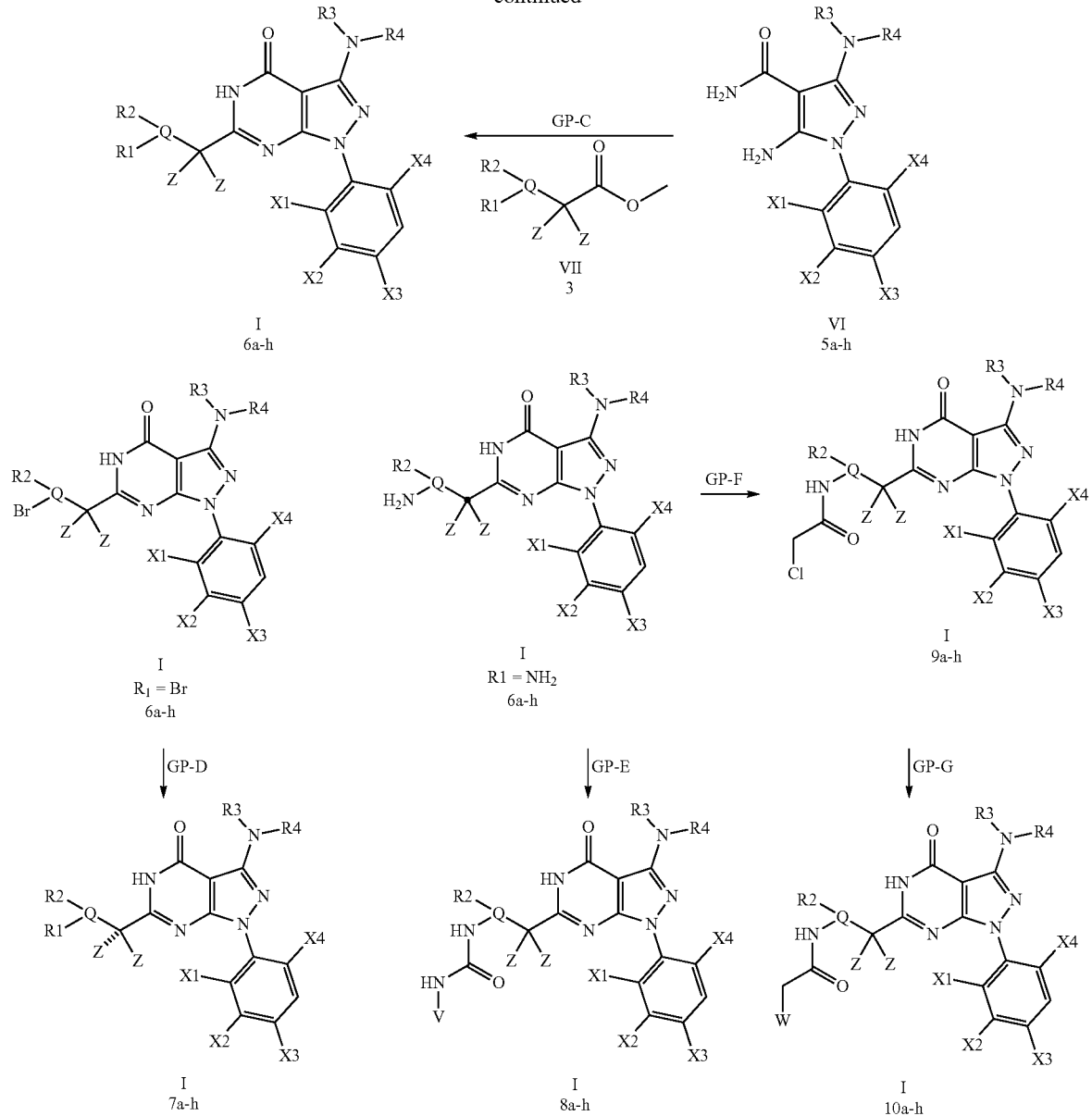

a: X1 = X4 = Cl X2 = H X3 = SO$_2$NH$_2$
b: X1 = X4 = Cl X2 = X3 = H
c: X1 = X4 = H X2 = H X3 = Cl
d: X4 = OCH$_3$ X1 = F X2 = F X3 = H
e: X1 = X4 = Cl; X2 = X3 = H
f: X1 = X4 = Cl X2 = H X3 = CONH$_2$
g: X1 = X4 = F X2 = H X3 = SO$_2$NH$_2$
h: X1 = X4 = Cl X1 = H X3 = COOH

V: phenyl, substitited phenyl, heteroaryl, substituted heteroaryl
W: morpholine-1-yl, piperazine-1-yl or dialkylamino Thus, the present invention in a further embodiment also provides a novel process for the synthesis of the compounds of the present invention, as well as novel intermediates to be used in the process of the invention.

The method according to the present invention thus comprises one or more of the following steps:

1. Synthesis of arylhydrazines in case when they are not available commercially
2. C-acylation of malonitrile with dialkylcarbamoyl chloride
3. Condensation of hydrazines and dinitril derivatives yielding aminopyrazole nitriles
4. Hydrolysis of nitriles to carboxamides
5. Synthesis of methylacetates in case when they are not available commercially
6. Condensation of carboxamides with methyl acetate derivatives
7. Suzuki-coupling of the Q-bromo derivatives 8. Reaction of Q-amine derivatives with isocyanates yielding carbamides
9. Acylation of Q-amines with chloroacetyl chloride yielding chloroacetyl derivatives followed by reaction of amines.

In this context, it is noted that example compounds 1 to 5 and 7 to 9 are intermediates to be used in the synthetic method according to the present invention.

EXAMPLES

Example 1

Malononitrile of General Formula (IV)

2-(Chloro-dimethylamino-methylene)-malononitrile (1)

20 g malonitrile was dissolved in the mixture of 1000 ml isopropanol and 200 ml dimethylformamide. 50 g potassium t-butylate was added in portions with stirring. After 1 hour at ambient temperature 20 ml dimethylcarbamoyl chloride was added dropwise and stirred overnight. The solid precipitate was filtered and washed carefully with isopropanol then ether. After drying in vacuum the crude material was used in the next step without any further purification. (Yield: 42 g)

40 g material obtained in the previous step was suspended in 200 ml phosphorus oxychloride and refluxed for four hours with stirring. Oxychloride was removed in vacuum and the residue was extracted with ethylacetate/saturated sodium bicarbonate solution to remove inorganic salts and the traces of acids. Organic phase was separated, dried on sodium sulfate and evaporated. Thick brown oil was obtained, which was distilled in vacuum. The fraction boiling at 146-148° C. (1 mmHg) was collected. The pure product is yellowish oil, which slowly solidifies at cooling.

Yield: 8 g

Example 2

Hydrazines of General Formula (III)

2a was synthesised according to Markwalder, Jay A.; Seitz, Steven P.; Sherk, Susan R, PCT Int. Appl. (2003), WO 2003063764 A2 Aug. 7, 2003

(2,3-Difluoro-6-methoxy-phenyl)-hydrazine (2d)

8.5 g 3,4-difluoroanisole was dissolved in mixture of 50 ml dry tetrahydrofurane and 25 ml dry dioxane then cooled to −70° C. with stirring. After 5 min 5.85 ml lithium compound was added dropwise. After 2 hours 11.5 g boc compound dissolved in 50 ml dry tetrahydrofurane was dropped into the reaction mixture. It was allowed to warm to room temperature then stirred overnight.

The solution was diluted with ethylacetate and extracted three times with saturated bicarbonate solution followed with brine. Organic phase was dried on sodium sulfate and evaporated to dryness.

Boc groups were removed with EtOAc/HCl stirring overnight.

The product was extracted with water and treated with charcoal.

pH of the aqueous solution was adjusted to 11 with 1 N sodium hydroxide solution, then extracted with EtOAc. Organic phase was dried and evaporated.

Yield: 4.96 g

Methyl 3,5-dichloro-4-hydrazinobenzoate (2f)

150 ml absolute methanol was cooled to −20° C., 10 ml thionyl chloride was added dropwise, stirred 20 minutes, 2.45 g 3,5-dichloro-4-hydrazinobenzoic acid was added, and warmed to ambient temperature. Solvents was removed, residue was neutralised with $NaHCO_3$, and extracted with EtOAc. Organic layer was dried, and solvent was evaporated. Residue was washed with DIPE and dried.

Yield: 1.5 g 3,5-Dichloro-4-hydrazinobenzoic Acid (2h)

3 g 3,5-dichloro-4-fluorobenzoic acid was dissolved in 25 ml ethanol. 5 ml hydrazine monohydrate was added and refluxed for 22 hours. Precipitated white solids were filtered, washed with ethanol and dried in vacuum.

Yield: 2.45 g

Example 3

5-amino-1-(4-carbamoyl-2,6-dichlorophenyl)-3-(dimethylamino)-1H-pyrazole-4-carboxamide (5f) (Carboxamide of General Formula VI)

3,5-dichloro-4-hydrazinobenzoic Acid 3 g 3,5-dichloro-4-fluorobenzoic acid was dissolved in 25 ml ethanol. 5 ml hydrazine monohydrate was added and refluxed for 22 hours. Precipitated white solids were filtered, washed with ethanol and dried in vacuum.

Yield: 2.45 g

Methyl 3,5-dichloro-4-hydrazinobenzoate (2f)

150 ml absolute methanol was cooled to −20° C., 10 ml thionyl chloride was added dropwise, stirred 20 minutes, 2.45 g 3,5-dichloro-4-hydrazinobenzoic acid was added, and warmed to ambient temperature. Solvents was removed, residue was neutralised with $NaHCO_3$, and extracted with EtOAc. Organic layer was dried, and solvent was evaporated. Residue was washed with DIPE and dried.

Yield: 1.5 g

Other hydrazines such as 2b, 2c, 2e were obtained from commercial sources.

General Procedure A (Synthesis of Pyrazoles 4a-h of General Formula (V))

The adequate substituted phenyl hydrazine (selected from 2a-h of general formula (III)) is dissolved in the mixture of methylenechloride and dimethylformamide and two equivalent triethylamine was added. The reaction mixture was cooled in ice bath and methylenechloride solution of (2-(chloro-dimethylamino-methylene)-malononitrile 1 of general formula (IV)) (1 equivalent) was added dropwise and stirred at ambient temperature for two days. Solvents were evaporated and the residue was extracted with ethylacetate/1 N hydrochloric acid. The organic phase was washed with 5% sodium carbonate solution and brine then dried on sodium sulfate. After evaporation the residue was treated with diisopropyl ether and the product was crystallised from 2-propanol.

Example 4 (General Procedure A)

4-(5-Amino-4-cyano-3-dimethylamino-pyrazol-1-yl)-3,5-dichloro-benzenesulfonamide (4a) of General Formula (V)

7.5 g 3,5-Dichloro-4-hydrazino-benzenesulfonamide was dissolved in the mixture of 250 ml methylenechloride and 70 ml dimethylformamide and 7 ml triethylamine was added. The reaction mixture was cooled in ice bath and methylenechloride solution of 3 (4 g in 60 ml) was added dropwise and stirred at ambient temperature for two days. Solvents were evaporated and the residue was extracted with ethylacetate/1N hydrochloric acid. The organic phase was washed with 5% sodium carbonate solution and brine, then dried on sodium sulfate. After evaporation the residue was treated with diisopropyl ether yielding 9.5 g crude product. This substance was crystallised from 150 ml 2-propanol.
Yield: 6.5 g Compounds 4b-h of general formula (V) were synthesised according to this procedure from the corresponding hydrazines.

Methyl 4-[5-amino-4-cyano-3-(dimethylamino)-1H-pyrazol-1-yl]-3,5-dichlorobenzoate) (4f) of General Formula (V)

1.5 g methyl 3,5-dichloro-4-hydrazinobenzoate and 0.9 g 2-(Chloro-dimethylamino-methylene)-malononitrile were solved in 30 ml dry dimethylformamide and 2.7 ml triethylamine was added. The mixture was stirred for 2 days at ambient temperature. Aqueous $NaHCO_3$ and EtOAc were added and the product was extracted. Organic layer was dried, and the solvent was evaporated. Residue was recrystallised in isopropanol, washed with diisopropyl ether and dried in vacuum.
Yield: 0.8 g General Procedure B (Synthesis of Carboxamides 5a-h of General Formula (VI))

The adequate substituted 4-cyanopyrazole (selected from 4a-h of general formula (V)) is dissolved in cc. sulfuric acid and stirred at 60° C. for 90 min. The reaction mixture is poured on crushed ice and neutralised with 40% aqueous sodium hydroxide which is added dropwise with stirring and cooling. As soon as pH is adjusted to 5-6 the product is isolated by extraction with ethyl acetate, which was dried over sodium sulphate then concentrated in vacuum.

Example 5 (General Procedure B)

5-Amino-1-(2,6-dichloro-4-sulfamoyl-phenyl)-3-dimethylamino-1H-pyrazole-4-carboxylic Acid Amide (5a) of General Formula (VI)

2 g of 4-(5-Amino-4-cyano-3-dimethylamino-pyrazol-1-yl)-3,5-dichloro-benzenesulfonamide was dissolved in 20 ml sulfuric acid and stirred at 60° C. for 90 min. The reaction mixture was poured on crushed ice and neutralised with 40% aqueous sodium hydroxide, which was added dropwise with stirring and cooling. As soon as pH was adjusted to 5-6, the product was isolated by extraction with ethyl acetate, then dried over sodium sulphate and concentrated in vacuum. The crystalline product was obtained from diethyl ether.
Yield: 1.4 g Compounds 5b-h of general formula (VI) were synthesised according to this procedure from the corresponding nitriles.

Methyl 4-[5-amino-4-carbamoyl-3-(dimethylamino)-1H-pyrazol-1-yl]-3,5-dichlorobenzoate (5f) of General Formula (VI)

740 mg methyl 4-[5-amino-4-cyano-3-(dimethylamino)-1H-pyrazol-1-yl]-3,5-dichlorobenzoate was dissolved in 3 ml $ccH_2SO_4$, and stirred for 5 days at ambient temperature. The solution was poured on 20 ml ice-water, neutralised with 2N NaOH, and solids were filtered, washed with water and dried in vacuum.
Yield: 0.7 g

4-[5-amino-4-carbamoyl-3-(dimethylamino)-1H-pyrazol-1-yl]-3,5-dichlorobenzoic Acid of General Formula VI 700 mg methyl 4-[5-amino-4-carbamoyl-3-(dimethylamino)-1H-pyrazol-1-yl]-3,5-dichlorobenzoate was solved in 20 ml water and 20 ml 2N NaOH was added. Mixture was stirred 5 hours at ambient temperature. Mixture was neutralised with 1N HCl, solids were filtered, washed with water and dried in desiccator.
Yield: 0.6 g

5-amino-1-(4-carbamoyl-2,6-dichlorophenyl)-3-(dimethylamino)-1H-pyrazole-4-carboxamide (5f) of General Formula VI 600 mg 4-[5-amino-4-carbamoyl-3-(dimethylamino)-1H-pyrazol-1-yl]-3,5-dichlorobenzoic acid was dissolved in 35 ml dry tetrahydrofurane and 315 mg 1,1'-carbonyldiimidazole was added. The mixture was stirred for 2 hours at ambient temperature in inert atmosphere (argon). 30 ml 25% ammonium hydroxide was added, and stirred for 2 hours. The solvent was removed in reduced pressure and sodium bicarbonate was added. Product was filtered, washed with water and dried in vacuum.
Yield: 0.5 g General Procedure C (Synthesis of Pyrimidones 6a-h of General Formula (I)/(II)))

Amino-pyrazol carboxamide (0.25 mmol) 5a-h of general formula (VI) and the corresponding phenylacetate (0.25 mmol) 3 were dissolved in 1 ml dry 2-propanol then 1 ml sodium methylate in methanol is added with stirring in presence of 2-3 pieces of molecular siever. It was stirred at 90° C. for one hour, then the reaction mixture was poured on the mixture of aqueous potassium bisulfate and crushed ice and extracted with ethyl acetate. Organic phase was dried on sodium sulfate, evaporated and the residue was triturated with diisopropylether or/and purified on silica column, if necessary.

Example 6

4-[6-(4-amino-benzyl)-3-dimethylamino-4-oxo-4,5-dihydro-pyrazolo[3,4-d]pyrimidin-1-yl]-3,5-dichloro-benzenesulfonamide of General Formula (I)/(II))

6(a) was prepared according to General Procedure C using 5a and methyl-4-aminophenylacetate 3 as starting materials.

Further compounds of the invention of general formula (I) and (II)) may be obtained according to general procedures D to G shown in Scheme 1, above.

General Procedure D (Synthesis of "Suzuki" Derivates 7a-h of General Formula (I)/(II)))

0.52 mmol of adequately substituted 6-(4-Bromo-benzyl)-1,5-dihydro-pyrazolo[3,4-d]pyrimidin-4-one (selected from 6a-h of general formula (I)/(II))) is dissolved 27 ml dimethoxyethane and stirred under argon atmosphere for 30 min after addition of 0.0477 g of Tetrakis(triphenylphosphine)palladium(0). 0.71 mmol of substituted benzeneboronic acid and 0.22 g of sodium carbonate was added in 4.1 ml of water, followed by overnight stirring of the fused mixtures at reflux temperature. The product was partitioned between ethyl acetate and water, the separated organic phase was dried concentrated and applied directly for column chromatography (silica gel/chloroform:methanol=100:1-5)

General Procedure E (Urea Derivatives 8a-h of General Formula (I)/(II)))

0.52 mmol of substituted 6-(Amino-benzyl)-1,5-dihydro-pyrazolo[3,4-d]pyrimidin-4-one (selected from 6a-h of general formula (I)/(II))) was dissolved in 5 ml dry pyridine and the corresponding isocyanate (1 equivalent) was added. The reaction mixture was stirred overnight then acidified with hydrochloric acid and extracted with ethyl acetate. Organic phase was washed with bicarbonate and brine then dried on sodium sulphate and evaporated to dryness. The residue was treated with ether and the precipitated product filtrated.

General Procedure F (Synthesis of Acylamino Derivatives 9a-h of General Formula (I)/(II)))

0.37 mmol of substituted 6-(Amino-benzyl)-1,5-dihydro-pyrazolo[3,4-d]pyrimidin-4-one (selected from 6a-h of general formula (I)/(II))) was dissolved in 11 ml dry DMF and chloroacetyl chloride (2 equivalent) dissolved in 1 ml DMF was added dropwise at 0° C. The reaction mixture was stirred for 2-4 hours, then ice and 5% aqueous solution of sodium bicarbonate are added and the product extracted with ethyl acetate. Organic phase was dried on sodium sulphate and evaporated to dryness. The residue applied for column chromatography (silica gel/chloroform:methanol=100:1-5).

General Procedure G (Synthesis of Tertiary Amino Derivatives 10a-h of General Formula (I)/(II)))

0.2 mmol chloroacetyl-amino derivative (selected from 9a-h of general formula (I)/(II))) was heated in 2 ml of the corresponding secondary amine at 80-100° C. overnight. Icy water was added and the product was extracted with ethyl acetate. The combined organic extracts were washed with brine, dried over magnesium sulphate and concentrated in vacuum. The residue was applied on silica column and eluted with chloroform:methanol=20:1-5).

General Procedure H (Cleavage of Methoxy Group)

The methoxyphenyl compound was dissolved in dichloromethane and treated with 3-5 equivalents of boron tribromide at 0-80° C. in a sealed tube.

General Procedure I (Hydrochloric Salt Formation)

Compound of the general formula (I) was dissolved in the mixture of ethanol and ethyl acetate (the ethanol content was 0-40%) and treated with one equivalent hydrochloric acid (4M solution in dioxin, purchased from Sigma-Aldrich.)

The following compounds according to the present invention where synthesised following the method of synthesis ("General Procedure") described above:

TABLE 1

Compounds of the invention
Compounds No. 1 to 5 and 7 to 9 are intermediate compounds according to the present invention.

| No. | Name | General method | Structure |
|---|---|---|---|
| 1 | 2-(Chloro-dimethylamino-methylene)-malononitrile | | 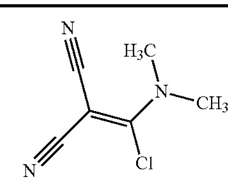 |
| 2 | (2,3-Difluoro-6-methoxy-phenyl)-hydrazine | | 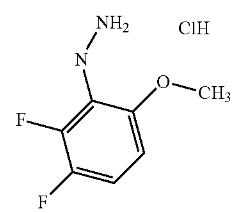 |
| 3 | 5-Amino-1-(4-carbamoyl-2,6-dichloro-phenyl)-3-dimethylamino-1H-pyrazole-4-carboxylic acid amide | | 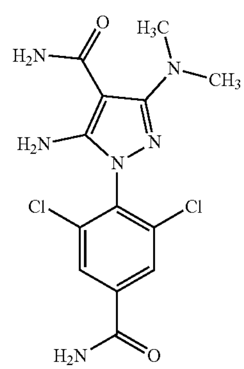 [SMILES: CN(C)c1nn(-c2c(Cl)cc(C(N)=O)cc2Cl)c(N)c1C(N)=O] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 4 | 4-(5-Amino-4-cyano-3-dimethylamino-pyrazol-1-yl)-3,5-dichloro-benzenesulfonamide | | 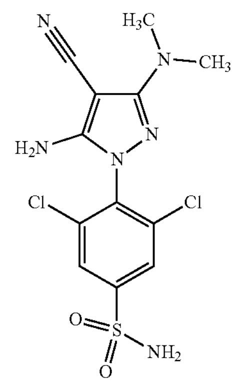 [SMILES: CN(C)c1nn(-c2c(Cl)cc(S(N)(=O)=O)cc2Cl)c(N)c1C#N] |
| 5 | 5-Amino-1-(2,6-dichloro-4-sulfamoyl-phenyl)-3-dimethylamino-1H-pyrazole-4-carboxylic acid amide | B | 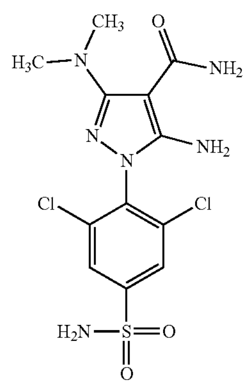 [SMILES: CN(C)c1nn(-c2c(Cl)cc(S(N)(=O)=O)cc2Cl)c(N)c1C(N)=O] |
| 6 | 4-[6-(4-Amino-benzyl)-3-dimethylamino-4-oxo-4,5-dihydro-pyrazolo[3,4-d]pyrimidin-1-yl]-3,5-dichloro-benzenesulfonamide | C | 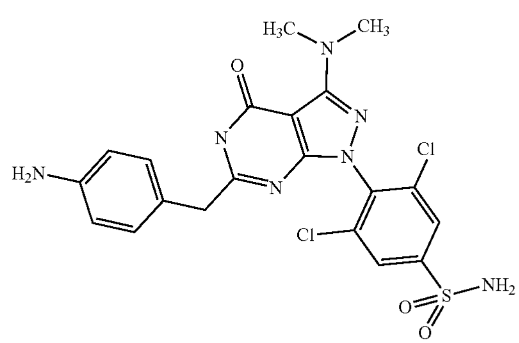 [SMILES: CN(C)c1nn(-c2c(Cl)cc(S(N)(=O)=O)cc2Cl)c2nc(Cc3ccc(N)cc3)[nH]c(=O)c12] |
| 7 | 5-Amino-1-(2,6-dichloro-phenyl)-3-dimethylamino-1H-pyrazole-4-carbonitrile | A | 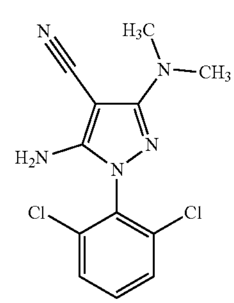 [SMILES: CN(C)c1nn(-c2c(Cl)cccc2Cl)c(N)c1C#N] |

TABLE 1-continued

Compounds of the invention
Compounds No. 1 to 5 and 7 to 9 are intermediate compounds according to the present invention.

| No. | Name | General method | Structure |
|---|---|---|---|
| 8 | 5-Amino-1-(2,6-dichloro-phenyl)-3-dimethylamino-1H-pyrazole-4-carboxylic acid amide | B | 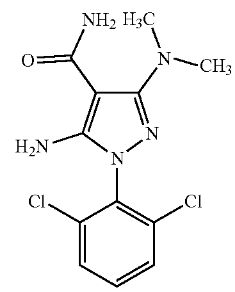 [SMILES: CN(C)c1nn(-c2c(Cl)cccc2Cl)c(N)c1C(N)=O] |
| 9 | 5-Amino-1-(2,3-difluoro-6-methoxy-phenyl)-3-dimethylamino-1H-pyrazole-4-carboxylic acid amide | B | 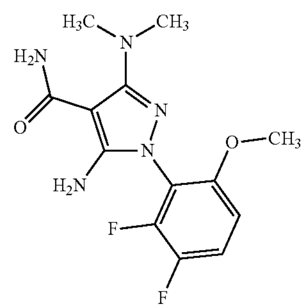 [SMILES: COc1ccc(F)c(F)c1-n1nc(N(C)C)c(C(N)=O)c1N] |
| 10 | 3,5-Dichloro-4-[3-dimethylamino-6-(3-hydroxy-benzyl)-4-oxo-4,5-dihydro-pyrazolo[3,4-d]pyrimidin-1-yl]-benzamide | C | 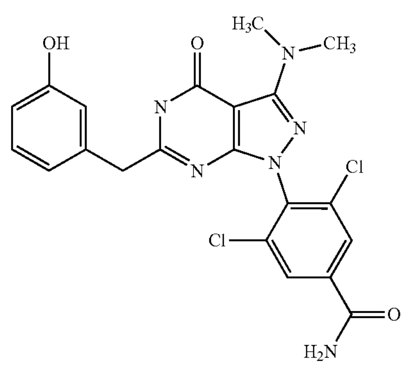 [SMILES: CN(C)c1nn(-c2c(Cl)cc(C(N)=O)cc2Cl)c2nc(Cc3cccc(O)c3)[nH]c(=O)c12] |
| 11 | 1-(2,6-Dichloro-phenyl)-3-dimethylamino-6-(3-hydroxy-benzyl)-1,5-dihydro-pyrazolo[3,4-d]pyrimidin-4-one | C | 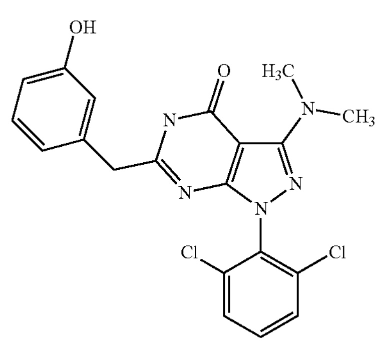 [SMILES: CN(C)c1nn(-c2c(Cl)cccc2Cl)c2nc(Cc3cccc(O)c3)[nH]c(=O)c12] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 12 | 6-[1-(2,6-Dichloro-phenyl)-3-dimethylamino-4-oxo-4,5-dihydro-1H-pyrazolo[3,4-d]pyrimidin-6-ylmethyl]-4H-benzo[1,4]oxazin-3-one | C | 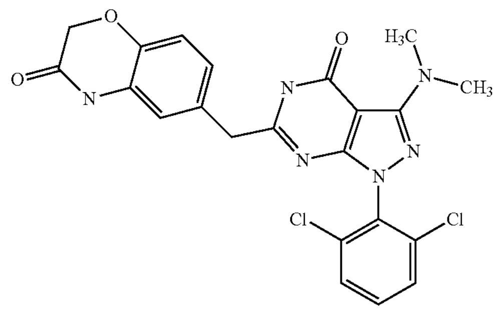 [SMILES: CN(C)c1nn(-c2c(Cl)cccc2Cl)c2nc(Cc3ccc4c(c3)NC(=O)CO4)[nH]c(=O)c12] |
| 13 | 1-(2,6-Dichloro-phenyl)-3-dimethylamino-6-(3-fluoro-benzyl)-1,5-dihydro-pyrazolo[3,4-d]pyrimidin-4-one | C | 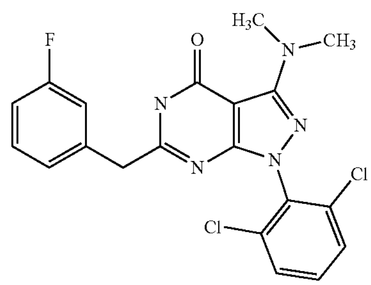 [SMILES: CN(C)c1nn(-c2c(Cl)cccc2Cl)c2nc(Cc3cccc(F)c3)[nH]c(=O)c12] |
| 14 | 6-(4-Butoxy-benzyl)-1-(2,6-dichloro-phenyl)-3-dimethylamino-1,5-dihydro-pyrazolo[3,4-d]pyrimidin-4-one | C | 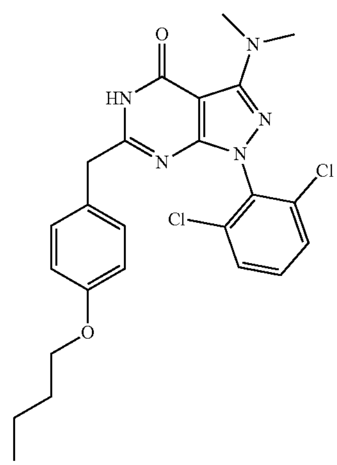 [SMILES: CCCCOc1ccc(Cc2nc3c(c(N(C)C)nn3-c3c(Cl)cccc3Cl)c(=O)[nH]2)cc1] |
| 15 | 6-Benzo[1,3]dioxol-5-ylmethyl-1-(2,6-dichloro-phenyl)-3-dimethylamino-1,5-dihydro-pyrazolo[3,4-d]pyrimidin-4-one | C | 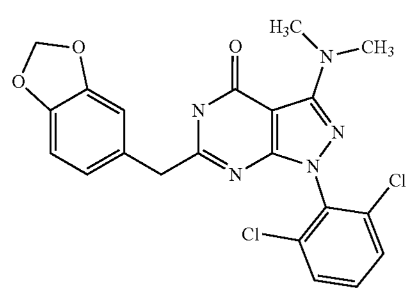 [SMILES: CN(C)c1nn(-c2c(Cl)cccc2Cl)c2nc(Cc3ccc4c(c3)OCO4)[nH]c(=O)c12] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 16 | 6-(4-Amino-benzyl)-1-(2,6-dichloro-phenyl)-3-dimethylamino-1,5-dihydro-pyrazolo[3,4-d]pyrimidin-4-one | C | 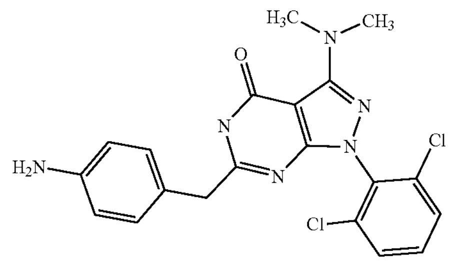 [SMILES: CN(C)c1nn(-c2c(Cl)cccc2Cl)c2nc(Cc3ccc(N)cc3)[nH]c(=O)c12] |
| 17 | 1-(2,6-Dichloro-phenyl)-3-dimethylamino-6-(3-methoxy-benzyl)-1,5-dihydro-pyrazolo[3,4-d]pyrimidin-4-one | C | 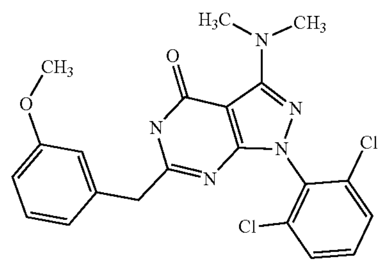 [SMILES: COc1cccc(Cc2nc3c(c(N(C)C)nn3-c3c(Cl)cccc3Cl)c(=O)[nH]2)c1] |
| 18 | 6-(3,4-Dichloro-benzyl)-1-(2,6-dichloro-phenyl)-3-dimethylamino-1,5-dihydro-pyrazolo[3,4-d]pyrimidin-4-one | C | 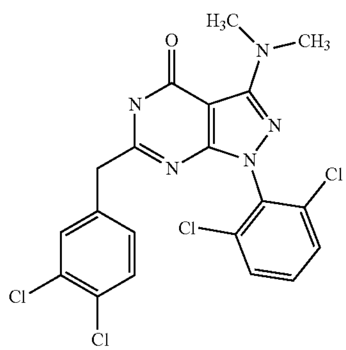 [SMILES: CN(C)c1nn(-c2c(Cl)cccc2Cl)c2nc(Cc3ccc(Cl)c(Cl)c3)[nH]c(=O)c12] |
| 19 | 6-(3-Bromo-4-hydroxy-benzyl)-1-(2,6-dichloro-phenyl)-3-dimethylamino-1,5-dihydro-pyrazolo[3,4-d]pyrimidin-4-one | C | 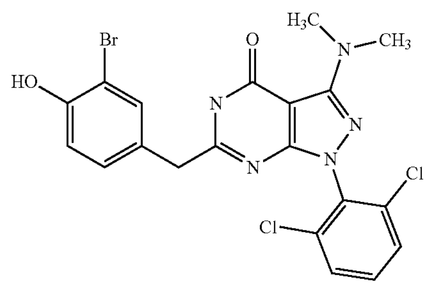 [SMILES: CN(C)c1nn(-c2c(Cl)cccc2Cl)c2nc(Cc3ccc(O)c(Br)c3)[nH]c(=O)c12] |
| 20 | 1-(2,6-Dichloro-phenyl)-3-dimethylamino-6-(3-methyl-benzyl)-1,5-dihydro-pyrazolo[3,4-d]pyrimidin-4-one | C | 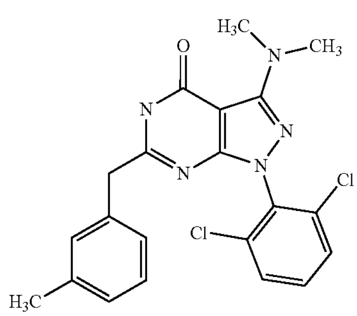 [SMILES: Cc1cccc(Cc2nc3c(c(N(C)C)nn3-c3c(Cl)cccc3Cl)c(=O)[nH]2)c1] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 21 | 3,5-Dichloro-4-[3-dimethylamino-6-(3-hydroxy-benzyl)-4-oxo-4,5-dihydro-pyrazolo[3,4-d]pyrimidin-1-yl]-benzenesulfonamide | C | 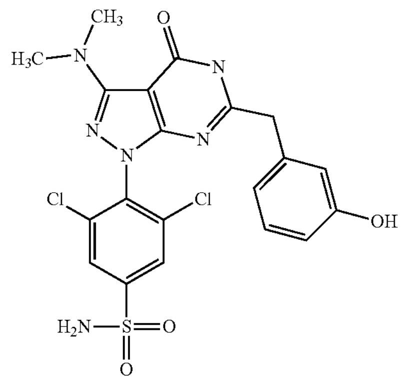 [SMILES: CN(C)c1nn(-c2c(Cl)cc(S(N)(=O)=O)cc2Cl)c2nc(Cc3cccc(O)c3)[nH]c(=O)c12] |
| 22 | 3,5-Dichloro-4-[3-dimethylamino-4-oxo-6-(4-[1,2,4]triazol-1-ylmethyl-benzyl)-4,5-dihydro-pyrazolo[3,4-d]pyrimidin-1-yl]-benzenesulfonamide | C | 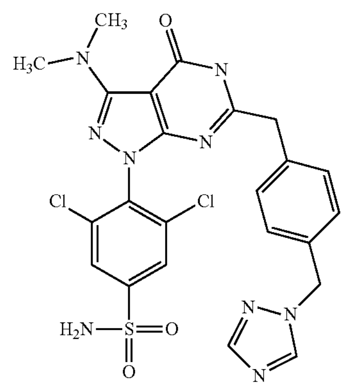 [SMILES: CN(C)c1nn(-c2c(Cl)cc(S(N)(=O)=O)cc2Cl)c2nc(Cc3ccc(Cn4cncn4)cc3)[nH]c(=O)c12] |
| 23 | N-{3-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl}-acetamide | F | 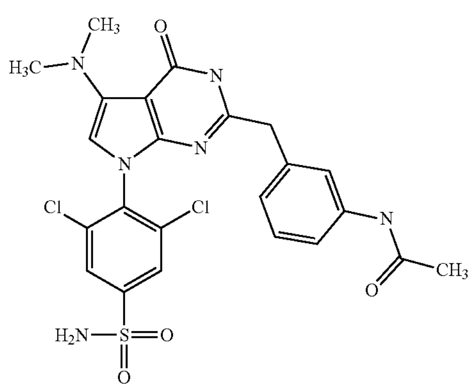 [SMILES: CC(=O)Nc1cccc(Cc2nc3c(c(N(C)C)cn3-c3c(Cl)cc(S(N)(=O)=O)cc3Cl)c(=O)[nH]2)c1] |
| 24 | 3,5-Dichloro-4-[3-dimethylamino-4-oxo-6-(3-oxo-3,4-dihydro-2H-benzo[1,4]oxazin-6-ylmethyl)-4,5-dihydro-pyrazolo[3,4-d]pyrimidin-1-yl]-benzenesulfonamide | C | 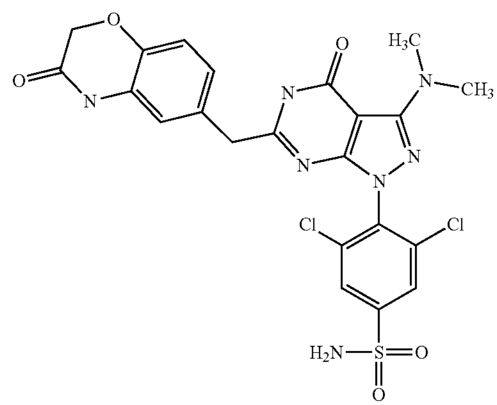 [SMILES: CN(C)c1nn(-c2c(Cl)cc(S(N)(=O)=O)cc2Cl)c2nc(Cc3ccc4c(c3)NC(=O)CO4)[nH]c(=O)c12] |

TABLE 1-continued

Compounds of the invention
Compounds No. 1 to 5 and 7 to 9 are intermediate compounds according to the present invention.

| No. | Name | General method | Structure |
|---|---|---|---|
| 25 | 3,5-Dichloro-4-[3-dimethylamino-4-oxo-6-(4-pyrazol-1-ylmethyl-benzyl)-4,5-dihydro-pyrazolo[3,4-d]pyrimidin-1-yl]-benzenesulfonamide | C | 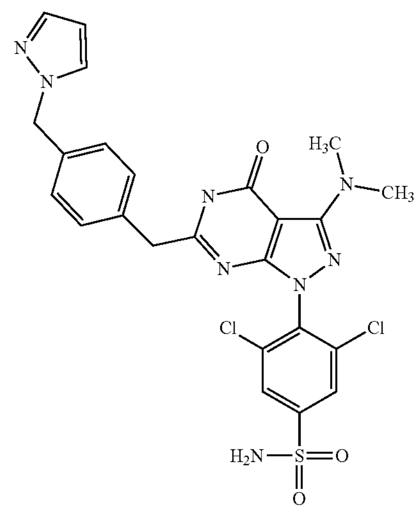 [SMILES: CN(C)c1nn(-c2c(Cl)cc(S(N)(=O)=O)cc2Cl)c2nc(Cc3ccc(Cn4cccn4)cc3)[nH]c(=O)c12] |
| 26 | 3,5-Dichloro-4-(3-dimethylamino-6-{4-[4-(2-methoxy-phenyl)-piperazin-1-ylmethyl]-benzyl}-4-oxo-4,5-dihydro-pyrazolo[3,4-d]pyrimidin-1-yl)-benzenesulfonamide | C | 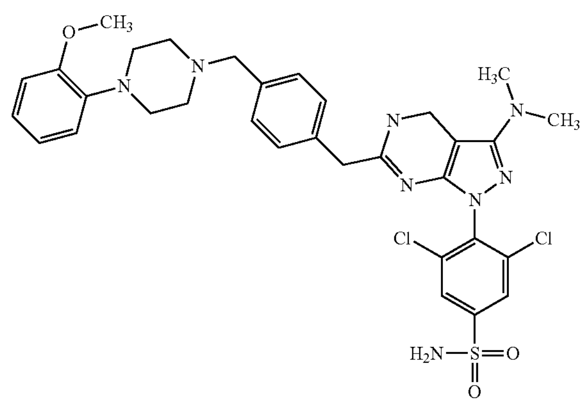 [SMILES: COc1ccccc1N1CCN(Cc2ccc(CC3=Nc4c(c(N(C)C)nn4-c4c(Cl)cc(S(N)(=O)=O)cc4Cl)CN3)cc2)CC1] |
| 27 | 3,5-Dichloro-4-[3-dimethylamino-6-(3-fluoro-benzyl)-4-oxo-4,5-dihydro-pyrazolo[3,4-d]pyrimidin-1-yl]-benzenesulfonamide | C | 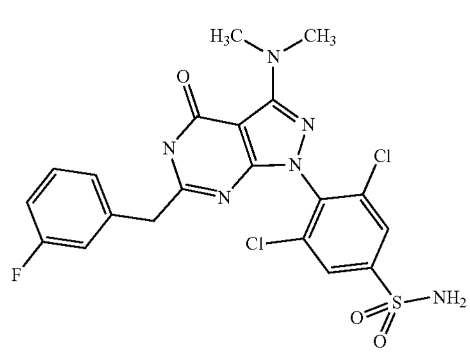 [SMILES: CN(C)c1nn(-c2c(Cl)cc(S(N)(=O)=O)cc2Cl)c2nc(Cc3cccc(F)c3)[nH]c(=O)c12] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 28 | 1-(2,6-Dichloro-phenyl)-3-dimethylamino-6-pyridin-3-ylmethyl-1,5-dihydro-pyrazolo[3,4-d]pyrimidin-4-one | C | 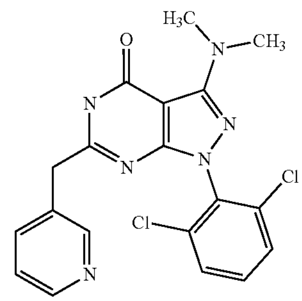 [SMILES: CN(C)c1nn(-c2c(Cl)cccc2Cl)c2nc(Cc3cccnc3)[nH]c(=O)c12] |
| 29 | 6-(5-Bromo-pyridin-3-ylmethyl)-1-(2,6-dichloro-phenyl)-3-dimethylamino-1,5-dihydro-pyrazolo[3,4-d]pyrimidin-4-one | C | 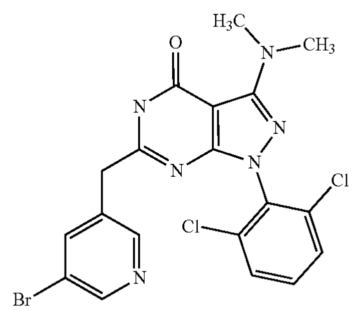 [SMILES: CN(C)c1nn(-c2c(Cl)cccc2Cl)c2nc(Cc3cncc(Br)c3)[nH]c(=O)c12] |
| 30 | 4-[6-(4-Butoxy-benzyl)-3-dimethylamino-4-oxo-4,5-dihydro-pyrazolo[3,4-d]pyrimidin-1-yl]-3,5-dichloro-benzenesulfonamide | C | 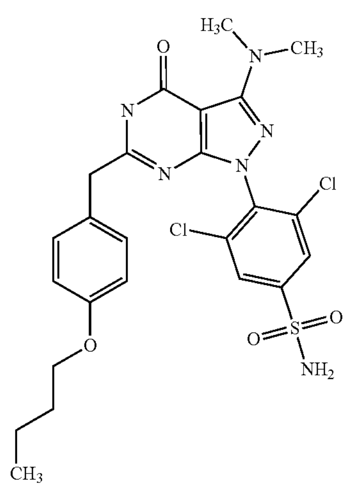 [SMILES: CCCCOc1ccc(Cc2nc3c(c(N(C)C)nn3-c3c(Cl)cc(S(N)(=O)=O)cc3Cl)c(=O)[nH]2)cc1] |
| 31 | 4-(6-Benzo[1,3]dioxol-5-ylmethyl-3-dimethylamino-4-oxo-4,5-dihydro-pyrazolo[3,4-d]pyrimidin-1-yl)-3,5-dichloro-benzenesulfonamide | C | 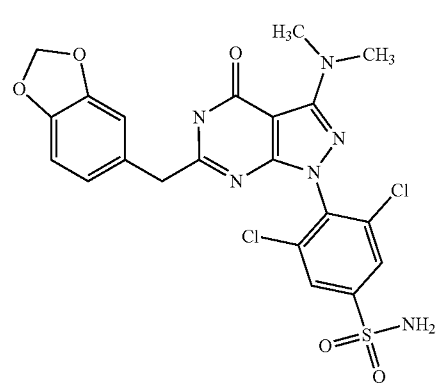 [SMILES: CN(C)c1nn(-c2c(Cl)cc(S(N)(=O)=O)cc2Cl)c2nc(Cc3ccc4c(c3)OCO4)[nH]c(=O)c12] |

TABLE 1-continued

Compounds of the invention
Compounds No. 1 to 5 and 7 to 9 are intermediate compounds according to the present invention.

| No. | Name | General method | Structure |
|---|---|---|---|
| 32 | 3,5-Dichloro-4-[6-(3,4-dichloro-benzyl)-3-dimethylamino-4-oxo-4,5-dihydro-pyrazolo[3,4-d]pyrimidin-1-yl]-benzenesulfonamide | C | 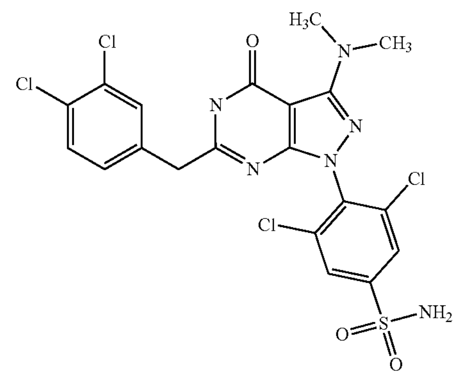 [SMILES: CN(C)c1nn(-c2c(Cl)cc(S(N)(=O)=O)cc2Cl)c2nc(Cc3ccc(Cl)c(Cl)c3)[nH]c(=O)c12] |
| 33 | 6-Benzo[1,3]dioxol-5-ylmethyl-1-(2,3-difluoro-6-methoxy-phenyl)-3-dimethylamino-1,5-dihydro-pyrazolo[3,4-d]pyrimidin-4-one | C | 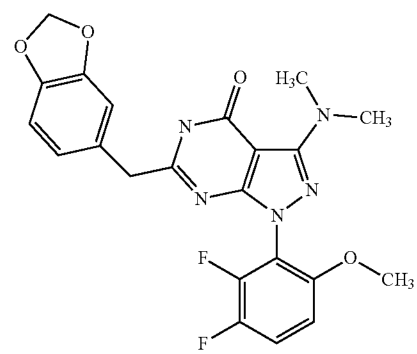 [SMILES: COc1ccc(F)c(F)c1-n1nc(N(C)C)c2c(=O)[nH]c(Cc3ccc4c(c3)OCO4)nc21] |
| 34 | 4-[6-(5-Bromo-pyridin-3-ylmethyl)-3-dimethylamino-4-oxo-4,5-dihydro-pyrazolo[3,4-d]pyrimidin-1-yl]-3,5-dichloro-benzenesulfonamide | C | 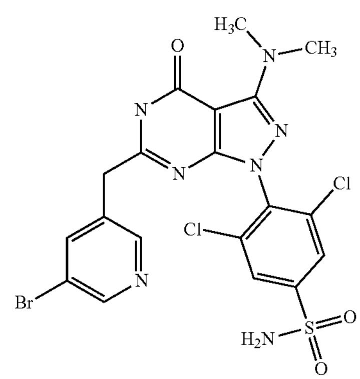 [SMILES: CN(C)c1nn(-c2c(Cl)cc(S(N)(=O)=O)cc2Cl)c2nc(Cc3cncc(Br)c3)[nH]c(=O)c12] |
| 35 | 3,5-Dichloro-4-[3-dimethylamino-6-(4-methoxy-benzyl)-4-oxo-4,5-dihydro-pyrazolo[3,4-d]pyrimidin-1-yl]-benzenesulfonamide | C | 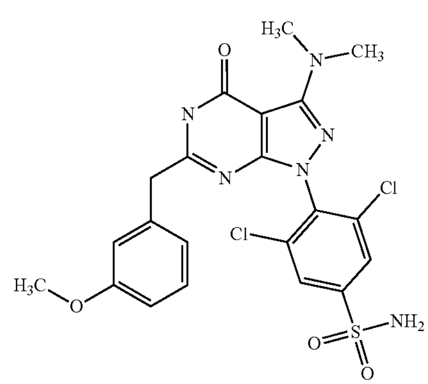 [SMILES: COc1cccc(Cc2nc3c(c(N(C)C)nn3-c3c(Cl)cc(S(N)(=O)=O)cc3Cl)c(=O)[nH]2)c1] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 36 | 3,5-Dichloro-4-(3-dimethylamino-4-oxo-6-thiophen-2-ylmethyl-4,5-dihydro-pyrazolo[3,4-d]pyrimidin-1-yl)-benzenesulfonamide | C | 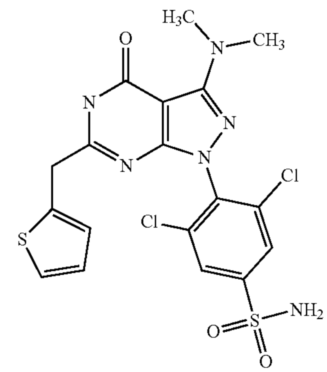 [SMILES: CN(C)c1nn(-c2c(Cl)cc(S(N)(=O)=O)cc2Cl)c2nc(Cc3cccs3)[nH]c(=O)c12] |
| 37 | 3,5-Dichloro-4-[3-dimethylamino-4-oxo-6-(2-oxo-2,3-dihydro-benzooxazol-5-ylmethyl)-4,5-dihydro-pyrazolo[3,4-d]pyrimidin-1-yl]-benzenesulfonamide | C | 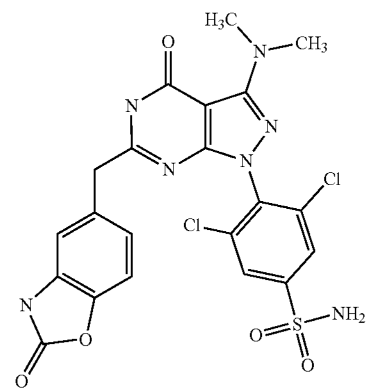 [SMILES: CN(C)c1nn(-c2c(Cl)cc(S(N)(=O)=O)cc2Cl)c2nc(Cc3ccc4oc(=O)[nH]c4c3)[nH]c(=O)c12] |
| 38 | 1-(2,3-Difluoro-6-methoxy-phenyl)-3-dimethylamino-6-thiophen-2-ylmethyl-1,5-dihydro-pyrazolo[3,4-d]pyrimidin-4-one | C | 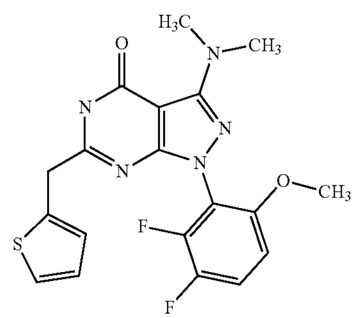 [SMILES: COc1ccc(F)c(F)c1-n1nc(N(C)C)c2c(=O)[nH]c(Cc3cccs3)nc21] |
| 39 | 4-[6-(3-Bromo-4-hydroxy-benzyl)-3-dimethylamino-4-oxo-4,5-dihydro-pyrazolo[3,4-d]pyrimidin-1-yl]-3,5-dichloro-benzenesulfonamide | C | 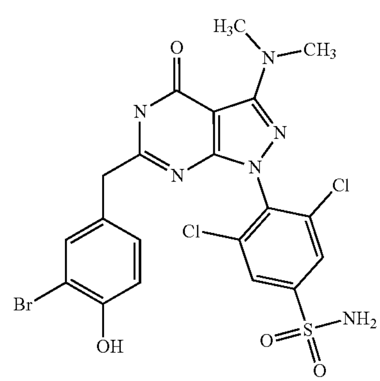 [SMILES: CN(C)c1nn(-c2c(Cl)cc(S(N)(=O)=O)cc2Cl)c2nc(Cc3ccc(O)c(Br)c3)[nH]c(=O)c12] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 40 | 4-[6-(4-Bromo-benzyl)-3-dimethylamino-4-oxo-4,5-dihydro-pyrazolo[3,4-d]pyrimidin-1-yl]-3,5-dichloro-benzenesulfonamide | C | 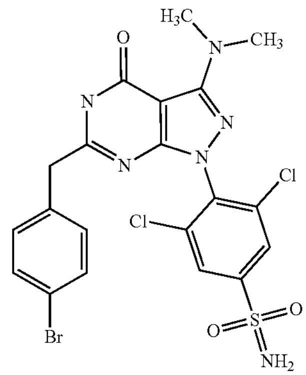 |
| 41 | 3,5-Dichloro-4-[3-dimethylamino-6-(4-methoxy-3-nitro-benzyl)-4-oxo-4,5-dihydro-pyrazolo[3,4-d]pyrimidin-1-yl]-benzenesulfonamide | C | 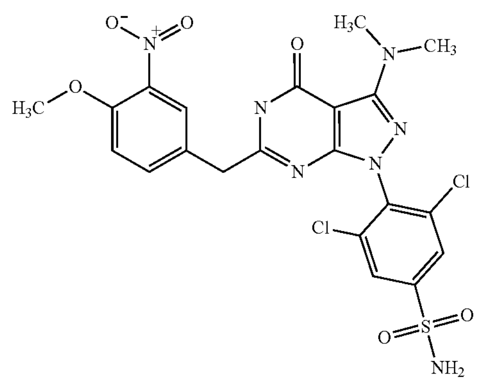 |
| 42 | 3,5-Dichloro-4-[3-dimethylamino-6-(3,4-dimethyl-benzyl)-4-oxo-4,5-dihydro-pyrazolo[3,4-d]pyrimidin-1-yl]-benzenesulfonamide | C | 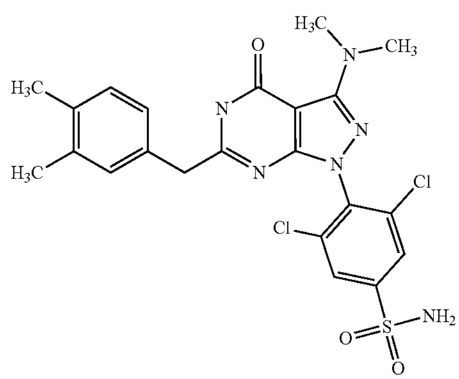 [SMILES: Cc1ccc(Cc2nc3c(c(N(C)C)nn3-c3c(Cl)cc(S(N)(=O)=O)cc3Cl)c(=O)[nH]2)cc1C] |
| 43 | 1-(2,6-Dichloro-phenyl)-3-dimethylamino-6-thiophen-2-ylmethyl-1,5-dihydro-pyrazolo[3,4-d]pyrimidin-4-one | C | 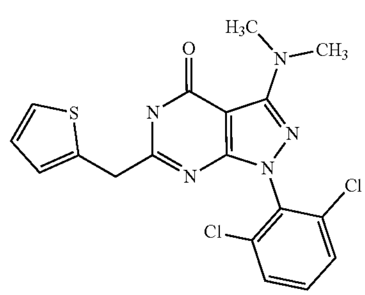 [SMILES: CN(C)c1nn(-c2c(Cl)cccc2Cl)c2nc(Cc3cccs3)[nH]c(=O)c12] |

TABLE 1-continued

Compounds of the invention
Compounds No. 1 to 5 and 7 to 9 are intermediate compounds according to the present invention.

| No. | Name | General method | Structure |
|---|---|---|---|
| 44 | 1-(2,6-Dichloro-phenyl)-3-dimethylamino-6-(3-methyl-isoxazol-5-ylmethyl)-1,5-dihydro-pyrazolo[3,4-d]pyrimidin-4-one | C | 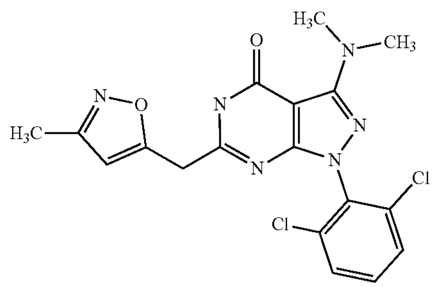 [SMILES: Cc1cc(Cc2nc3c(c(N(C)C)nn3-c3c(Cl)cccc3Cl)c(=O)[nH]2)on1] |
| 45 | 3,5-Dichloro-4-[3-dimethylamino-6-(4-fluoro-benzyl)-4-oxo-4,5-dihydro-pyrazolo[3,4-d]pyrimidin-1-yl]-benzenesulfonamide | C | 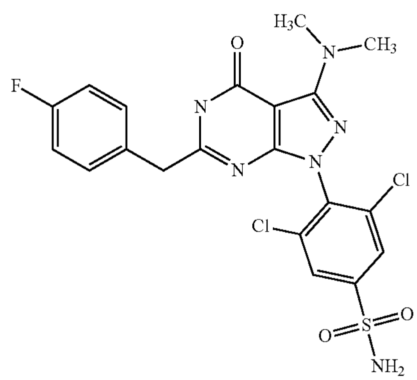 [SMILES: CN(C)c1nn(-c2c(Cl)cc(S(N)(=O)=O)cc2Cl)c2nc(Cc3ccc(F)cc3)[nH]c(=O)c12] |
| 46 | 3,5-Dichloro-4-[3-dimethylamino-6-(2-methoxy-pyridin-4-ylmethyl)-4-oxo-4,5-dihydro-pyrazolo[3,4-d]pyrimidin-1-yl]-benzenesulfonamide | C | 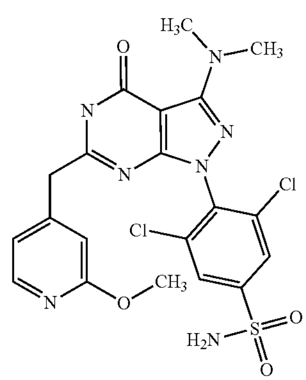 [SMILES: COc1cc(Cc2nc3c(c(N(C)C)nn3-c3c(Cl)cc(S(N)(=O)=O)cc3Cl)c(=O)[nH]2)ccn1] |
| 47 | 3,5-Dichloro-4-[3-dimethylamino-6-(5-methoxy-pyridin-3-ylmethyl)-4-oxo-4,5-dihydro-pyrazolo[3,4-d]pyrimidin-1-yl]-benzenesulfonamide | C | 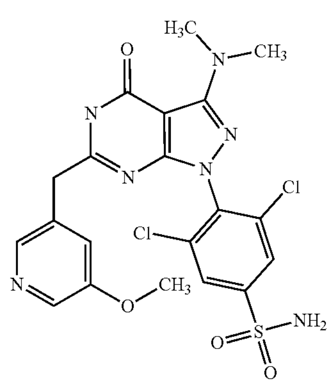 [SMILES: COc1cncc(Cc2nc3c(c(N(C)C)nn3-c3c(Cl)cc(S(N)(=O)=O)cc3Cl)c(=O)[nH]2)c1] |

TABLE 1-continued

Compounds of the invention
Compounds No. 1 to 5 and 7 to 9 are intermediate compounds according to the present invention.

| No. | Name | General method | Structure |
|---|---|---|---|
| 48 | 4-[6-(3-Amino-4-fluoro-benzyl)-3-dimethylamino-4-oxo-4,5-dihydro-pyrazolo[3,4-d]pyrimidin-1-yl]-3,5-dichloro-benzenesulfonamide | C | 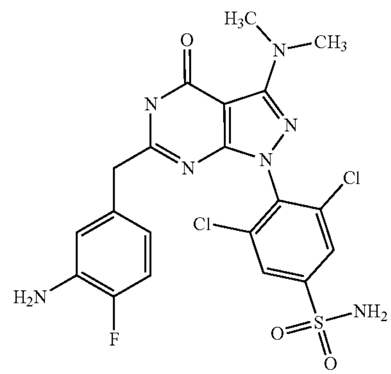 [SMILES: CN(C)c1nn(-c2c(Cl)cc(S(N)(=O)=O)cc2Cl)c2nc(Cc3ccc(F)c(N)c3)[nH]c(=O)c12] |
| 49 | 4-[6-(2-Amino-thiazol-4-ylmethyl)-3-dimethylamino-4-oxo-4,5-dihydro-pyrazolo[3,4-d]pyrimidin-1-yl]-3,5-dichloro-benzenesulfonamide | C | 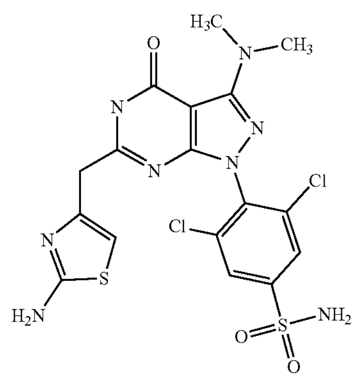 [SMILES: CN(C)c1nn(-c2c(Cl)cc(S(N)(=O)=O)cc2Cl)c2nc(Cc3csc(N)n3)[nH]c(=O)c12] |
| 50 | 3,5-Dichloro-4-[3-dimethylamino-6-(3-methyl-benzyl)-4-oxo-4,5-dihydro-pyrazolo[3,4-d]pyrimidin-1-yl]-benzenesulfonamide | C | 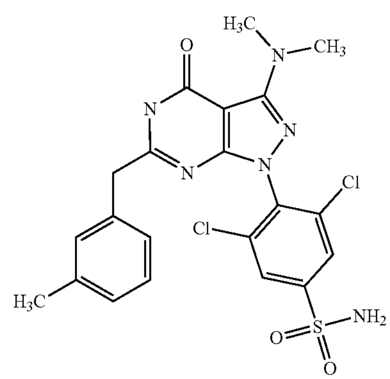 [SMILES: Cc1cccc(Cc2nc3c(c(N(C)C)nn3-c3c(Cl)cc(S(N)(=O)=O)cc3Cl)c(=O)[nH]2)c1] |
| 51 | 4-[6-(3-Amino-4-methoxy-benzyl)-3-dimethylamino-4-oxo-4,5-dihydro-pyrazolo[3,4-d]pyrimidin-1-yl]-3,5-dichloro-benzenesulfonamide | C | 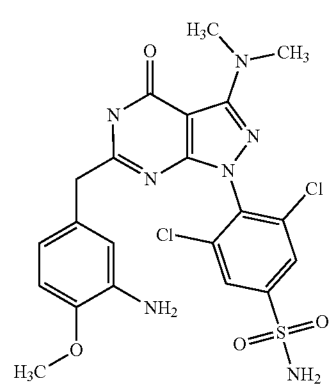 [SMILES: COc1ccc(Cc2nc3c(c(N(C)C)nn3-c3c(Cl)cc(S(N)(=O)=O)cc3Cl)c(=O)[nH]2)cc1N] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 52 | 1-(2,3-Difluoro-6-methoxy-phenyl)-3-dimethylamino-6-(3-methyl-benzyl)-1,5-dihydro-pyrazolo[3,4-d]pyrimidin-4-one | C | 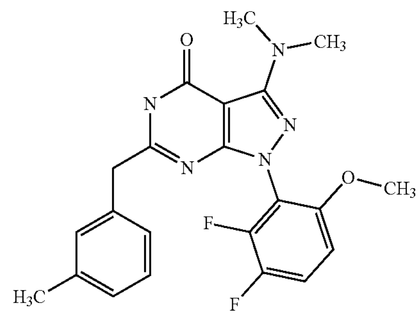 |
| 53 | 3,5-Dichloro-4-[3-dimethylamino-6-(4-methyl-thiazol-2-ylmethyl)-4-oxo-4,5-dihydro-pyrazolo[3,4-d]pyrimidin-1-yl]-benzenesulfonamide | C | 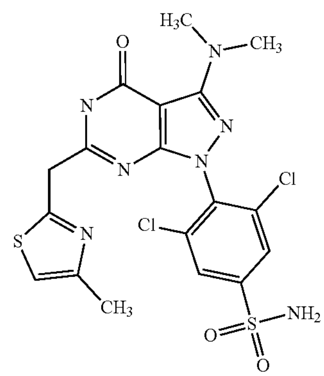 [SMILES: Cc1csc(Cc2nc3c(c(N(C)C)nn3-c3c(Cl)cc(S(N)(=O)=O)cc3Cl)c(=O)[nH]2)n1] |
| 54 | 1-(2,6-Dichloro-phenyl)-3-dimethylamino-6-(4-methyl-thiazol-2-ylmethyl)-1,5-dihydro-pyrazolo[3,4-d]pyrimidin-4-one | C | 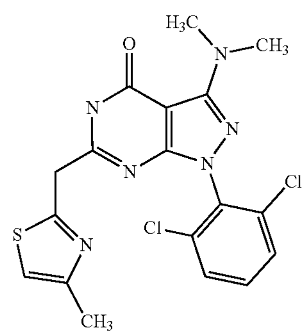 [SMILES: Cc1csc(Cc2nc3c(c(N(C)C)nn3-c3c(Cl)cccc3Cl)c(=O)[nH]2)n1] |
| 55 | 3,5-Dichloro-4-(6-[difluoro-(4-methoxy-phenyl)-methyl]-3-dimethylamino-4-oxo-4,5-dihydro-pyrazolo[3,4-d]pyrimidin-1-yl)-benzenesulfonamide | C | 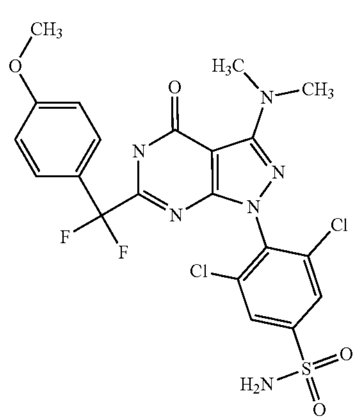 [SMILES: COc1ccc(C(F)(F)c2nc3c(c(N(C)C)nn3-c3c(Cl)cc(S(N)(=O)=O)cc3Cl)c(=O)[nH]2)cc1] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 56 | 3,5-Dichloro-4-(6-[difluoro-(3-fluoro-phenyl)-methyl]-3-dimethylamino-4-oxo-4,5-dihydro-pyrazolo[3,4-d]pyrimidin-1-yl)-benzenesulfonamide | C | 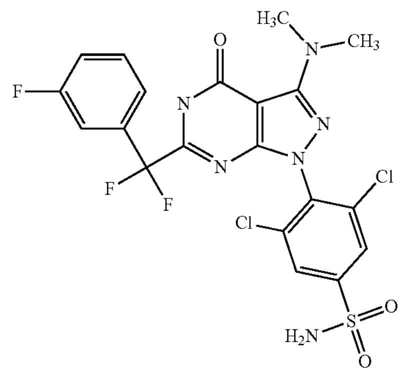 [SMILES: CN(C)c1nn(-c2c(Cl)cc(S(N)(=O)=O)cc2Cl)c2nc(C(F)(F)c3cccc(F)c3)[nH]c(=O)c12] |
| 57 | 1-(2,3-Difluoro-6-methoxy-phenyl)-3-dimethylamino-6-(4-methyl-thiazol-2-ylmethyl)-1,5-dihydro-pyrazolo[3,4-d]pyrimidin-4-one | C | 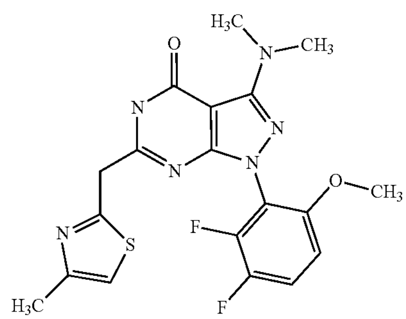 |
| 58 | 1-(2,6-Dichloro-phenyl)-3-dimethylamino-6-(5-methoxy-pyridin-3-ylmethyl)-1,5-dihydro-pyrazolo[3,4-d]pyrimidin-4-one | C | 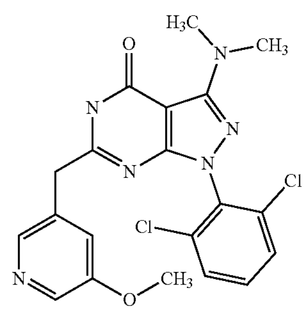 [SMILES: COc1cncc(Cc2nc3c(c(N(C)C)nn3-c3c(Cl)cccc3Cl)c(=O)[nH]2)c1] |
| 59 | 3,5-Dichloro-4-[6-(3,4-dimethoxy-benzyl)-3-dimethylamino-4-oxo-4,5-dihydro-pyrazolo[3,4-d]pyrimidin-1-yl]-benzenesulfonamide | C | 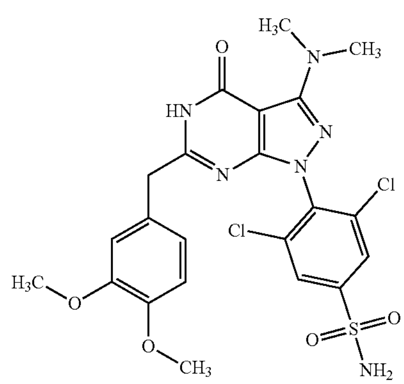 [SMILES: COc1ccc(Cc2nc3c(c(N(C)C)nn3-c3c(Cl)cc(S(N)(=O)=O)cc3Cl)c(=O)[nH]2)cc1OC] |

TABLE 1-continued

Compounds of the invention
Compounds No. 1 to 5 and 7 to 9 are intermediate compounds according to the present invention.

| No. | Name | General method | Structure |
|---|---|---|---|
| 60 | 3,5-Dichloro-4-(3-dimethylamino-4-oxo-6-[4-(3-phenyl-ureido)-benzyl]-4,5-dihydro-pyrazolo[3,4-d]pyrimidin-1-yl)-benzenesulfonamide | E | 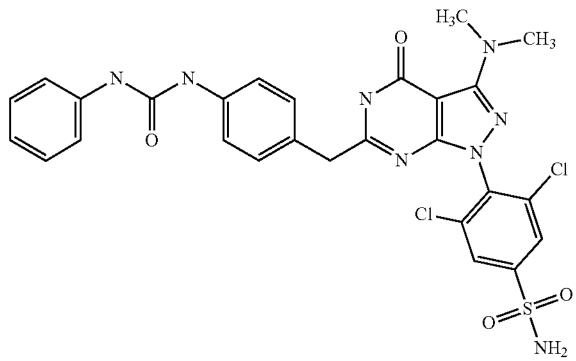 [SMILES: CN(C)c1nn(-c2c(Cl)cc(S(N)(=O)=O)cc2Cl)c2nc(Cc3ccc(NC(=O)Nc4ccccc4)cc3)[nH]c(=O)c12] |
| 61 | 3,5-Dichloro-4-[3-dimethylamino-6-(4-methanesulfonylamino-benzyl)-4-oxo-4,5-dihydro-pyrazolo[3,4-d]pyrimidin-1-yl]-benzenesulfonamide | F | 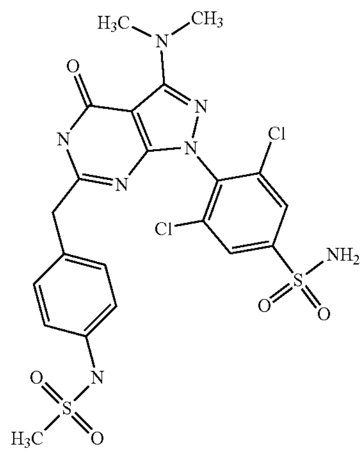 [SMILES: CN(C)c1nn(-c2c(Cl)cc(S(N)(=O)=O)cc2Cl)c2nc(Cc3ccc(NS(C)(=O)=O)cc3)[nH]c(=O)c12] |
| 62 | N-{4-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl}-acetamide | F | 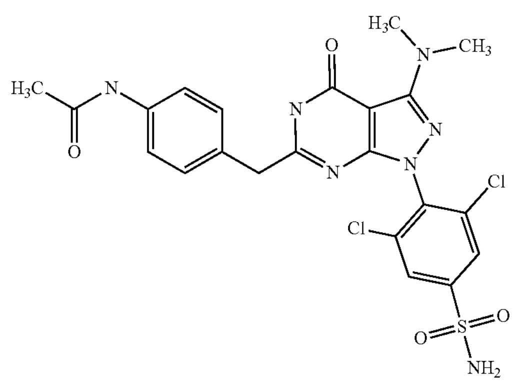 [SMILES: CC(=O)Nc1ccc(Cc2nc3c(c(N(C)C)nn3-c3c(Cl)cc(S(N)(=O)=O)cc3Cl)c(=O)[nH]2)cc1] |
| 63 | 3,5-Dichloro-4-[3-dimethylamino-6-(3-methanesulfonylamino-benzyl)-4-oxo-4,5-dihydro-pyrazolo[3,4-d]pyrimidin-1-yl]-benzenesulfonamide | F | 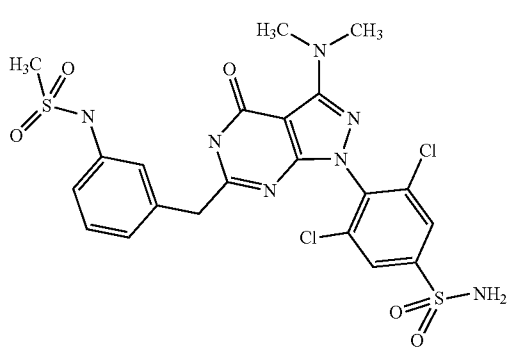 [SMILES: CN(C)c1nn(-c2c(Cl)cc(S(N)(=O)=O)cc2Cl)c2nc(Cc3cccc(NS(C)(=O)=O)c3)[nH]c(=O)c12] |

TABLE 1-continued

Compounds of the invention
Compounds No. 1 to 5 and 7 to 9 are intermediate compounds according to the present invention.

| No. | Name | General method | Structure |
|---|---|---|---|
| 64 | 4-{6-[3-(3-Benzyl-ureido)-benzyl]-3-dimethylamino-4-oxo-4,5-dihydro-pyrazolo[3,4-d]pyrimidin-1-yl}-3,5-dichloro-benzenesulfonamide | E | 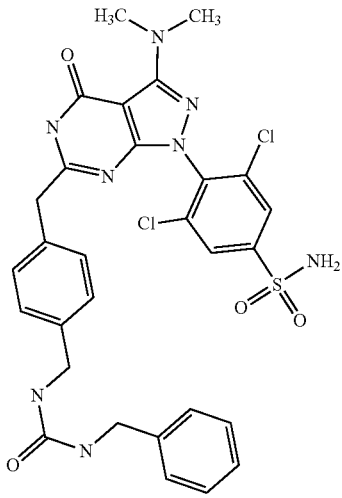 [SMILES: CN(C)c1nn(-c2c(Cl)cc(S(N)(=O)=O)cc2Cl)c2nc(Cc3ccc(CNC(=O)NCc4ccccc4)cc3)[nH]c(=O)c12] |
| 65 | 4-{6-[4-(3-Benzyl-ureido)-benzyl]-3-dimethylamino-4-oxo-4,5-dihydro-pyrazolo[3,4-d]pyrimidin-1-yl}-3,5-dichloro-benzenesulfonamide | E | 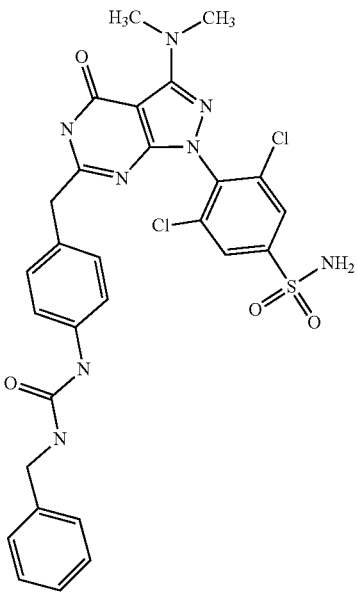 [SMILES: CN(C)c1nn(-c2c(Cl)cc(S(N)(=O)=O)cc2Cl)c2nc(Cc3ccc(NC(=O)NCc4ccccc4)cc3)[nH]c(=O)c12] |
| 66 | 1-(2,3-Difluoro-6-methoxy-phenyl)-3-dimethylamino-6-(4-pyridin-3-yl-benzyl)-1,5-dihydro-pyrazolo[3,4-d]pyrimidin-4-one | D | 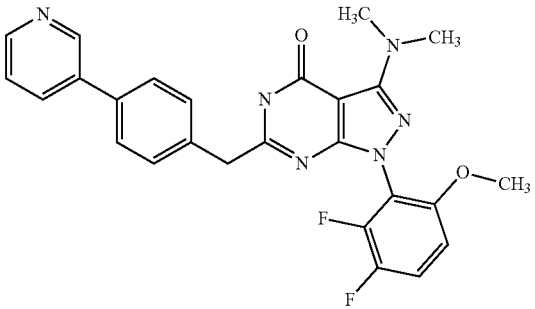 [SMILES: COc1ccc(F)c(F)c1-n1nc(N(C)C)c2c(=O)[nH]c(Cc3ccc(-c4cccnc4)cc3)nc21] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 67 | 3,5-Dichloro-4-[3-dimethylamino-4-oxo-6-(4-pyridin-3-yl-benzyl)-4,5-dihydro-pyrazolo[3,4-d]pyrimidin-1-yl]-benzenesulfonamide | D | 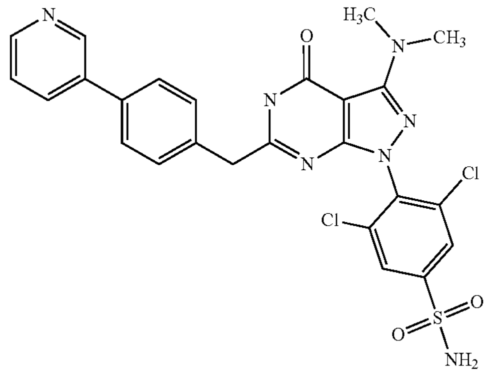 [SMILES: CN(C)c1nn(-c2c(Cl)cc(S(N)(=O)=O)cc2Cl)c2nc(Cc3ccc(-c4cccnc4)cc3)[nH]c(=O)c12] |
| 68 | 3,5-Dichloro-4-[3-dimethylamino-6-(2-hydroxy-pyridin-4-ylmethyl)-4-oxo-4,5-dihydro-pyrazolo[3,4-d]pyrimidin-1-yl]-benzenesulfonamide | C | 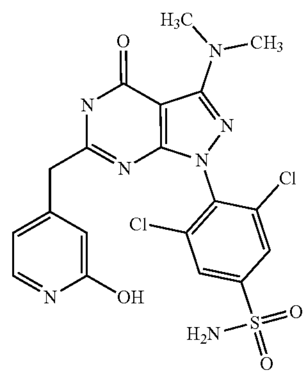 [SMILES: CN(C)c1nn(-c2c(Cl)cc(S(N)(=O)=O)cc2Cl)c2nc(Cc3ccnc(O)c3)[nH]c(=O)c12] |
| 69 | 3,5-Dichloro-4-[3-dimethylamino-6-(5-hydroxy-pyridin-3-ylmethyl)-4-oxo-4,5-dihydro-pyrazolo[3,4-d]pyrimidin-1-yl]-benzenesulfonamide | C | 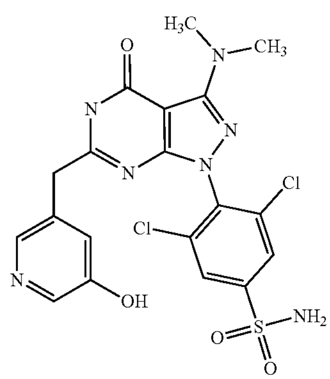 [SMILES: CN(C)c1nn(-c2c(Cl)cc(S(N)(=O)=O)cc2Cl)c2nc(Cc3cncc(O)c3)[nH]c(=O)c12] |
| 70 | N-{5-[1-(2,6-Dichloro-4-sulfamoyl-phenyl)-3-dimethylamino-4-oxo-4,5-dihydro-1H-pyrazolo[3,4-d]pyrimidin-6-ylmethyl]-2-fluoro-phenyl}-acetamide | C | 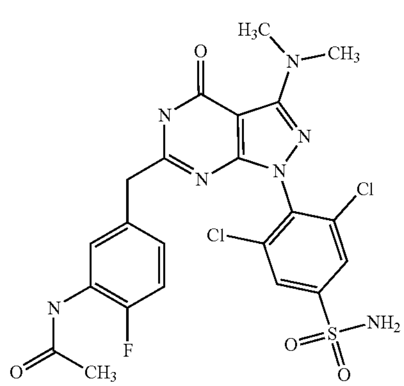 [SMILES: CC(=O)Nc1cc(Cc2nc3c(c(N(C)C)nn3-c3c(Cl)cc(S(N)(=O)=O)cc3Cl)c(=O)[nH]2)ccc1F] |

TABLE 1-continued

Compounds of the invention

Compounds No. 1 to 5 and 7 to 9 are intermediate compounds according to the present invention.

| No. | Name | General method | Structure |
|-----|------|----------------|-----------|
| 71 | N-{4-{1-(2,6-Dichloro-4-sulfamoyl-phenyl)-3-dimethylamino-4-oxo-4,5-dihydro-1H-pyrazolo[3,4-d]pyrimidin-6-ylmethyl]-thiazol-2-yl}-acetamide | C | 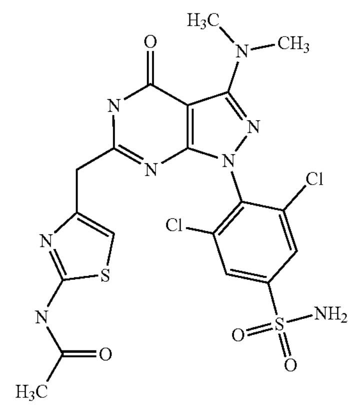 [SMILES: CC(=O)Nc1nc(Cc2nc3c(c(N(C)C)nn3-c3c(Cl)cc(S(N)(=O)=O)cc3Cl)c(=O)[nH]2)cs1] |
| 72 | 3,5-Dichloro-4-{3-dimethylamino-6-[4-(2-methoxy-pyridin-3-yl)-benzyl]-4-oxo-4,5-dihydro-pyrazolo[3,4-d]pyrimidin-1-yl}-benzenesulfonamide | D | 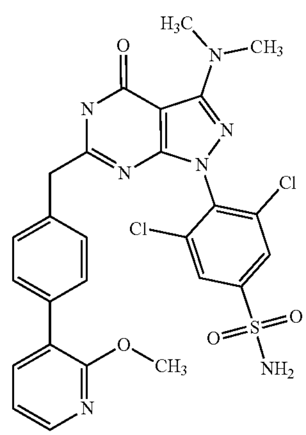 [SMILES: COc1ncccc1-c1ccc(Cc2nc3c(c(N(C)C)nn3-c3c(Cl)cc(S(N)(=O)=O)cc3Cl)c(=O)[nH]2)cc1] |
| 73 | 3,5-Dichloro-4-{6-[4-(2-chloro-pyridin-4-yl)-benzyl]-3-dimethylamino-4-oxo-4,5-dihydro-pyrazolo[3,4-d]pyrimidin-1-yl}-benzenesulfonamide | D | 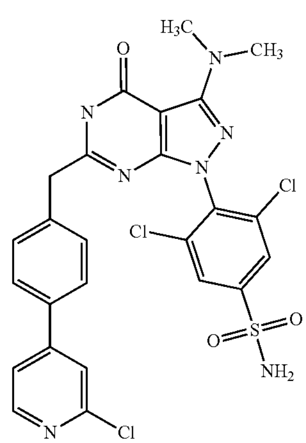 [SMILES: CN(C)c1nn(-c2c(Cl)cc(S(N)(=O)=O)cc2Cl)c2nc(Cc3ccc(-c4ccnc(Cl)c4)cc3)[nH]c(=O)c12] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 74 | 4-Chloro-N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-thiazol-2-yl}-benzamide | C | 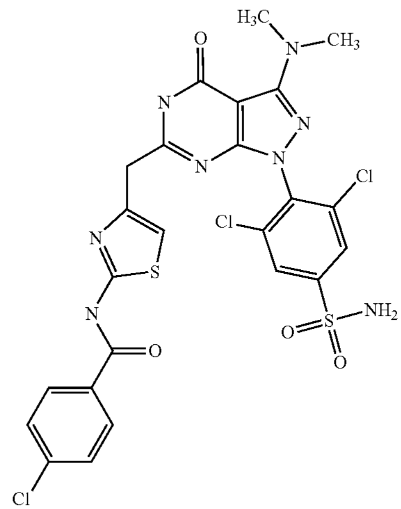 [SMILES: CN(C)c1nn(-c2c(Cl)cc(S(N)(=O)=O)cc2Cl)c2nc(Cc3csc(NC(=O)c4ccc(Cl)cc4)n3)[nH]c(=O)c12] |
| 75 | 4-{6-[3-(3-Benzyl-ureido)-4-methoxy-benzyl]-3-dimethylamino-4-oxo-4,5-dihydro-pyrazolo[3,4-d]pyrimidin-1-yl}-3,5-dichloro-benzenesulfonamide | E | 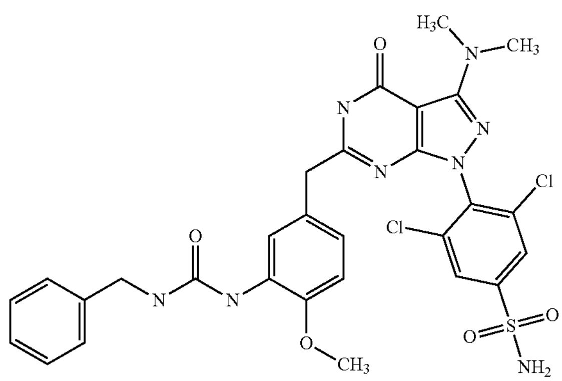 [SMILES: COc1ccc(Cc2nc3c(c(N(C)C)nn3-c3c(Cl)cc(S(N)(=O)=O)cc3Cl)c(=O)[nH]2)cc1NC(=O)NCc1ccccc1] |
| 76 | 3,5-Dichloro-4-(3-dimethylamino-6-{3-[3-(4-fluoro-phenyl)-ureido]-4-methoxy-benzyl}-4-oxo-4,5-dihydro-pyrazolo[3,4-d]pyrimidin-1-yl)-benzenesulfonamide | E | 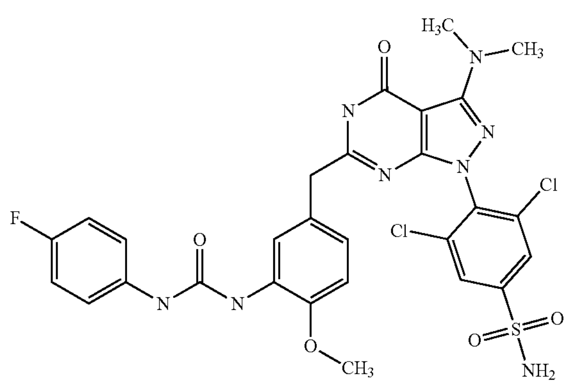 [SMILES: COc1ccc(Cc2nc3c(c(N(C)C)nn3-c3c(Cl)cc(S(N)(=O)=O)cc3Cl)c(=O)[nH]2)cc1NC(=O)Nc1ccc(F)cc1] |

TABLE 1-continued

Compounds of the invention
Compounds No. 1 to 5 and 7 to 9 are intermediate compounds according to the present invention.

| No. | Name | General method | Structure |
|---|---|---|---|
| 77 | N-{5-[1-(2,6-Dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-acetamide | E | 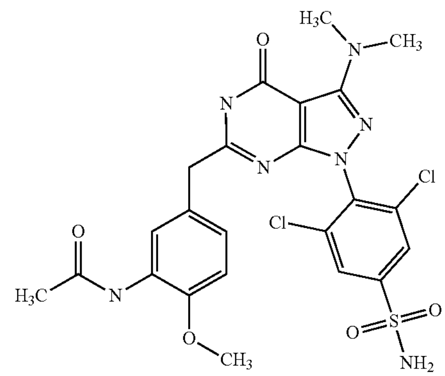 [SMILES: COc1ccc(Cc2nc3c(c(N(C)C)nn3-c3c(Cl)cc(S(N)(=O)=O)cc3Cl)c(=O)[nH]2)cc1NC(C)=O] |
| 78 | 3,5-Dichloro-4-[3-dimethylamino-4-oxo-6-(4-pyridin-4-yl-benzyl)-4,5-dihydro-pyrazolo[3,4-d]pyrimidin-1-yl]-benzenesulfonamide | D | 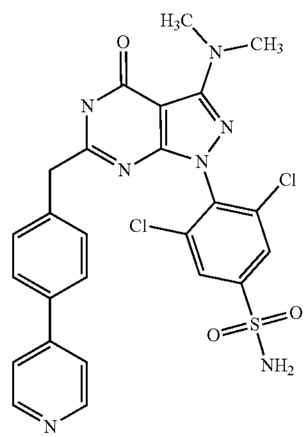 [SMILES: CN(C)c1nn(-c2c(Cl)cc(S(N)(=O)=O)cc2Cl)c2nc(Cc3ccc(-c4ccncc4)cc3)[nH]c(=O)c12] |
| 79 | 3,5-Dichloro-4-[3-dimethylamino-6-(4'-methoxy-biphenyl-4-ylmethyl)-4-oxo-4,5-dihydro-pyrazolo[3,4-d]pyrimidin-1-yl]-benzenesulfonamide | D | 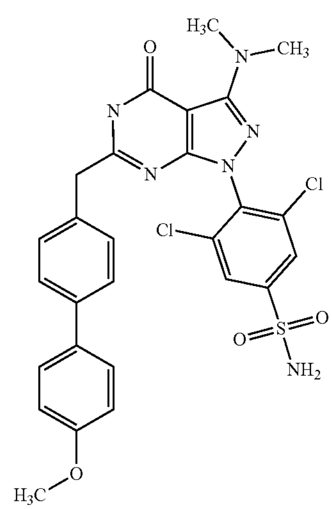 [SMILES: COc1ccc(-c2ccc(Cc3nc4c(c(N(C)C)nn4-c4c(Cl)cc(S(N)(=O)=O)cc4Cl)c(=O)[nH]3)cc2)cc1] |

TABLE 1-continued

Compounds of the invention
Compounds No. 1 to 5 and 7 to 9 are intermediate compounds according to the present invention.

| No. | Name | General method | Structure |
|---|---|---|---|
| 80 | 2-Chloro-N-{5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-acetamide | F | 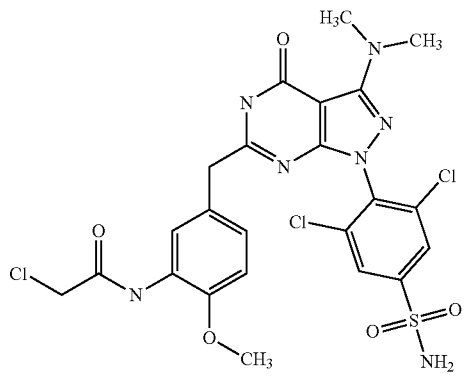 [SMILES: COc1ccc(Cc2nc3c(c(N(C)C)nn3-c3c(Cl)cc(S(N)(=O)=O)cc3Cl)c(=O)[nH]2)cc1NC(=O)CCl] |
| 81 | N-{5-[1-(2,6-Dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-2-morpholin-4-yl-acetamide | C | 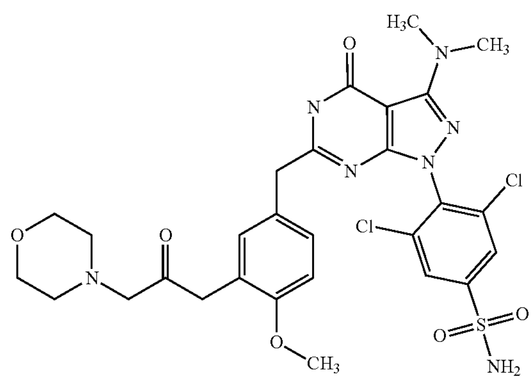 [SMILES: COc1ccc(Cc2nc3c(c(N(C)C)nn3-c3c(Cl)cc(S(N)(=O)=O)cc3Cl)c(=O)[nH]2)cc1CC(=O)CN1CCOCC1] |
| 82 | 3,5-Dichloro-4-[3-dimethylamino-6-(3'-ethylsulfanyl-biphenyl-4-ylmethyl)-4-oxo-4,5-dihydro-pyrazolo[3,4-d]pyrimidin-1-yl]-benzenesulfonamide | D | 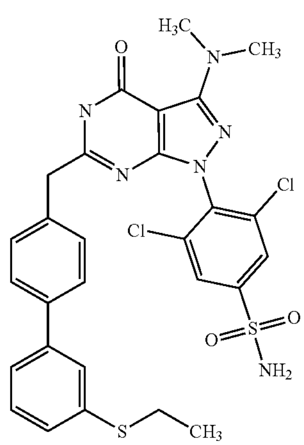 [SMILES: CCSc1cccc(-c2ccc(Cc3nc4c(c(N(C)C)nn4-c4c(Cl)cc(S(N)(=O)=O)cc4Cl)c(=O)[nH]3)cc2)c1] |

TABLE 1-continued

Compounds of the invention
Compounds No. 1 to 5 and 7 to 9 are intermediate compounds according to the present invention.

| No. | Name | General method | Structure |
|---|---|---|---|
| 83 | 3,5-Dichloro-4-[3-dimethylamino-6-(4'-hydroxy-biphenyl-4-ylmethyl)-4-oxo-4,5-dihydro-pyrazolo[3,4-d]pyrimidin-1-yl]-benzenesulfonamide | C | 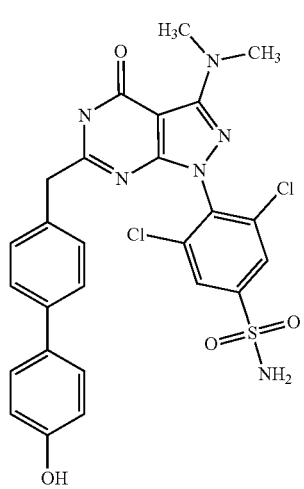 [SMILES: CN(C)c1nn(-c2c(Cl)cc(S(N)(=O)=O)cc2Cl)c2nc(Cc3ccc(-c4ccc(O)cc4)cc3)[nH]c(=O)c12] |
| 84 | 3,5-Dichloro-4-(3-dimethylamino-6-{4-methoxy-3-[3-(4-trifluoromethoxy-phenyl)-ureido]-benzyl}-4-oxo-4,5-dihydro-pyrazolo[3,4-d]pyrimidin-1-yl)-benzenesulfonamide | E | 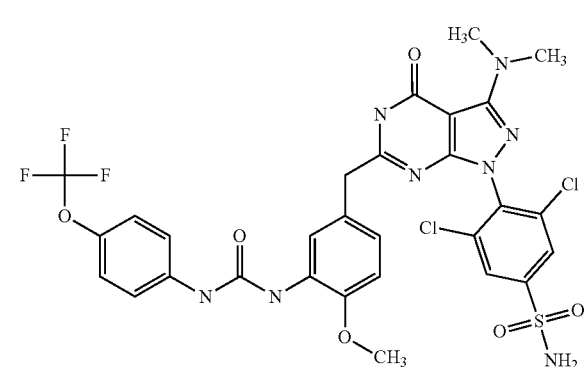 |
| 85 | N-{4-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl}-2-morpholin-4-yl-acetamide | G | 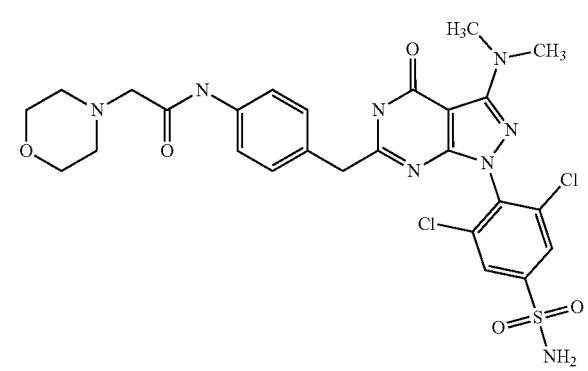 [SMILES: CN(C)c1nn(-c2c(Cl)cc(S(N)(=O)=O)cc2Cl)c2nc(Cc3ccc(NC(=O)CN4CCOCC4)cc3)[nH]c(=O)c12] |

TABLE 1-continued

Compounds of the invention
Compounds No. 1 to 5 and 7 to 9 are intermediate compounds according to the present invention.

| No. | Name | General method | Structure |
|---|---|---|---|
| 86 | N-{4-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl}-2-diethylamino-acetamide | G | 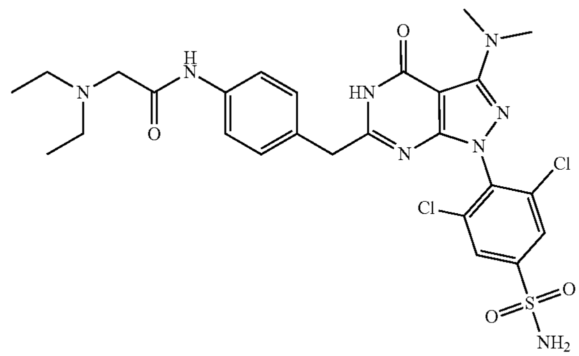 |
| 87 | N-{4-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl}-2-(4-methyl-piperazin-1-yl)-acetamide | G | 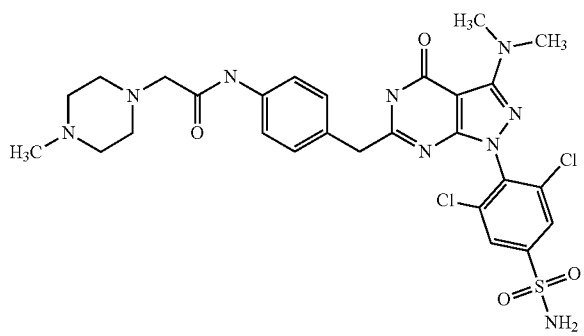 [SMILES: CN1CCN(CC(=O)Nc2ccc(Cc3nc4c(c(N(C)C)nn4-c4c(Cl)cc(S(N)(=O)=O)cc4Cl)c(=O)[nH]3)cc2)CC1] |
| 88 | Cyclopropanecarboxylic acid {5-[1-(2,6-dichloro-4-sulfamoyl-phenyl)-3-dimethylamino-4-oxo-4,5-dihydro-1H-pyrazolo[3,4-d]pyrimidin-6-ylmethyl]-2-methoxy-phenyl}-amide | F | 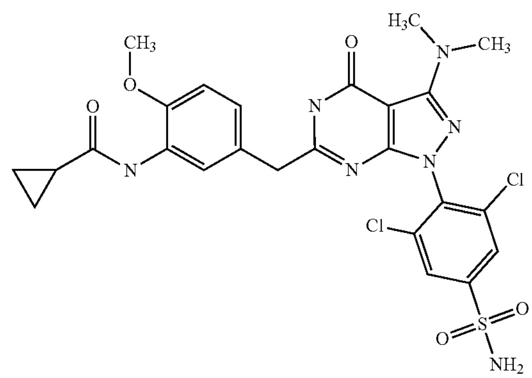 [SMILES: COc1ccc(Cc2nc3c(c(N(C)C)nn3-c3c(Cl)cc(S(N)(=O)=O)cc3Cl)c(=O)[nH]2)cc1NC(=O)C1CC1] |
| 89 | 4'-[1-(2,6-Dichloro-4-sulfamoyl-phenyl)-3-dimethylamino-4-oxo-4,5-dihydro-1H-pyrazolo[3,4-d]pyrimidin-6-ylmethyl]-biphenyl-3-carboxylic acid amide | D | 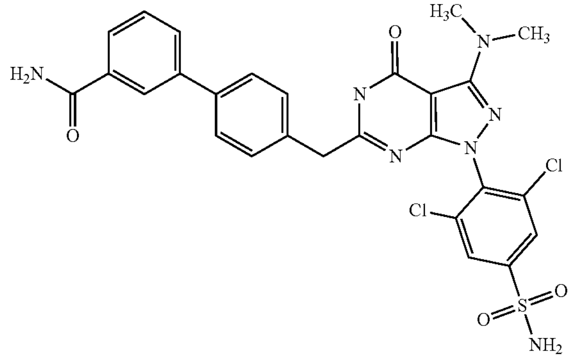 [SMILES: CN(C)c1nn(-c2c(Cl)cc(S(N)(=O)=O)cc2Cl)c2nc(Cc3ccc(-c4cccc(C(N)=O)c4)cc3)[nH]c(=O)c12] |

TABLE 1-continued

Compounds of the invention
Compounds No. 1 to 5 and 7 to 9 are intermediate compounds according to the present invention.

| No. | Name | General method | Structure |
|-----|------|----------------|-----------|
| 90 | 3,5-Dichloro-4-[6-(4'-chloro-biphenyl-4-ylmethyl)-3-dimethylamino-4-oxo-4,5-dihydro-pyrazolo[3,4-d]pyrimidin-1-yl]-benzenesulfonamide | D | 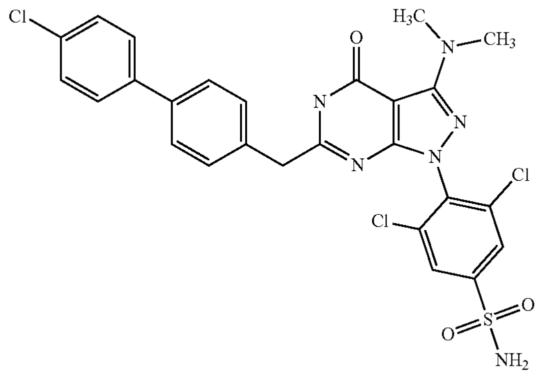 [SMILES: CN(C)c1nn(-c2c(Cl)cc(S(N)(=O)=O)cc2Cl)c2nc(Cc3ccc(-c4ccc(Cl)cc4)cc3)[nH]c(=O)c12] |
| 91 | 3,5-Dichloro-4-[6-(2',4'-difluoro-biphenyl-4-ylmethyl)-3-dimethylamino-4-oxo-4,5-dihydro-pyrazolo[3,4-d]pyrimidin-1-yl]-benzenesulfonamide | D | 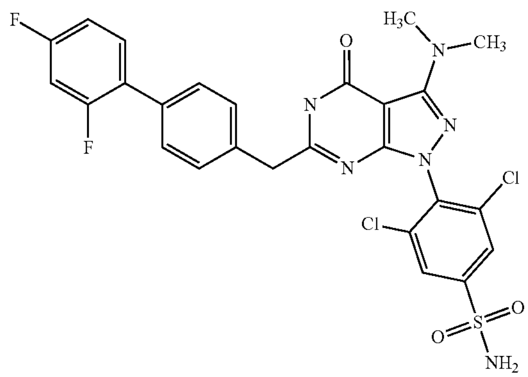 [SMILES: CN(C)c1nn(-c2c(Cl)cc(S(N)(=O)=O)cc2Cl)c2nc(Cc3ccc(-c4ccc(F)cc4F)cc3)[nH]c(=O)c12] |
| 92 | 3,5-Dichloro-4-[3-dimethylamino-6-(3'-hydroxy-biphenyl-4-ylmethyl)-4-oxo-4,5-dihydro-pyrazolo[3,4-d]pyrimidin-1-yl]-benzenesulfonamide | D | 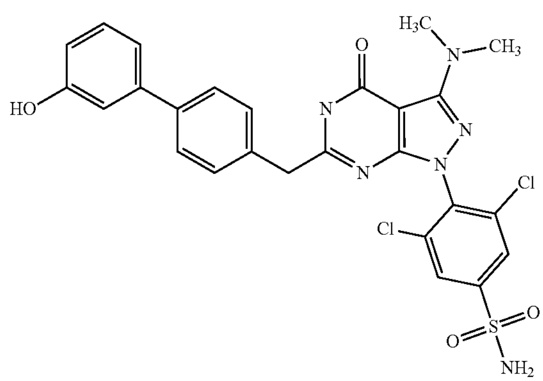 [SMILES: CN(C)c1nn(-c2c(Cl)cc(S(N)(=O)=O)cc2Cl)c2nc(Cc3ccc(-c4cccc(O)c4)cc3)[nH]c(=O)c12] |
| 93 | 6-Chloro-N-{5-[1-(2,6-dichloro-4-sulfamoyl-phenyl)-3-dimethylamino-4-oxo-4,5-dihydro-1H-pyrazolo[3,4-d]pyrimidin-6-yl[methyl]-2-methoxy-phenyl}-nicotinamide | F | 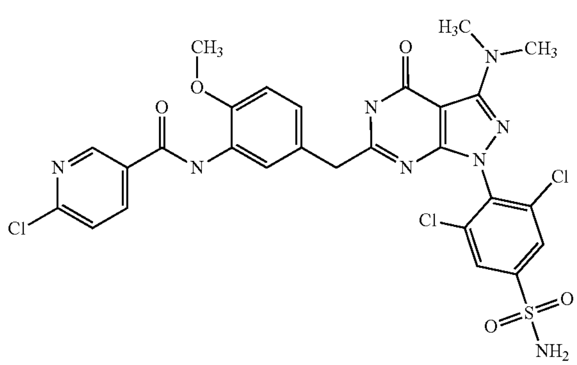 [SMILES: COc1ccc(Cc2nc3c(c(N(C)C)nn3-c3c(Cl)cc(S(N)(=O)=O)cc3Cl)c(=O)[nH]2)cc1NC(=O)c1ccc(Cl)nc1] |

TABLE 1-continued

Compounds of the invention
Compounds No. 1 to 5 and 7 to 9 are intermediate compounds according to the present invention.

| No. | Name | General method | Structure |
|---|---|---|---|
| 94 | N-{4-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl}-2-(3-dimethylamino-propylamino)-acetamide | G | 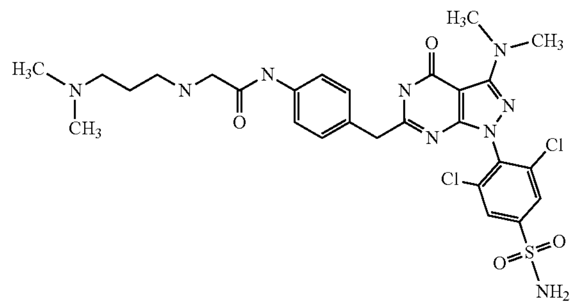 [SMILES: CN(C)CCCNCC(=O)Nc1ccc(Cc2nc3c(c(N(C)C)nn3-c3c(Cl)cc(S(N)(=O)=O)cc3Cl)c(=O)[nH]2)cc1] |
| 95 | N-{4-[1-(2,6-Dichloro-4-sulfamoyl-phenyl)-3-dimethylamino-4-oxo-4,5-dihydro-1H-pyrazolo[3,4-d]pyrimidin-6-ylmethyl]-phenyl)-2-dimethylamino-acetamide | G | 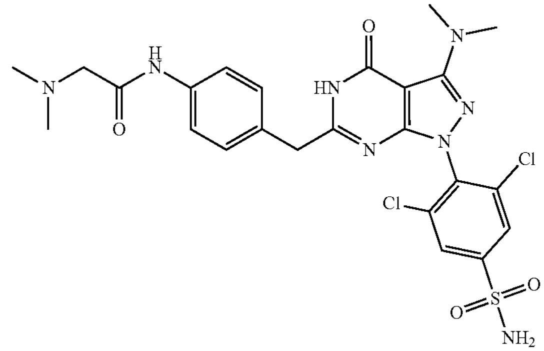 [SMILES: CN(C)CC(=O)Nc1ccc(Cc2nc3c(c(N(C)C)nn3-c3c(Cl)cc(S(N)(=O)=O)cc3Cl)c(=O)[nH]2)cc1] |
| 96 | 2-Diethylamino-N-{4-[1-(2,6-difluoro-4-sulfamoyl-phenyl)-3-dimethylamino-4-oxo-4,5-dihydro-1H-pyrazolo[3,4-d]pyrimidin-6-ylmethyl]-phenyl}-acetamide | G | 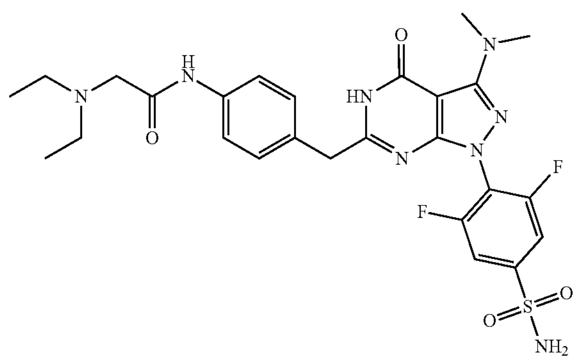 [SMILES: CCN(CC)CC(=O)Nc1ccc(Cc2nc3c(c(N(C)C)nn3-c3c(F)cc(S(N)(=O)=O)cc3F)c(=O)[nH]2)cc1] |
| 97 | 4-{6-[3-Amino-4-(1,4-dioxa-8-aza-spiro[4.5]dec-8-yl)-benzyl]-3-dimethylamino-4-oxo-4,5-dihydro-pyrazolo[3,4-d]pyrimidin-1-yl}-3,5-dichloro-benzenesulfonamide | C | 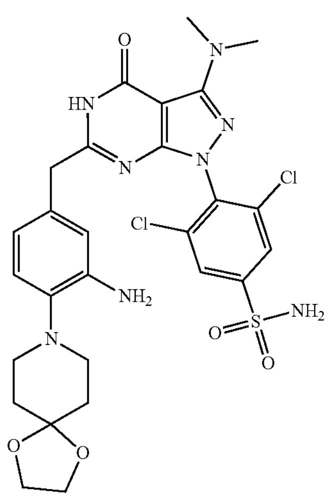 [SMILES: CN(C)c1nn(-c2c(Cl)cc(S(N)(=O)=O)cc2Cl)c2nc(Cc3ccc(N4CCC5(CC4)OCCO5)c(N)c3)[nH]c(=O)c12] |

TABLE 1-continued

Compounds of the invention
Compounds No. 1 to 5 and 7 to 9 are intermediate compounds according to the present invention.

| No. | Name | General method | Structure |
|---|---|---|---|
| 98 | 4-[6-(4-Butoxy-benzyl)-3-dimethylamino-4-oxo-4,5-dihydro-pyrazolo[3,4-d]pyrimidin-1-yl]-3,5-dichloro-benzoic acid | C | 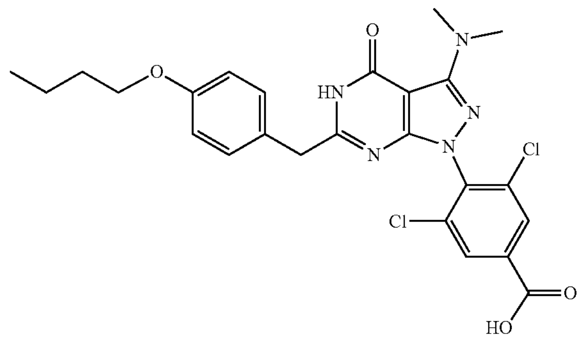 [SMILES: CCCCOc1ccc(Cc2nc3c(c(N(C)C)nn3-c3c(Cl)cc(C(=O)O)cc3Cl)c(=O)[nH]2)cc1] |

Analytical Characterisation

All of the prepared compounds were characterised by two independent analytical methods.

NMR

The 300 MHz $^1$H-NMR analysis was performed with an apparatus of type Bruker AVANCE-300 at 25° C., exact frequency was 300.14 MHz. Generally DMSO-$d_6$ was used as solvent, exceptions given. Chemical shifts are given in parts per million (δ) referenced to TMS (δ=0.00 ppm).

LCMS

The LCMS analysis was performed with a liquid chromatography mass-spectrometer Waters chromatograph with the following parameters:

Waters HPLC/MS:
MS detector: Waters SQD
UV detector: Waters 996 DAD
Separation module: Waters Alliance 2795
HPLC:
Column: Waters XBridge C18, 50 mm×4.6 mm, 3.5 μm
Solvent I: Water/0.1% HCOOH
Solvent II: AcCN
Acetonitrile: Riedel-deHaën; G Chromasolv (34998)
Water: Milli-Q Academic
Formic acid: Riedel-deHaën; extra pure (27001)

Flow rate: 2 ml/min
Injection: 5 μg
Gradient:

| time | Solv. I. | Solv. II. |
|---|---|---|
| 0.00 min | 95% | 5% |
| 0.50 min | 95% | 5% |
| 5.50 min | 5% | 95% |
| 6.00 min | 5% | 95% |
| 6.50 min | 95% | 5% |
| 7.00 min | 95% | 5% |

MS:
Ionisation: ES$^+$/ES$^-$
Source block temperature: 110° C.
Desolvation temperature: 250° C.
Desolvation gas: 500 L/h
Cone gas: 80 L/h
Capillary voltage: 3000 V
Cone voltage: 30 V
Extractor voltage: 6 V
Rf lens voltage: 0.1 V
Scan: 80 to 1000 m/z in 1 sec.
Inter-scan delay: 0.1 s

TABLE 2

LCMS and NMR data of the example compounds according to the present invention

| Example | NMR | MW calc monoisotopic | (MH−)− | (MH+)+ | Rt [min] |
|---|---|---|---|---|---|
| 1 | 3, 37(s, 1H) 13C:159.79, 116.68, 115.22, 51.31, 44.67 | | | | |
| 2 | 9.96(br.s, 3H), 7.57(br.s, 1H), 7.17(ddd, J = 9.6, 9.4 and 9.4 Hz, 1H), 6.88(ddd, J = 9.4, 4.2 and 1.8 Hz, 1H), 3.85(s, 3H) | | | | |
| 3 | 8.28(br.s, 1H), 8.07(s, 2H), 7.77(br.s, 1H), 6.83(br.s, 2H), 6.40(br.s, 2H), 2.67(s, 6H) | 356.05 | 355.07 | 357.00 | 2.13 |
| 4 | 7.95(s, 2H), 7.77(br.s, 2H) 6.78(br.s, 2H); 2.85(s, 6H) | 374.01 | 373.11 | 375.10 | 2.90 |
| 5 | 7.97(s, 2H), 7.78(br.s, 2H), 6.83(br.s, 2H), 6.49(br.s, 2H), 2.68(s, 6H) | 392.02 | 391.15 | 393.15 | 2.41 |
| 6 | 12.31(s, 1H), 8.06(s, 2H), 7.78(s, 2H), 7.11(dm, J~8.0 Hz, 2H), 6.77(dm, J~8.0 Hz, 2H), 3.74(s, 2H), 3.04(s, 6H) | 507.06 | 506.25 | 508.24 | 2.47 |
| 7 | 7.63(dm, J = 8.0 Hz, 2H), 7.54(m, 1H), 6.60(br.s, 2H), 2.84(s, 6H) | 295.04 | 294.04 | 296.11 | 3.17 |

TABLE 2-continued

LCMS and NMR data of the example compounds according to the present invention

| Example | NMR | MW calc monoisotopic | (MH−)− | (MH+)+ | Rt [min] |
|---|---|---|---|---|---|
| 8 | 7.64(dm, J = 7.6 Hz, 2H), 7.55(m, 1H), 6.83(br.s, 2H), 6.32(br.s, 2H), 2.66(s, 6H) | 313.05 | | 314.06 | 2.76 |
| 9 | 7.57(ddd, J = 9.7, 9.5 and 9.2 Hz, 1H), 7.02(ddd, J = 9.5, 4.1ans 2.1 Hz, 1H), 6.81(br.s, 2H), 6.23(br.s, 2H), 3.78(s, 3H), 2.65(s, 6H) | 311.12 | | 312.09 | 2.69 |
| 10 | 12.25(br.s, 1H), 9.34(br.s, 1H), 8.31(s, 1H), 7.98(s, 1H), 7.97(s, 2H), 7.06(dd, J = 7.5 and 7.5 Hz, 1H), 6.68(dm, J~7.5 Hz, 1H), 6.67(dd, J~1.5 and 1.5 Hz, 1H), 6.61(dm, J~7.5 Hz, 1H), 3.74(s, 2H), 3.04(s, 6H) | 473.06 | 472.02 | 474.02 | 3.02 |
| 11 | 12.24(br.s, 1H), 9.32(br.s, 1H), 7.69(m, 2H), 7.60(m, 1H), 7.06(dd, J = 7.6 and 7.6 Hz, 1H), 6.55-6-72(ovl.m, 3H), 3.75(s, 2H), 3.04(s, 6H) | 429.08 | 428.19 | 430.13 | 3.51 |
| 12 | 12.28(br.s, 1H), 10.68(s, 1H), 7.69(m, 2H), 7.60(m, 1H), 6.75-6.90(ovl.m, 3H), 4.51(s, 2H), 3.75(s, 2H), 3.03(s, 6H) | 484.08 | 483.11 | 485.08 | 3.43 |
| 13 | 12.33(br.s, 1H), 7.70(dm, J = 8.1 Hz, 2H), 7.60(m, 1H), 7.33(ddd, J = 7.9, 7.8 and 6.6 Hz, 1H), 7.01-7.14(ovl.m, 3H), 3.88(s, 2H), 3.04(s, 6H) | 431.07 | 430.08 | 432.05 | 4.13 |
| 14 | 12.23(br.s, 1H), 7.70(dm, J = 8.2 Hz, 2H), 7.60(m, 1H), 7.18(dm, J = 8.6 Hz, 2H), 6.83(dm, J = 8.6 Hz, 2H), 3.91(t, J = 6.4 Hz, 2H), 3.75(s, 2H), 3.03(s, 6H), 1.65(m, 2H), 1.40(m, 2H), 0.91(t, J = 7.3 Hz, 3H) | 485.14 | 484.15 | 486.11 | 4.82 |
| 15 | 12.23(br.s, 1H), 7.70(dm, J = 8.2 Hz, 2H), 7.61(m, 1H), 6.84(d, J = 1.2 Hz, 1H), 6.81(d, J = 8.2 Hz, 1H), 6.74(dd, J = 8.2amd 1.2 Hz, 1H), 5.96(s, 2H), 3.74(s, 2H), 3.03(s, 6H) | 457.07 | 456.06 | 458.05 | 3.97 |
| 16 | 12.14(br.s, 1H), 7.70(dm, J = 8.0 Hz, 2H), 7.60(m, 1H), 6.92(dm, J = 8.0 Hz, 2H), 6.45(dm, J = 8.0 Hz, 2H), 4.94(br.s, 2H), 3.62(s, 2H), 3.03(s, 6H) | 322.14 | 321.19 | 323.10 | 2.05 |
| 17 | 12.29(br.s, 1H), 7.70(dm, J = 7.9 Hz, 2H), 7.61(m, 1H), 7.19(dd, J = 8.0 and 7.7 Hz, 1H), 6.87(dd, J = 1.7 and 1.2 Hz, 1H), 6.84(dm, J = 7.7 Hz, 1H), 6.79(dm, J = 8.0 Hz, 1H), 3.81(s, 2H), 3.69(s, 3H), 3.03(s, 6H) | 443.09 | 442.07 | 444.03 | 4.03 |
| 18 | 12.33(br.s, 1H), 7.70(dm, J~8.0Hz, 2H), 7.60(m, 1H), 7.56(d, J~1.5 Hz, 1H), 7.54(d, J~8.5Hz, 1H), 7.24(dd, J = 8.3 and 1.5 Hz, 1H), 3.89(s, 2H), 3.04(s, 6H) | 481.00 | 479.95 | 481.95 | 4.61 |
| 19 | 12.25(br.s, 1H), 10.13(br.s, 1H), 7.71(dm, J~7.8 Hz, 2H), 7.61(m, 1H), 7.43(d, J = 1.5 Hz, 1H), 7.06(dd, J = 8.5 and 1.5 Hz, 1H), 6.85(d, J = 8.5 Hz, 1H), 3.72(s, 2H), 3.04(s, 6H) | 506.98 | 505.99 | 507.95 | 3.76 |
| 20 | 12.26(br.s, 1H), 7.70(dm, J = 8.2 Hz, 2H), 7.60(m, 1H), 7.16(dd, J = 7.7 and 7.5 Hz, 1H), 7.11(dd, J~1.5 and 1.5 Hz, 1H), 7.05(dm, J~7.5 Hz, 1H), 7.02(dm, J~7.5 Hz, 1H), 3.80(s, 2H), 3.03(s, 6H), 2.24(s, 3H) | 427.10 | 426.12 | 428.10 | 4.26 |
| 21 | 12.36(br.s, 1H), 9.33(s, 1H), 8.05(s, 2H), 7.77(br.s, 2H), 7.06(dd, J~7.8 and 7.6 Hz, 1H), 6.68(dm, J~7.6 Hz, 1H), 6.67(dd, J~1.3 and 1.0 Hz, 1H), 6.61(dm, J~7.8 Hz, 1H), 3.76(s, 2H), 3.05(s, 6H) | 508.05 | 507.01 | 508.98 | 2.99 |
| 22 | 8.61(s, 1H), 8.00-9.50(br.3H), 8.01(s, 2H), 7.94(s, 1H), 7.26(dm, J = 8.0 Hz, 2H), 7.18(dm, J = 8.0Hz, 2H), 5.35(s, 2H), 3.79(s, 2H), 3.04(s, 6H) | 573.08 | 572.30 | 574.30 | 2.95 |
| 23 | 9.86(s, 1H), 8.00-9.50(br, 3H), 8.00(s, 2H), 7.43(dd, J~1.3 and 1.0 Hz, 1H), 7.42(dm, J = 7.7 Hz, 1H), 7.17(dd, J = 7.7 and 7.7 Hz, 1H), 6.93(dm, J= 7.7 Hz, 1H), 3.80(s, 2H), 3.05(s, 6H), 2.01(s, 3H) | 549.07 | 548.29 | 550.28 | 2.98 |
| 24 | 12.38(br.s, 1H), 10.70(s, 1H), 8.05(s, 2H), 7.77(br.s, 2H), 6.75-6.89(ovl.m, 3H), 4.51(s, 2H), 3.76(s, 2H), 3.05(s, 6H) | 563.05 | 562.04 | 564.04 | 3.04 |
| 25 | 8.00-10.00(br.s, 3H), 8.03(s, 2H), 7.76(d, J = 1.8 Hz, 1H), 7.43(d, J = 1.2 Hz, 1H), 7.23(dm, J = 8.1 Hz, 2H), 7.12(dm, J = 8.1 Hz, 2H), 6.24(dd, J = 1.8 and 1. 2Hz, 1H), 5.27(s, 2H), 3.80(s, 2H), 3.04(s, 6H) | 572.09 | 571.09 | 573.09 | 3.31 |

TABLE 2-continued

LCMS and NMR data of the example compounds according to the present invention

| Example | NMR | MW calc monoisotopic | (MH−)− | (MH+)+ | Rt [min] |
|---|---|---|---|---|---|
| 26 | 8.00-10.00(br.s, 3H), 8.03(s, 2H), 7.21-7.29(m, 4H), 6.80-6.96(ovl.m, 4H), 3.82(s, 2H), 3.75(s, 3H), 3.46(s, 2H), 3.05(s, 6H), 2.94(m, 4H), 2.47(m, 4H) | 696.18 | 695.15 | 697.16 | 2.95 |
| 27 | 12.40(br.s, 1H), 8.05(s, 2H), 7.78(br.s, 2H), 7.34(ddd, J = 8.0, 7.5 and 7.0 Hz, 1H), 7.02-7.16(ovl.m, 3H), 3.89(s, 2H), 3.05(s, 6H) | 510.04 | 509.01 | 511.01 | 3.52 |
| 28 | 11.90(br.s, 1H), 8.47(dd, J~1.5 and 1.5 Hz, 1H), 8.41(dd, J~4.7 and 1.5 Hz, 1H), 7.61-7.71(ovl.m, 3H), 7.57(m, 1H), 7.29(dd, J = 7.7 and 4.7 Hz, 1H), 3.85(s, 2H), 3.03(s, 6H) | 414.08 | 413.10 | 415.07 | 2.58 |
| 29 | 11.35(br.s, 1H), 8.56(dd, J~1.5 and 1.5 Hz, 1H), 8.44(dd, J~1.5 and 1.5 Hz, 1H), 7.94(dd, J~1.51.5 Hz, 1H), 7.68(dm, J~8.0 Hz, 2H), 7.59(m, 1H), 3.85(s, 2H), 3.04(s, 6H) | 491.99 | 490.98 | 492.95 | 3.74 |
| 30 | 12.33(br.s, 1H), 8.06(s, 2H), 7.78(br.s, 2H), 7.19(dm, J = 8.7 Hz, 2H), 6.84(dm, J = 8.7 Hz, 2H), 3.91(t, J = 6.5 Hz, 2H), 3.76(s, 2H), 3.04(s, 6H), 1.65(m, 2H), 1.40(m, 2H), 0.91(t, J = 7.5 Hz, 3H) | 564.11 | 563.11 | 565.11 | 4.18 |
| 31 | 12.33(br.s, 1H), 8.06(s, 2H), 7.78(br.s, 2H), 6.85(d, J = 1.2 Hz, 1H), 6.82(d, J = 8.1 Hz, 1H), 6.76(dd, J = 8.1 and 1.2 Hz, 1H), 5.96(s, 1H), 3.75(s, 2H), 3.05(s, 6H) | 536.04 | 535.03 | 537.04 | 3.43 |
| 32 | 12.43(br.s, 1H), 8.05(s, 2H), 7.79(br.s, 2H), 7.57(d, J~1.5 Hz, 1H), 7.56(d, J~8.0 Hz, 1H), 7.25(dd, J~8.0 and 1.5 Hz, 1H), 3.90(s, 2H), 3.05(s, 6H) | 559.98 | 559.05 | 561.05 | 3.93 |
| 33 | 12.20(br.s, 1H), 7.62(ddd, J = 9.6, 9.4 and 9.4 Hz, 1H), 7.07(ddd, J = 9.4, 4.2 and 1.8 Hz, 1H), 6.85(d, J~1.5 Hz, 1H), 6.83(d, J~8.0 Hz, 1H), 6.75(dd, J~8.0 and 1.5 Hz, 1H), 5.96(s, 2H), 3.74(s, 2H), 3.72(s, 3H), 3.02(s, 6H) | 455.14 | 454.09 | 456.16 | 3.74 |
| 34 | 7.75-9.75(br.s, 3H), 8.55(dd, J~1.5 and 1.5 Hz, 1H), 8.45(dd, J~1.5 and 1.5 Hz, 1H), 8.02(s, 2H), 7.97(dd, J~1.5 and 1.5 Hz, 1H), 3.88(s, 2H), 3.04(s, 6H) | 570.96 | 569.90 | 571.88 | 3.19 |
| 35 | 12.37(br.s, 1H), 8.05(s, 2H), 7.78(br.s, 2H), 7.20(dd, J~8.0 and 7.5 Hz, 1H), 6.88(dd, J~1.5 and 1.5 Hz, 1H), 6.85(dm, J~7.5 Hz, 1H), 6.80(dm, J~8.0 Hz, 1H), 3.82(s, 2H), 3.70(s, 3H), 3.05(s, 6H) | 342.15 | 341.21 | 343.17 | 2.55 |
| 36 | 12.43(br.s, 1H), 8.06(s, 2H), 7.78(br.s, 2H), 7.37(dd, J~4.5 and 1.5 Hz, 1H), 6.91-6.98(ovl.m, 2H), 4.08(s, 2H), 3.05(s, 6H) | 498.01 | 496.96 | 498.93 | 3.37 |
| 37 | 12.35(br.s, 1H), 11.65(br.s, 1H), 8.06(s, 2H), 7.77(br.s, 2H), 7.19(d, J = 8.1 Hz, 1H), 7.03(d, J~1.5Hz, 1H), 7.00(dd, J~8.0 and 1.5 Hz, 1H), 3.85(s, 2H), 3.04(s, 6H) | 549.04 | 547.94 | 549.96 | 3.02 |
| 38 | 12.30(br.s, 1H), 7.63(ddd, J~9.5, 9.5 and 9.5 Hz, 1H), 7.38(dd, J~4.5 and 1.5 Hz, 1H), 7.06(ddd, J~9.23.7 and 1.5 Hz, 1H), 6.86-7.00(ovl.m, 2H), 4.06(s, 2H), 3.72(s, 3H), 3.03(s, 6H) | 417.11 | 416.08 | 418.11 | 3.69 |
| 39 | 12.34(br.s, 1H), 10.14(br.s, 1H), 8.06(s, 2H), 7.78(br.s, 2H), 7.45(d, J = 1.8 Hz, 1H), 7.07(dd, J = 8.2 and 1.8 Hz, 1H), 6.85(d, J = 8.2 Hz, 1H), 3.74(s, 2H), 3.05(s, 6H) | 585.96 | 584.88 | 586.93 | 3.27 |
| 40 | 12.42(br.s, 1H), 8.05(s, 2H), 7.78(br.s, 2H), 7.49(dm, J = 8.3 Hz, 2H), 7.24(dm, J = 8.3 Hz, 2H), 3.85(s, 2H), 3.05(s, 6H) | 569.96 | 568.90 | 570.93 | 3.78 |
| 41 | 12.43(br.s, 1H), 8.05(s, 2H), 7.84(d, J~1.5 Hz, 1H), 7.79(br.s, 2H), 7.55(dd, J~8.5 and 1.5 Hz, 1H), 7.31(d, J~8.5 Hz, 1H), 3.89(ovl.s, 5H), 3.05(s, 6H) | 567.05 | 566.03 | 567.98 | 3.42 |
| 42 | 12.26(br.s, 1H), 8.06(s, 2H), 7.80(br.s, 2H), 7.07(d, J~1.5 Hz, 1H), 7.03(d, J~7.7 Hz, 1H), 7.31(dd, J~7.7 and 1.5 Hz, 1H), 3.76(s, 2H), 3.05(s, 6H), 2.16(s, 3H), 2.15(s, 3H) | 520.08 | 519.08 | 521.05 | 3.82 |
| 43 | 12.34(br.s, 1H), 7.70(dm, J~7.5 Hz, 2H), 7.61(m, 1H), 7.37(dd, J = 4.7 and 1.5 Hz, 1H), 6.90-6.98(ovl.m, 2H), 4.06(s, 2H), 3.04(s, 6H) | 419.04 | 418.05 | 420.01 | 3.94 |
| 44 | 12.41(br.s, 1H), 7.69(dm, J = 8.2 Hz, 2H), 7.60(m, 1H), 6.13(s, 1H), 4.07(s, 2H), 3.05(s, 6H), 2.16(s, 3H) | 418.07 | 417.02 | 419.02 | 3.47 |

TABLE 2-continued

LCMS and NMR data of the example compounds according to the present invention

| Example | NMR | MW calc monoisotopic | (MH−)− | (MH+)+ | Rt [min] |
|---|---|---|---|---|---|
| 45 | 12.40(br.s, 1H), 8.05(s, 2H), 7.84(br.s, 2H), 7.32(ddm, J = 8.5 and 5.5 Hz, 2H), 7.12(ddm, J = 8.5 and 8.5 Hz, 2H), 3.85(s, 2H), 3.05(s, 6H) | 510.04 | 509.12 | 511.11 | 3.56 |
| 46 | 11.50(br.s, 1H), 8.06(ovl.m, 1H), 8.05(s, 2H), 8.00(br.s, 2H), 6.86(d, J~6.5 Hz, 1H), 6.70(d, J~1.5 Hz, 1H), 3.86(s, 2H), 3.81(s, 3H), 3.06(s, 6H) | 523.06 | 522.02 | 524.02 | 3.04 |
| 47 | 12.45(br.s, 1H), 8.16(d, J = 2.7 Hz, 1H), 8.08(d, J = 1.4 Hz, 1H), 8.05(s, 2H), 7.79(br.s, 2H), 7.28(dd, J = 2.7 and 1.4 Hz, 1H), 3.90(s, 2H), 3.76(s, 3H), 3.05(s, 6H) | 523.06 | 522.06 | 524.06 | 2.57 |
| 48 | 12.30(br.s, 1H), 8.05(s, 2H), 7.75(br.s, 2H), 8.87(dd, J = 11.2 and 8.7 Hz, 1H), 6.62(dd, J = 8.7 and 1.5 Hz, 1H), 6.40(m, 1H), 5.08(br.s, 2H), 3.69(s, 2H), 3.05(s, 6H) | 525.05 | 524.03 | 526.01 | 3.18 |
| 49 | 12.16(br.s, 1H), 8.03(s, 2H), 7.76(br.s, 2H), 7.20(br.s, 2H), 6.27(s, 1H), 3.74(s, 2H), 3.06(s, 6H) | 514.02 | 513.04 | 515.00 | 2.38 |
| 50 | 12.33(br.s, 1H), 8.06(s, 2H), 7.78(br.s, 2H), 7.17(dd, J~7.5 and 7.5 Hz, 1H), 7.12(dd, J~1.5 and 1.5 Hz, 1H), 7.06(dm, J~7.5 Hz, 1H), 7.03(dm, J~7.5 Hz, 1H), 3.81(s, 2H), 3.05(s, 6H), 2.25(s, 3H) | 506.07 | 505.11 | 507.11 | 3.65 |
| 51 | 12.25(br.s, 1H), 8.05(s, 2H), 7.80(br.s, 2H), 6.68(d, J = 8.1 Hz, 1H), 6.52(d, J = 1.7 Hz, 1H), 6.43(dd, J = 8.1 and 1.7 Hz, 1H), 4.66(br.s, 2H), 3.70(s, 3H), 3.65(s, 2H), 3.05(s, 6H) | 537.07 | 536.06 | 538.06 | 2.69 |
| 52 | 12.23(br.s, 1H), 7.62(m, 1H), 7.17(m, 1H), 6.98-7.12(ovl.m, 4H), 3.80(s, 2H), 3.70(s, 3H), 3.02(s, 6H), 2.25(s, 3H) | 425.17 | 429.19 | 426.20 | 4.01 |
| 53 | 12.50(br.s, 1H), 8.04(s, 2H), 7.77(br.s, 2H), 7.15(s, 1H), 4.29(s, 2H), 3.07(s, 6H), 2.30(s, 3H) | 513.02 | 512.07 | 514.09 | 3.14 |
| 54 | 12.40(br.s, 1H), 7.68(dm, J~8.0 Hz, 2H), 7.59(m, 1H), 7.14(s, 1H), 4.28(s, 2H), 3.06(s, 6H), 2.29(s, 3H) | 434.05 | 433.16 | 435.09 | 3.64 |
| 55 | 13.10(br.s, 1H), 8.05(s, 2H), 7.76(br.s, 2H), 7.50(dm, J~8.0 Hz, 2H), 7.02(dm, J~8.0 Hz, 2H), 3.78(s, 3H), 3.06(s, 6H) | 558.04 | 557.11 | 559.13 | 3.75 |
| 56 | 12.00(br.s, 1H), 7.99(s, 2H), 7.72(br.s, 2H), 7.45(m, 1H), 7.22-7.41(ovl.m, 3H), 3.03(s, 6H) | 546.03 | 545.08 | 547.10 | 3.79 |
| 57 | 12.36(br.s, 1H), 7.62(ddd, J = 10.0, 9.5 and 9.0 Hz, 1H), 7.15(s, 1H), 7.05(ddd, J = 9.0, 3.5 and 1.5 Hz, 1H), 4.28(s, 2H), 3.70(s, 3H), 3.04(s, 6H), 2.30(s, 3H) | 432.12 | 431.18 | 433.18 | 3.43 |
| 58 | 8.10(d, J = 2.5 Hz, 1H), 7.91(d, J = 1.1 Hz, 1H), 7.52(dm, J = 7.9 Hz, 2H), 7.47(m, 1H), 7.13(dd, J = 2.5 and 1.1 Hz, 1H), 3.77(s, 3H), 3.44(s, 2H), 2.88(s, 6H) | 444.09 | 443.16 | 445.16 | 2.88 |
| 59 | 7.83(s, 2H), 6.92(br.s, 1H), 6.77-6.81(ovl.m, 2H), 3.68(s, 3H), 3.66(s, 3H), 3.57(s, 2H), 3.02(s, 6H) | 552.07 | 551.02 | 553.04 | 3.24 |
| 60 | 12.36(br.s, 1H), 8.61(s, 1H), 8.60(s, 1H), 8.06(s, 2H), 7.78(br.s, 2H), 7.42(dm, J~8.0 Hz, 2H), 7.36(dm, J~8.2 Hz, 2H), 7.26(tm, J~8.0 Hz, 2H), 7.20(dm, J~8.2 Hz, 2H), 6.96(tm, J~8.0 Hz, 1H), 3.79(s, 2H), 3.05(s, 6H) | 626.10 | 625.23 | 627.20 | 3.65 |
| 61 | 12.39(br.s, 1H), 9.67(br.s, 1H), 8.06(s, 2H), 7.78(br.s, 2H), 7.24(dm, J~7.5 Hz, 2H), 7.12(dm, J~7.5 Hz, 2H), 3.81(s, 2H), 3.04(s, 6H), 2.94(s, 3H) | 585.04 | 584.22 | 586.25 | 3.06 |
| 62 | 12.33(br.s, 1H), 9.87(s, 1H), 8.06(s, 2H), 7.76(br.s, 2H), 7.47(dm, J = 8.4 Hz, 2H), 7.19(dm, J = 8.4 Hz, 2H), 3.79(s, 2H), 3.05(s, 6H), 2.01(s, 3H) | 549.07 | 548.25 | 550.24 | 2.96 |
| 63 | 12.44(br.s, 1H), 9.73(br.s, 1H), 8.04(s, 2H), 7.79(br.s, 2H), 7.24(dd, J~7.3 and 7.3 Hz, 1H), 7.11(dd, J~1.3 and 1.0 Hz, 1H), 7.06(dm, J~7.3 Hz, 1H), 7.00(dm, J~7.3 Hz, 1H), 3.84(s, 2H), 3.05(s, 6H), 2.94(s, 3H) | 585.04 | 584.23 | 586.18 | 3.09 |

TABLE 2-continued

LCMS and NMR data of the example compounds according to the present invention

| Example | NMR | MW calc monoisotopic | (MH−)− | (MH+)+ | Rt [min] |
|---|---|---|---|---|---|
| 64 | 12.41(s, 1H), 8.50(s, 1H), 8.04(s, 2H), 7.77(s, 2H), 7.19-7.37(ovl.m, 7H), 7.13(dd, J~7.5 and 7.5 Hz, 1H), 6.79(dm, J~7.5 Hz, 1H), 6.57(t, J~5.5 Hz, 1H), 4.28(d, J~5.5 Hz, 2H), 3.80(s, 2H), 3.05(s, 6H) | 640.12 | 639.33 | 641.30 | 3.59 |
| 65 | 12.34(s, 1H), 8.49(s, 1H), 8.06(s, 2H), 7.77(s, 2H), 7.18-7.38(ovl.m, 7H), 7.14(dm, J~7.5 Hz, 2H), 6.57(t, J~5.5 Hz, 1H), 4.27(d, J~5.5 Hz, 2H), 3.76(s, 2H), 3.05(s, 6H) | 640.12 | 639.32 | 641.30 | 3.54 |
| 66 | 12.32(br.s, 1H), 8.85(d, J = 2.0 Hz, 1H), 8.56(dd, J = 4.7 and 1.5 Hz, 1H), 8.03(ddd, J = 8.0, 2.0amd 1.5 Hz, 1H), 7.67(dm, J = 8.1 Hz, 2H), 7.62(ddd, J = 10.0, 9.5 and 9.0 Hz, 1H), 7.46(dd, J = 8.0 and 4.7 Hz, 1H), 7.40(dm, J = 8.1 Hz, 2H), 7.07(ddd, J = 9.5, 4.0 and 2.0 Hz, 1H), 3.91(s, 2H), 3.71(s, 3H), 3.02(s, 6H) | 488.18 | 487.10 | 489.16 | 2.91 |
| 67 | 12.45(br.s, 1H), 8.86(d, J = 1.8 Hz, 1H), 8.55(dd, J = 4.8 and 1.3 Hz, 1H), 8.07(s, 2H), 8.04(ddd, J = 8.1, 1.8 and 1.3 Hz, 1H), 7.79(br.s, 2H), 7.67, dm, J = 8.2 Hz, 2H), 7.47(dd, J = 8.1 and 4.8 Hz, 1H), 7.42(dm, J = 8.2 Hz, 2H), 3.92(s, 2H), 3.05(s, 6H) | 569.08 | 568.00 | 570.00 | 2.67 |
| 68 | 11.39(br.s, 1H), 8.04(s, 2H), 7.90(br.s, 2H), 7.26(d, J~6.5 Hz, 1H), 6.16(d, J~1.5 Hz, 1H), 6.05(dd, J~6.5 and 1.5 Hz, 1H), 3.67(s, 2H), 3.06(s, 6H) | 509.04 | 508.01 | 510.00 | 2.58 |
| 69 | 8.00(s, 2H), 7.93(dd, J~1.5 and 1.5 Hz, 1H), 7.92(dd, J~1.5 and 1.5 Hz, 1H), 7.04(dd, J~1.5 and 1.5 Hz, 1H), 3.71(s, 2H), 3.04(s, 6H) | 509.04 | 508.04 | 510.04 | 2.37 |
| 70 | 12.40(br.s, 1H), 9.63(s, 1H), 8.03(s, 2H), 7.79(ovl.m, 1H), 7.77(br.s, 2H), 7.15(dd, J~10.0 and 9.0 Hz, 1H), 7.01(m, 1H), 3.82(s, 2H), 3.05(s, 6H), 2.06(s, 3H) | 567.07 | 566.07 | 568.04 | 3.04 |
| 71 | 12.28(br.s, 1H), 12.05(s, 1H), 8.02(s, 2H), 7.76(br.s, 2H), 6.86(s, 1H), 3.92(s, 2H), 3.06(s, 6H), 2.09(s, 3H) | 556.03 | 555.00 | 556.98 | 2.98 |
| 72 | 12.48(br.s, 1H), 8.16(dd, J = 5.0 and 1.7 Hz, 1H), 8.06(s, 2H), 7.77(br.s, 2H), 7.70(dd, J = 7.3 and 1.7 Hz, 1H), 7.47(dm, J = 8.0 Hz, 2H), 7.35(dm, J = 8.0 Hz, 2H), 7.07(dd, J = 7.3 and 5.0 Hz, 1H), 3.90(s, 2H), 3.85(s, 3H), 3.05(s, 6H) | 699.09 | 598.03 | 600.04 | 3.72 |
| 73 | 12.45(br.s, 1H), 8.44(d, J = 5.3 Hz, 1H), 8.06(s, 2H), 7.82(d, J = 1.5 Hz, 1H), 7.80(dm, J8.3 Hz, 2H), 7.78(br.s, 2H), 7.72(dd, J = 5.3 and 1.5 Hz, 1H), 7.44(dm, J = 8.3 Hz, 2H), 3.94(s, 2H), 3.05(s, 6H) | 603.04 | 601.99 | 603.98 | 3.67 |
| 74 | 12.69(br.s, 1H), 12.33(br.s, 1H), 8.07(dm, J = 8.4 Hz, 2H), 8.03(s, 2H), 7.76(br.s, 2H), 7.60(dm, J = 8.4 Hz, 2H), 6.99(s, 1H), 3.99(s, 2H), 3.07(s, 6H) | 652.00 | 651.04 | 653.06 | 4.06 |
| 75 | 13.34(br.s, 1H), 8.09(d, J = 1.5 Hz, 1H), 8.03(s, 2H), 7.94(br.s, 1H), 7.76(br.s, 2H), 7.20-7.40(ovl.m, 5H), 7.28(t, J = 5.6 Hz, 1H), 6.86(d, J = 8.6 Hz, 1H), 6.77(dd, J = 8.6 and 1.5 Hz, 1H), 4.29(d, J = 5.6 Hz, 2H), 3.78(s, 3H), 3.73(s, 2H), 3.05(s, 6H) | 670.13 | 669.19 | 671.15 | 3.72 |
| 76 | 12.36(br.s, 1H), 9.30(s, 1H), 8.13(d, J = 1.8 Hz, 1H), 8.12(s, 1H), 8.04(s, 2H), 7.78(br.s, 2H), 7.46(ddm, J = 8.9 and 4.9 Hz, 2H), 7.13(ddm, J = 8.9 and 8.9 Hz, 2H), 6.93(d, J = 8.5 Hz, 1H), 6.85(dd, J = 8.5 and 1.8 Hz, 1H), 3.84(s, 3H), 3.76(s, 2H), 3.05(s, 6H) | 674.10 | 673.11 | 675.10 | 3.82 |
| 77 | 12.37(br.s, 1H), 9.04(s, 1H), 8.04(s, 2H), 7.87(d, J~1.8 Hz, 1H), 7.77(br.s, 2H), 6.90-7.00(ovl.m, 2H), 3.78(s, 3H), 3.76(s, 2H), 3.04(s, 6H), 2.05(s, 3H) | 579.09 | 578.19 | 580.15 | 3.08 |
| 78 | 12.48(br.s, 1H), 8.61(dm, J~4.0Hz, 2H), 8.06(s, 2H), 7.79(br.s, 2H), 7.75(dm, J~7.5 Hz, 2H), 7.68(dm, J~4.0 Hz, 2H), 7.44(dm, J~7.5 Hz, 2H), 3.93(s, 2H), 3.05(s, 6H) | 569.08 | 570.2 | 568.19 | 2.39 |
| 79 | 8.25-9.75(br.s, 3H), 8.03(s, 2H), 7.56(dm, J = 8.8 Hz, 2H), 7.53(dm, J = 8.2 Hz, 2H), 7.34(dm, J = 8.2 Hz, 2H), 6.99(dm, J = 8.8 Hz, 2H), 3.84(s, 2H), 3.78(s, 3H), 3.04(s, 6H) | 598.10 | 597.16 | 599.15 | 4.01 |

TABLE 2-continued

LCMS and NMR data of the example compounds according to the present invention

| Example | NMR | MW calc monoisotopic | (MH−)− | (MH+)+ | Rt [min] |
|---|---|---|---|---|---|
| 80 | 12.37(br.s, 1H), 9.43(s, 1H), 8.04(s, 2H), 7.93(d, J~1.5 Hz, 1H), 7.77(br.s, 2H), 7.01(dd, J~8.0 and 1.5 Hz, 1H), 6.99(d, J~8.0 Hz, 1H), 4.34(s, 2H), 3.80(s, 3H), 3.78(s, 2H), 3.05(s, 6H) | 613.05 | 612.17 | 614.10 | 3.45 |
| 81 | 12.32(br.s, 1H), 9.64(s, 1H), 8.16(d, J~1.5 Hz, 1H), 8.03(s, 2H), 7.78(br.s, 2H), 6.94-7.00(ovl.m, 2H), 3.84(s, 3H), 3.76(s, 2H), 3.64(m, 4H), 3.11(s, 2H), 3.04(s, 6H), 2.52(m, 4H) | 664.14 | 663.29 | 665.28 | 2.62 |
| 82 | 12.43(br.s, 1H), 8.07(s, 2H), 7.78(br.s, 2H), 7.60(dm, J = 8.1 Hz, 2H), 7.51(dd, J = 1.6 and 1.4Hz, 1H), 7.34-7.45(ovl.m, 4H), 7.29(dm, J = 7.2 Hz, 1H), 3.90(s, 2H), 3.05(s, 6H), 2.04(q, J = 7.3 Hz, 2H), 1.25(t, J = 7.3 Hz, 3H) | 628.09 | 627.11 | 629.13 | 4.45 |
| 83 | 12.42(br.s, 1H), 9.50(s, 1H), 8.06(s, 2H), 7.78(br.s, 2H), 7.49(dm, J = 8.1 Hz, 2H), 7.44(dm, J = 8.3 Hz, 2H), 7.31(dm, J = 8.1 Hz, 2H), 6.82(dm, J = 8.3 Hz, 2H), 3.87(s, 2H), 3.05(s, 6H) | 584.08 | 583.14 | 585.12 | 3.48 |
| 84 | 12.38(br.s, 1H), 9.48(s, 1H), 8.20(br.s, 1H), 8.13(d, J = 1.8 Hz, 1H), 8.05(s, 2H), 7.78(br.s, 2H), 7.55(dm, J = 9.0 Hz, 2H), 7.30(dm, J = 9.0Hz, 2H), 6.93(d, J = 8.3 Hz, 1H), 6.87(dd, J = 8.3 and 1.8 Hz, 1H), 3.84(s, 3H), 3.77(s, 2H . . . | 740.09 | 739.06 | 741.09 | 4.37 |
| 85 | 12.30(br.s, 1H), 9.67(s, 1H), 8.06(s, 2H), 7.80(br.s, 2H), 7.53(dm, J = 8.5 Hz, 2H), 7.22(dm, J = 8.5 Hz, 2H), 3.80(s, 2H), 3.62(m, 4H), 3.09(s, 2H), 3.04(s, 6H), 2.47(m, 4H) | 634.13 | 633.15 | 635.15 | 2.52 |
| 86 | 12.40(br.s, 1H), 10.76(br.s, 1H), 9.68(br.s, 1H), 8.06(s, 2H), 7.80(br.s, 2H), 7.54(dm, J = 8.4 Hz, 2H), 7.27(dm, J = 8.4 Hz, 2H), 4.11(br.s, 2H), 3.84(s, 2H), 3.22(m, 4H), 3.04(s, 6H), 1.23(t, J = 7.2 Hz, 6H) | 620.15 | 621.2 | 619.24 | 2.55, 2.31 |
| 87 | 12.37(br.s, 1H), 9.62(s, 1H), 8.06(s, 2H), 7.78(br.s, 2H), 7.53(dm, J = 8.5 Hz, 2H), 7.22(dm, J = 8.5 Hz, 2H), 3.80(s, 2H), 3.07(s, 2H), 3.05(s, 6H), 2.50(m, 4H), 2.37(m, 4H), 2.17(s, 3H) | 647.16 | 646.36 | 648.32 | 2.52 |
| 88 | 12.34(br.s, 1H), 9.31(s, 1H), 8.03(s, 2H), 7.87(d, J~1.5 Hz, 1H), 7.77(br.s, 2H), 6.90-7.00(ovl.m, 2H), 3.80(s, 3H), 3.74(s, 2H), 3.05(s, 6H), 2.02(m, 1H), 0.71-0.79(ovl.m, 4H) | 605.10 | 604.12 | 606.10 | 3.40 |
| 89 | 12.45(br.s, 1H), 8.12(br.s, 1H), 8.07(s, 2H), 8.06(br.s, 1H), 7.84(dm, J~8.0 Hz, 1H), 7.79(br.s, 2H), 7.78(ovl.m, 1H), 7.67(dm, J = 8.0 Hz, 2H), 7.52(dd, J = 8.0 and 7.7 Hz, 1H), 7.41 (dm, J = 8.0 Hz, 2H), 7.39(dd, J~1.5 and 1.5 Hz, 1H), 3.92(s, 2H), 3.05(s, 6H) | 611.09 | 610.08 | 612.05 | 3.22 |
| 90 | 12.45(br.s, 1H), 8.06(s, 2H), 7.77(br.s, 2H), 7.66(dm, J = 8.6 Hz, 2H), 7.60(dm, J = 8.1 Hz, 2H), 7.49(dm, J = 8.6 Hz, 2H), 7.38(dm, J = 8.1 Hz, 2H), 3.90(s, 2H), 3.05(s, 6H) | 602.045 | 600.99 | 602.99 | 4.34 |
| 91 | 12.45(br.s, 1H), 8.06(s, 2H), 7.78(br.s, 2H), 7.55(ddd, J = 9.0, 8.8 and 6.7 Hz, 1H), 7.46(dm, J = 8.2 Hz, 2H), 7.39(dm, J = 8.2 Hz, 2H), 7.34(ddd, J = 11.3, 9.0 and 2.5 Hz, 1H), 7.18, ddd, J = 8.8, 8.8 and 2.5 Hz, 1H), 3.92(s, 2H), 3.05(s, 6H) | 604.066 | 603.01 | 605.01 | 4.14 |
| 92 | 12.43(br.s, 1H), 9.48(s, 1H), 8.07(s, 2H), 7.78(br.s, 2H), 7.53(dm, J = 8.0 Hz, 2H), 7.35(dm, J = 8.0 Hz, 2H), 7.23(dd, J = 7.8 and 7.8 Hz, 1H), 7.02(dm, J = 7.8 Hz, 1H), 6.98, dd, J = 1.5 and 1.5 Hz, 1H), 6.75(dm, J = 7.8 Hz, 1H), 3.89(s, 2H), 3.05(s, 6H) | 584.08 | 583.02 | 584.99 | 3.57 |
| 93 | 12.40(br.s, 1H), 9.81(s, 1H), 8.92(d, J = 2.2 Hz, 1H), 8.31(dd, J = 8.2 and 2.2 Hz, 1H), 8.02(s, 2H), 7.77(br.s, 2H), 7.69(d, J = 8.2 Hz, 1H), 7.67(d, J = 1.5 Hz, 1H), 7.13(dd, J = 8.3 and 1.5 Hz, 1H), 7.04(d, J = 8.3 Hz, 1H), 3.81(s, 2H), 3.79(s, 3H), 3.05(s, 6H) | 676.06 | 675.05 | 677.05 | 3.50 |
| 94 | 9.82(br.s, 1H), 8.06(s, 2H), 7.52(dm, J = 8.2 Hz, 2H), 7.22(dm, J = 8.2 Hz, 2H), 3.80(s, 2H), 3.28(s, 2H), 3.05(s, 6H), 2.57(t, J = 6.7 Hz, 2H), 2.36(t, J = 6.7 Hz, 2H), 2.19(s, 6H), 1.59(tt, J = 6.7 and 6.7 Hz, 2H) | 649.2 | 650.32 | 648.36 | 2.12, 2.23 |

TABLE 2-continued

LCMS and NMR data of the example compounds according to the present invention

| Example | NMR | MW calc monoisotopic | (MH−)− | (MH+)+ | Rt [min] |
|---|---|---|---|---|---|
| 95 | 12.40 (s, 1H), 10.72 (s, 1H), 9.94 (br. s, 1H), 8.06 (s, 2H), 7.81 (s, 2H), 7.53 (dm, J = 8.3 Hz, 2H), 7.26 (dm, J = 8.3 Hz, 2H), 4.06 (s, 2H), 3.83 (s, 2H), 3.04 (s, 6H), 2.82 (s, 6H) | 592.11 | 591.2 | 593.2 | 2.61 |
| 96 | 12.40 (br, 1H), 9.58 (br, 1H), 7.78 (dm, J = 7.3 Hz, 2H), 7.75 (br, 2H), 7.56 (dm, J = 8.3 Hz, 2H), 7.23 (dm, J = 8.3 Hz, 2H), 3.82 (s, 2H), 3.12 (s, 2H), 3.04 (s, 6H), 2.58 (q, J = 7.2 Hz, 4H), 1.00 (t, J = 7.2 Hz, 6H) | 588.21 | 587.4 | 589.4 | 2.43 |
| 97 | 12.27 (br, 1H), 8.05 (s, 2H), 7.76 (br, 2H), 6.79 (d, J = 8.0 Hz, 1H), 6.53 (d, J = 1.8 Hz, 1H), 6.43 (dd, J = 8.0 and 1.8 Hz, 1H), 4.72 (s, 2H), 3.89 (s, 4H), 3.66 (s, 2H), 3.05 (s, 6H), 2.78 (m, 4H), 1.75 (m, 4H) | 648.14 | 647.2 | 649.2 | 3.13 |
| 98 | 13.75 (br, 1H), 12.30 (s, 1H), 8.10 (s, 2H), 7.18 (dm, J = 8.5 Hz, 2H), 6.84 (dm, J = 8.5 Hz, 2H), 3.90 (t, J = 6.5 Hz, 2H), 3.75 (s, 2H), 3.04 (s, 6H), 1.65 (ft, J = 7.0 and 6.5 Hz, 2H), 1.40 (qt, J = 7.5 and 7.0 Hz, 2H), 0.91 (t, J = 7.5 Hz, 3H) | 529.13 | 528.1 | 530.1 | 4.21 |

Solubility in Water

The water solubility of preferred compound 86 and the compound of Example 49 of WO 02/967654 A2 have been compared. The results are summarized in Table 3 below.

TABLE 3

Solubility in water

| | Compound 86 of the present invention | Compound of Example 49 of WO 02/067654 (reference compound) |
|---|---|---|
| Solubility in water at pH 2.0 (µM) | 129 | <1 |
| Solubility in water at pH 7.4 (µM) | 105 | <1 |

Biological Activity of the Compounds of the Invention

1. Cell Viability

Cell viability assays have been carried out in various different cancer cell lines such as multiple myeloma/plasmocytoma, non-small cell lung cancer (NSCLC), colorectal carcinoma, hepatocellular carcinoma and cervical cancer cell lines.

1.1 Cell Lines

A549/A549 (ATCC® CCL-185™), H358/NCI-H358 [H-358, H358] (ATCC® CRL-5807™), HCC827/HCC827 (ATCC® CRL-2868™), HCT116/HCT116 (ATCC® CCL-247™) HT29/HT-29 (ATCC® HTB-38™) Jurkat, MCF7/MCF7 (ATCC® HTB-22™) and PC3/PC-3 (ATCC® CRL-1435™) cell lines were purchased from ATCC.

KMS12-BM (DSMZ NO.: ACC 551), OPM2 (DSMZ NO.: ACC 50) U266/U266B1 [U266] (DSMZ NO.: ACC 9), RPM18226/RPMI 8226 (DSMZ NO.: ACC 402) were obtained from DSMZ.

HEP G2 [HEPG2] (ATCC® HB-8065™) and HCC827/ABCG2HCC827×ABCG2 cell lines were kind gifts from Membrane Research Group, Cell Biology Research Group, Budapest, Hungary.

HCC827×ABCG2 (http://www.creativecell.hu/catalog.html HC-0210) was established by retroviral transduction of human ATP-binding cassette, sub-family G, member 2 cDNA into HCC827 cells and flow cytometry sorting of the anti-Human ABCG2 (clone 5D3) immunolabelled population.

A431 (ATCC® CRL1555™, H1650/NCI H1650[H1650] (ATCC® CRL5883) and HeLa (ATCC® CCL-2™) cell lines were gift from 1$^{st}$ Department of Pathology and Experimental Cancer Research, Semmelweis University, Budapest.

H1975/NCI-H1975 [H-1975, H1975] (ATCC® CRL-5908™), PC9 (ECACC 90071810) and PC9-ER (PMID: 24535670) cell lines were kindly provided by the Cancer Research UK London Research Institute, Signal Transduction laboratory. PC9-ER cells were made erlotinib-insensitive by prolonged incubation with erlotinib. One identified genotypic change responsible for erlotinib resistance in the PC9-ER cells is the T790M mutation, but several not yet identified mechanisms can undoubtedly cause resistance as well other than EGFR gene alterations (Riely G J, et al, Clinical course of patients with non-small cell lung cancer and epidermal growth factor receptor exon 19 and exon 21 mutations treated with gefitinib or erlotinib. Clin Cancer Res, 2006. 12:839-44; Engelman J A et al Mechanisms of acquired resistance to epidermal growth factor receptor tyrosine kinase inhibitors in non-small cell lung cancer. Clin Cancer Res 2008, 14:2895-9). With the exception of A431 and HeLa cell lines, cells were cultured in RPMI-1640 supplemented with 10% heat inactivated fetal bovine serum (Gibco) and 1% Ab/Am (antibiotic/antimycotic)(Gibco) at 37° C. in a 5% CO$_2$ containing, humidified incubator. A431 and HeLa cell lines were cultured in DMEM supplemented with 10% heat inactivated fetal bovine serum (Gibco) and 1% Ab/Am.

1.2 Cell Viability Assay (Material & Methods)

Cell viability was determined with CellTiter-Glo Luminescent Cell Viability Assay Kit (PROMEGA Lot 305189). The luminescence signal was detected by Analyst® GT Multimode Reader. All compounds were dissolved in DMSO. Cells were plated in 384-well flat-bottom plates (PerkinElmer) in 1000 cells per well/30 µL. One day after seeding, compounds were added. Cell viability was measured after 72 h. The ratio of surviving cells and the untreated samples (positive control) was examined. Two kinds of negative control were employed for normalisation:

medium without cells containing 10 μM DMSO and cells treated with Staurosporine in 20 nM final concentrations. Experimental data were gained from the 10 point serial dilution of the compounds). The dose-response curves were generated by the XLfit (IDBS) software (reference).

Selected compounds of the present invention exhibited an $IC_{50}$ value of 0.001 to 0.1 μM) in various multiple myeloma cell lines tested such as 8226/ATCC® CCL-155™ and U266B1 [U266] (ATCC® TIB-196™).

Selected compounds of the present invention exhibited an $IC_{50}$ value of 0.0015 to 0.01 μM in colorectal carcinoma cells tested such as HCT116/HCT116 (ATCC® CCL-247™).

2. CDK Inhibition

CDK9 inhibitory activity of the compounds according to the present invention has been determined using a widely applicable high throughput TR-FRET assay for the measurement of kinase autophosphorylation, inter alia, described in Moshinsky D. J. et al, J Biomol. Screen 2003, pp. 443-452.

In this time-resolved fluorescence resonance energy transfer (TR-FRET) kinase activity assay, the kinase, fluorescence labeled substrate, and ATP are allowed to react. Then EDTA, to stop the reaction, and fluorescence labeled antibody are added to detect the phosphorylated product. The antibody associates with the phosphorylated fluorescence labeled substrate and results in an increased TR-FRET value.

The compounds of the present invention exhibited a CDK9 $IC_{50}$ in the range of 0.0006 to 0.001 μM.

Moreover, the compounds of the present invention exhibited an inhibitory activity in the following ranges:

CDK2/cycA 1-10 nM,
CDK9/cycT1 1-10 nM,
CDK3/cycE1 1-10 nM,
CDK5/p35 1-10 nM,
CDK16 1-20 nM,
CDK1/cycB 1-20 nM, and
CDK7/cycH 5-50 nM in an assay carried out according to the protocol described above.

3. Target Selectivity Profile (DiscoverX KinomeScan)

Target selectivity of any pharmacologically active substance is connected with its efficacy, as the target(s) must be involved in growth and/or survival of the tumour or in its metastasising behaviour; safety as the inhibited target(s) may also confer side effects as well as the indication as the target(s) must be expressed in the tumour types that are selected for clinical trials.

According to an analysis of kinase inhibitory selectivity carried out in accordance with Karaman M W et al., Nat Biotechnol. 2008 January; 26(1):127-32. doi: 10.1038/nbt1358. PubMed PMID: 18183025, the compounds of the present invention such as compound No 86 are active as inhibitors of CDK7, 13 and 16 in addition to CDK9 inhibition as stated above.

Such a targeting spectrum (CDKs 7, 9, 13 and 16) is considered useful in order to achieve efficacy in a wide range of tumours as these targets are important for survival (CDKs 7, 9, 13 and 16) of many tumours and are also widely expressed in various tumour types.

4. hERG Activity

The blockade of the hERG potassium channel is a major concern for drug-induced risk for QT prolongation and Torsade de Pointes and consequently a major cause of attrition in drug development In a medium-throughput electrophysiology based hERG assay carried out in accordance with Bridgland-Taylor M H et al., J Pharmacol Toxicol Methods. 2006 September-October; 54(2):189-99. Epub 2006 Mar. 6. PubMed PMID: 16563806, the compounds of the present invention such as compound No. 86 did not display any inhibitory activity on the human ether-a-go-go-related gene (hERG)-encoded K+ channel.

5. Pharmacokinetic Studies

Pharmacokinetic studies on the compounds of the present invention have been carried out in accordance with Endele R and Senn M., Int. J. Mass Spectrom. Ion Phys. 1983 January; 48:81-84. doi:10.1016/0020-7381(83)87033-8.

The compounds of the invention such as compound No. 86 display oral bioavailability. Oral bioavailability is a highly valuable characteristic of therapeutics, since such drugs can be delivered much easier than intravenously delivered drugs and as such the adherence to dosing schedules is usually higher. After accessing the bloodstream, compounds have to be delivered to the target tissue, in which tumours are located.

6. Drug-Drug Interactions (DDIs)

Cytochrome P450 (CYPs) are the major enzymes involved in drug metabolism, accounting for about 75% of the total metabolism. Most drugs undergo deactivation by CYPs, either directly or by facilitated excretion from the body. Also, many substances are bioactivated by CYPs to form their active compounds.

Inhibition of cytochrome P450 (CYP) enzymes is the most common cause of harmful DDIs and has led to the removal of several drugs from the market.

In assays carried out in accordance with the "Guideline on the investigation of drug interactions", CPMP/EWP/560/95/Rev. 1 Corr. 2, European Medicines Agency, Committee for Human Medicinal Products (CHMP) and "Guidance for Industry, Drug Interaction Studies—Study Design, Data Analysis, Implications for Dosing, and Labeling Recommendations", U.S. Department of Health and Human Services. Food and Drug Administration, Center for Drug Evaluation and Research (CDER) the compounds of the present invention such as compound No. 86 exhibited only weak inhibitory activity of most CYP enzymes while the corresponding 3-isopropyl derivatives exhibited much stronger inhibitory activity for CYP2B6 and CYP2D6.

7. Comparison of Compound 86 of the Invention with Compound of Example 121 of WO 2000/21926 A2

Compound 86 has been compared with the key compound of WO 2000/21926 A2 (Example 121) in an imaging based detection system.

Two different multiple myeloma (MM) cell lines (RPMI-8226 (DSMZ, ACC 402), NCI-H929 DSMZ, ACC 163) have been used and were cultured in mono- and co-culture with osteoblasts (OB) (Osteoblasts were obtained by culturing hMSCs with a differentiation inducing medium for two weeks) in accordance with the method of Karadag A. et al. *Journal of Bone and Mineral Research* Vol. 15, No. 10, 2000 page 1935-43.

The comparison of mono- and co-culture shows a difference in the $EC_{50}$ between compound 86 of the present invention and the key compound of WO 2000/21926 A2 (compound of Example 121, reference compound).

The reference compound exhibited a reduced activity (higher $EC_{50}$) in the co-culture experiment compared to the mono-culture, while compound 86 of the present invention retained its activity in the co-culture system. These results as summarized in Table 4 below indicate that compared to the reference compound 121 of WO 2000/21926 A2, compound 86 of the present invention exhibits a better anticancer activity in a co-culture-system which is more in vivo-like, and thus predictive for anti-cancer activity in a whole organism.

TABLE 4

Comparison of compound 86 and reference compound in mono-and co-culture

| compound | Compound 86 of the present invention | | | Reference compound | | |
|---|---|---|---|---|---|---|
| cell line | mono-culture $EC_{50}$ (µM) | co-culture (+ OB) $EC_{50}$ (µM) | multiplier mono-to co-culture | mono-culture $EC_{50}$ (µM) | co-culture (+ OB) $EC_{50}$ (µM) | multiplier mono-to co-culture |
| NCI-H929/GN2 | 0.062 | 0.072 | ×1.16 | 0.05 | 0.16 | ×3.2 |
| | 0.055 | 0.068 | ×1.24 | 0.065 | 0.15 | ×2.31 |
| RPMI-8226/GN1 | 0.14 | 0.14 | ×1 | 0.12 | 0.42 | ×3.5 |
| | 0.19 | 0.22 | ×1.16 | 0.2 | 0.52 | ×2.6 |
| | 0.12 | 0.18 | ×1.5 | 0.21 | 0.65 | ×3.1 |

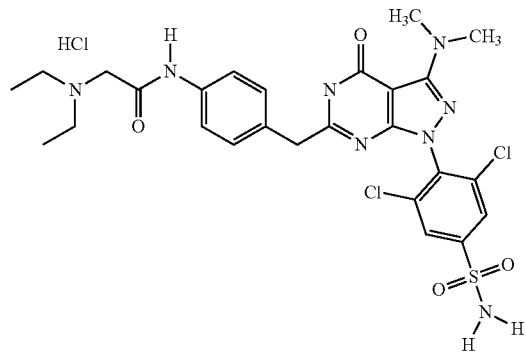

Compound 86

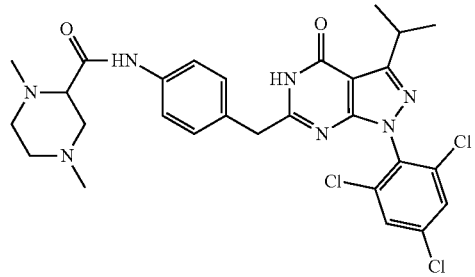

Example of 121 of WO2000/21926A2

8. Evaluation of the Antitumor Activity of Compound 86 Against Solid Tumors

In order to evaluate the antitumor activity of the compounds of the present invention, in particular compound 86, in solid tumors, an in vitro proliferation screening in a panel of 10 different human cancer cell lines derived from solid tumors (see Table 5, below) as a model system.

TABLE 5

Cancer cell lines used for testing the antitumor activity of compound 86

| Name | Cell origin |
|---|---|
| BXPC3 | pancreas |
| COLO205 | colon |
| DU145 | prostate |
| HCT116 | colon |
| HT1080 | connective tissue |
| MDAMB468 | breast |
| NCIH82 | lung |
| SKNAS | brain |
| U2OS | bone |
| UO31 | kidney |

Method

Six 10-fold dilutions of compound 86 have been prepared in DMSO, from $5\times10^{-9}$ M to $5\times10^{-4}$. Single data points have been tested for each concentration. The final concentration of DMSO was 0.1%. The duration of the treatment was 72 hours. The growth inhibition was measured by using Sulforhodamin B, a protein-staining assay in accordance with Vichai V et. al. Nat. Protoc. 2006; 1(3):1112-6. Activity of the agents was determined by evaluating the following parameters: $IC_{50}$, $GI_{50}$, $IC_{10}$, $GI_{10}$, TGI, $LC_{50}$, $IC_{90}$ and $GI_{90}$ (if these values could be calculated).

Results

Compound 86 showed growth inhibitory activity in the nanomolar range in 7 from 10 tested cancer cell lines (Table 6, below). Two cancer cell lines U2OS (bone) and UO31 (kidney) responded rather weakly in the micromolar range. The PBMC control cells were resistant to compound 86 treatment (Table 6, below), supporting a tumor cell specific toxicity of the compounds of the present invention. Both colon cancer cell lines COLO205 and HCT116 from the panel tested, showed $GI_{50}$ values in the low nanomolar range of $2.095\times10^{-08}$ and $5.822\times10^{-09}$ M, respectively, suggesting a significant antitumor activity in colon cancer. Furthermore, the lung cancer cell line NCIH82 showed strong growth inhibition upon treatment with compound 86 with a $GI_{50}$ of $1.652\times10^{-08}$ M. Even cell lines from tumors derived from pancreas (BXPC3) and connective tissue (HT1080), tumors that still lack efficient treatment, showed growth inhibition in the middle nanomolar range (Table 6, below).

TABLE 6

$GI_{50}$ and $IC_{50}$ values of cancer cell lines evaluated after 72 h of treatment with compound 86 of the present invention

| Cell line | Origin | GI50 | IC50 |
|---|---|---|---|
| BXPC3 | pancreas | 3.629E−08 | 4.183E−08 |
| COLO205 | colon | 2.095E−08 | 2.420E−08 |
| DU145 | prostate | 3.243E−08 | 3.731E−08 |
| HCT116 | colon | 5.822E−09 | 6.051E−09 |
| HT1080 | connective tissue | 3.635E−08 | 3.798E−08 |
| MDAMB468 | breast | 3.894E−08 | 4.297E−08 |
| NCIH82 | lung | 1.652E−08 | 2.131E−08 |
| PBMC | hematological | — | — |
| SKNAS | brain | 4.116E−08 | 7.431E−08 |
| U2OS | bone | 9.425E−08 | 1.026E−07 |
| UO31 | kidney | 3.394E−07 | 3.603E−07 |

Conclusions

1. Compound 86 showed a significant and specific antitumor activity in selected cell lines from solid tumors.
2. Compound 86 exhibited a strong antitumor activity in colon cancer cell lines. In particular, HCT116 cells were highly susceptible to compound 86 and have shown a $GI_{50}$ of 5.8 nM in the low nanomolar range. But also other cancer cell lines, for example NCIH82 (lung), DU145 (prostate) and BXPC3 (pancreas) showed promising responses to compound 86.

9. Investigation of the Mode of Action of the Compounds of the Invention (Compound 86)

In order to investigate the mode of action (MOA) related to the antitumor activity of the compounds of the present invention (in particular compound 86) in solid tumors and multiple myeloma, two experimental strategies were used to confirm the postulated MOA: 1) monitoring of apoptosis induction and 2) cell cycle analysis upon treatment with compound 86. Three cancer cell lines (LP-1, (multiple myeloma cells, DSMZ ACC 41), A375 (melanoma cells), and HeLa (cervix carcinoma cells)) as well as control cells (HS-5 bone marrow stroma cells, ATCC CRL-11882) were used to obtain mechanistic insight into the antitumor activity of compound 86.

Instrumentation and Reagents
Laminar Air-Flow (Kendro HERAsafe HSP-18)
Inkubator (Kendro HERAcell)
ImageXpress (Molecular Devices)
TACS Annexin V Kit (Trevigen #4830-01-K)
Colchicine (Sigma, C9754-100MG)
Propidium iodide solution (Sigma, P4864)
Saponin (Sigma, 47036)
Cell Scraper (Sarstedt Cat. 83.1832, Lot 1250400)
Mini Trans-Blot Cell (Biorad)
Mini-PROTEAN® Tetra Vertical Electrophoresis Cell (Biorad)
Methods
Cell Cycle:

Measuring of DNA content in cells is a well-established method for monitoring cell proliferation, cell cycle, fragmentation of nuclei (apoptosis) and DNA ploidy. Proliferating cells progress through various phases of the cell cycle (G0, G1, S, G2, and M phase). At different stages of the cell cycle and life cycle, cell nuclei contain different amounts of DNA. The DNA content in cell nuclei was analyzed by propidium iodide (PI) staining and FACS analysis after 12 and 24 h of treatment with 100 nM of compound 86 in accordance with the method of Desai Brijal M. et. al. PLOS Vol. 8; Issue 3; p. 1-11, 2013.

Apoptosis:

Annexin V staining and Poly(ADP-ribose)-Polymerase 1 (PARP) protein cleavage was analyzed to identify a pro-apoptotic effect of compound 86 on tumor cells in accordance with the method of Koopman G, et. al. Blood 1994; 1; 84(5):1415-20. Annexin V allows the identification of cell surface changes that occur early during the apoptotic process by in situ detection, which is ideal for the analysis with adherent cells. Cleavage of PARP-1 by caspases is considered to be a hallmark of apoptosis and was therefore applied to monitor apoptosis induction after 24 h of treatment with 100 nM of compound 86.

Results
Cell Cycle:

Cell cycle analysis revealed a strong impact on tumor cells. LP1 multiple myeloma cells showed a strong enrichment of nuclei in the sub_G1 fraction already after 12 h of treatment (FIG. 1A). The sub-G1 fraction usually corresponds to cells undergoing apoptosis with nuclei that start to fragment. After 24 h of treatment, almost all intact nuclei of LP1 cells disappeared due to massive cell death (FIG. 1a). A less pronounced but similar effect could be observed in the cell lines A375 and HeLa from solid tumors. A375 cells showed a G2/M arrest after 12 h and started to enrich in the sub_G1 fraction after 24 h of treatment (FIG. 1a). HeLa cells showed clear response to compound 86 after 24 h of treatment but were unaffected after 12 h of treatment. The non-cancer cell line HS-5 derived from healthy bone marrow stroma cells (ATCC CRL-11882) did not respond to compound 86. The cell cycle profile of HS-5 cells remained unchanged after 12 and 24 h of treatment (FIG. 1a). This suggests that compound 86 has a specific and selective antitumor activity and has only minor toxic effects on healthy cells.

Apoptosis:

To shed light on the mechanism of cell death, PARP cleavage was analyzed after 24 h of compound 86 treatment. The Western blot analysis showed specific induction of PARP cleavage in tumor cells (A375, LP1, and HeLa cells) but not in the healthy control cells HS-5 (FIG. 1b). These data further support the hypothesis that compound 86 induces apoptosis in tumor cells similar to Bortezomib (approved i.a. for the treatment of MM) in LP1 and HeLa cells. The effect on A375 melanoma cells was even stronger when compared to the known CDK1/CDK5 inhibitor Dinaciclib (FIG. 1b).

Figure 2:
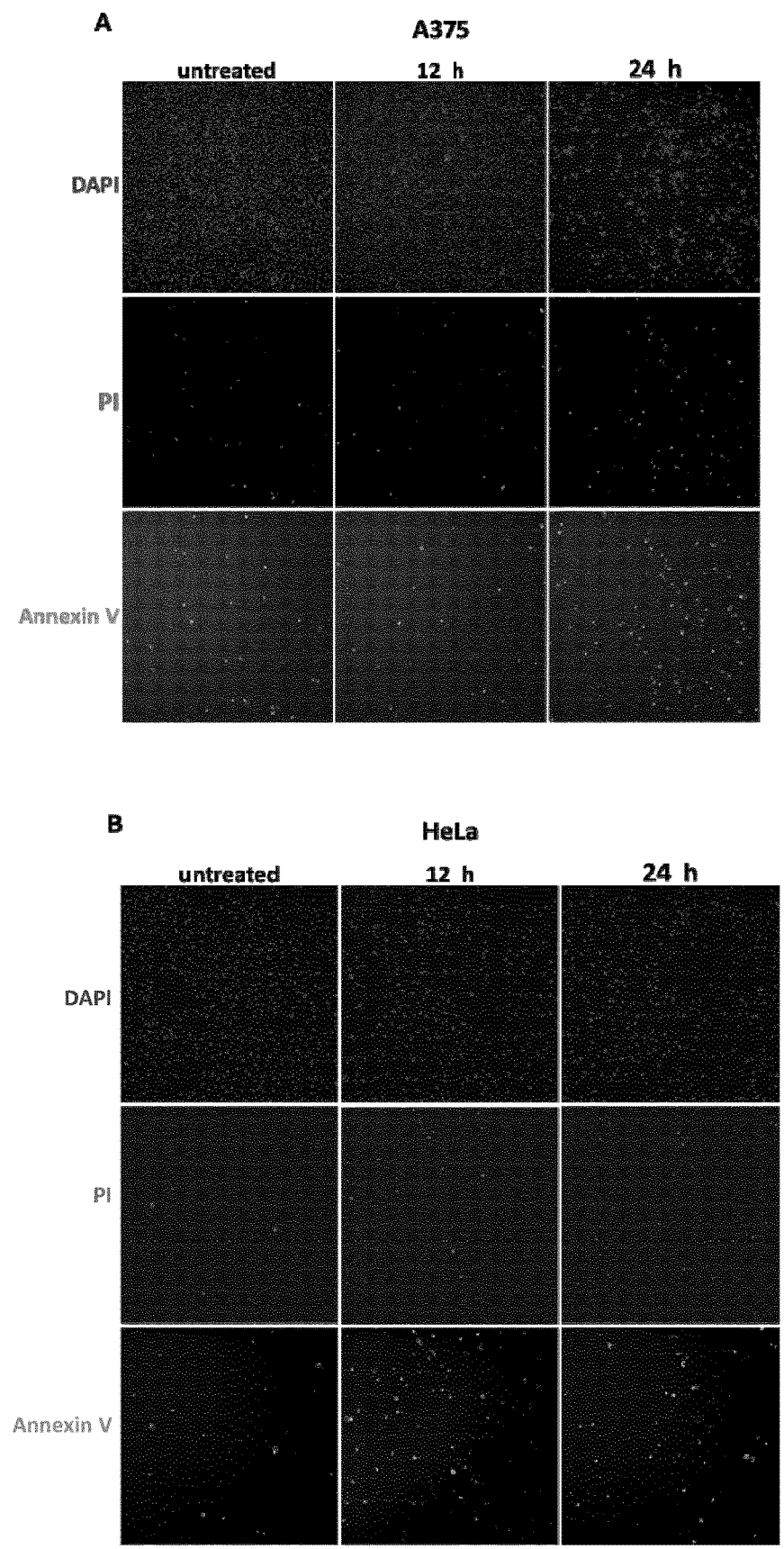
FIG. 2A shows images (10 x) of Annexin V/PI staining of the A375 melanoma cell line from solid tumors and control cells after 12 hours and 24 hours of treatment with 0.1 µM Otviciclib.
FIG. 2B depicts images (10 x) of Annexin V/PI staining of the HeLa cervix carcinoma cell line from solid tumors and control cells after 12 hours and 24 hours of treatment with 0.1 µM Otviciclib.
FIG. 2C provides images (10 x) of Annexin V/PI staining of the control cell line HS-5 cell line derived from bone marrow stroma after 12 hours and 24 hours of treatment with 0.1 µM Otviciclib.
FIG. 2D illustrates uantification of early apoptotic cells (Annexin V positive), late apoptotic cells (Annexin V/PI co-staining) and necrotic cells (PI positive) after Otviciclib treatment. Otviciclib showed a reproducible induction of apoptosis in tumor cells compared to control cells (n=3). 12 h . . . . Treatment with 0.1 µM Otviciclib for 12 hours; 24 h . . . Treatment with 0.1 µM Otviciclib for 24 hours; Colchicine . . . Treatment with 0.6 µg/ml colchicine for 24 hours.
Figure 2:
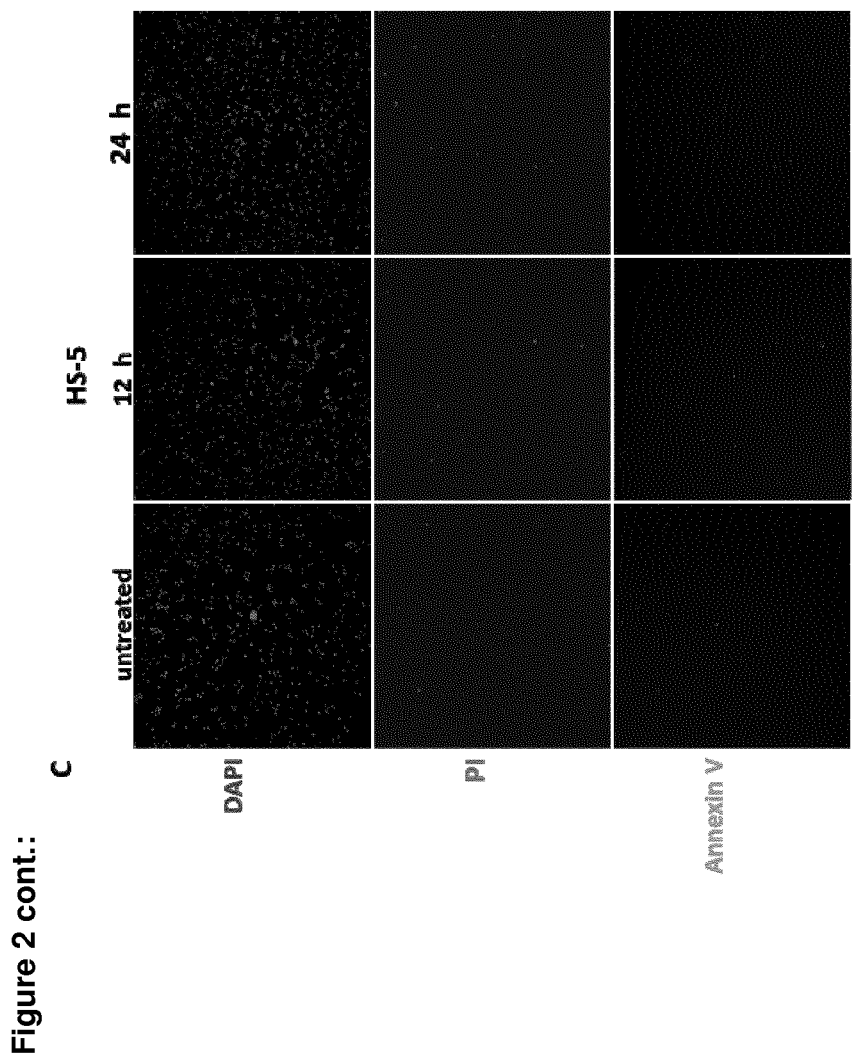

Annexin V/PI staining revealed a specific induction of apoptosis in the tumor cell lines A375 and HeLa (FIGS. 2a and b). The number of annexin V (early apoptotic cells) and annexin V/PI (late apoptotic cells) positive cells increased significantly after treatment with compound 86. The HS-5 cells did not respond to treatment with compound 86 (FIG. 2c). They did not enter the apoptotic and therefore did also not show elevated staining for annexin V (FIGS. 2c and d).

CONCLUSIONS

1. Compound 86 exhibits significant and specific induction of apoptosis in cancer cells. The effect was observed in multiple myeloma cells as well as cancer cells derived from solid tumors.
2. Compound 86 activity was selective for cancer cells and was not toxic for healthy control cells from the bone marrow.

The invention claimed is:

1. A compound or a stereoisomer thereof or a pharmaceutically acceptable salt, solvate, or prodrug thereof, wherein said compound is N-{4-[1-(2,6-dichloro-4-sulfamoyl-phenyl)-3-dimethylamino-4-oxo-4,5-dihydro-1H-pyrazolo[3,4-d]pyrimidin-6-ylmethyl]-phenyl}-2-diethyl-amino-acetamide.

2. A pharmaceutical composition comprising the compound according to claim 1 and optionally comprising a carrier and one or more pharmaceutically acceptable excipients.

3. The pharmaceutical composition according to claim 2, which is to be administered in combination with at least one compound selected from the group of proteasome inhibitors, cereblon-modulators/immune modulatory drugs, DNA damage inducers, MAPK pathway inhibitors, PI3K/Akt pathway inhibitors, TNF pathway agonists, pro apoptotic receptor agonists, selective BCL-2 family inhibitors/BH3 mimetic drugs, BET inhibitors, PARP inhibitors and/or radiotherapy.

4. The pharmaceutical composition according to claim 2 for oral or parenteral administration.

\* \* \* \* \*